US008034921B2

(12) United States Patent
Manoharan et al.

(10) Patent No.: US 8,034,921 B2
(45) Date of Patent: Oct. 11, 2011

(54) IRNA AGENTS TARGETING CCR5 EXPRESSING CELLS AND USES THEREOF

(75) Inventors: Muthiah Manoharan, Weston, MA (US); Kallanthottahil G. Rajeev, Wayland, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 853 days.

(21) Appl. No.: 11/944,227

(22) Filed: Nov. 21, 2007

(65) Prior Publication Data

US 2008/0255345 A1   Oct. 16, 2008

Related U.S. Application Data

(60) Provisional application No. 60/866,639, filed on Nov. 21, 2006.

(51) Int. Cl.
*C07H 21/04* (2006.01)
*A61K 31/70* (2006.01)

(52) U.S. Cl. ......................................... 536/24.5; 514/44

(58) Field of Classification Search ........................ None
See application file for complete search history.

(56) References Cited

U.S. PATENT DOCUMENTS

| | | | |
|---|---|---|---|
| 2003/0143732 A1 | 7/2003 | Fosnaugh et al. | |
| 2004/0170618 A1* | 9/2004 | Davis et al. ................... | 424/94.6 |
| 2004/0259247 A1 | 12/2004 | Tuschl et al. | |
| 2005/0256069 A1* | 11/2005 | Manoharan et al. ............ | 514/44 |
| 2006/0094678 A1 | 5/2006 | Vornlocher et al. | |
| 2007/0004664 A1 | 1/2007 | McSwiggen et al. | |
| 2007/0031844 A1 | 2/2007 | Khvorova et al. | |

FOREIGN PATENT DOCUMENTS

| | | |
|---|---|---|
| EP | 1448515 A1 | 8/2004 |
| WO | WO 02/22599 | 3/2002 |
| WO | WO 2005/115481 | 12/2005 |

OTHER PUBLICATIONS

Burrows et al. Bioorganic and Medicinal Chemistry Letters 2005, vol. 15, pp. 25-28.*
Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in Drosophila Melanogaster Embryo Lysate," The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA In Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Burrows, J., et al., Modulators of the human CCR5 receptor. Part 1: Discovery and initial SAR of 1-(-3,3-diphenylpropyl)-piperidinyl amides and ureas, Bioorg. Med. Chem. Lett. 2005, pp. 25-28, vol. 15.
Hammond, S.M., et al., "Argonaute2, a link between genetic and biochemical analyses of RNAi," Science, Aug. 10, 2001, pp. 1146-1150, vol. 293, No. 5532.
Imamura, S., et al., "CCR5 antagonists as anti-HIV-1 agents. Part 3: Synthesis and biological evaluation of piperidine-4-carboxamide derivatives," Bioorg. Med. Chem. Lett. 13:397-416, 2005.
Imamura, S., et al., "CCR5 antagonists as anti-HIV-1 agents. Part 2: Synthesis and biological evaluation of N-[3-(4-benzylpiperidin-1-yl)propyl]-N,N0-diphenylureas," Bioorg. Med. Chem. 12:2295-2306, 2004.
Kazmierski, W., et al., "Recent progress in discovery of small-molecule CCR5 chemokine receptor ligsnds as HIV-1 inhibitors," Bioorg Med Chem, 2003, 11: 2663-2676.
Ketting, R., el al. "Dicer functions in RNA interference and in synthesis of small RNA involved in developmental timing in C. elegans," Genes & Development, Oct. 15, 2001, pp. 2654-2659, vol. 15, No. 20.
Limbach, P., et al., "Summary: the modified nucleosides of RNA," Nucleic Acids Res., 1994, pp. 2183-2196, vol. 22, No. 12.
Maeda, K., et al., Spirodiketopiperazine-Based CCR5 Inhibitor Which Preserves CC-Chemokine/CCR5 Interactions and Exerts Potent Activity against R5 Human Immunodeficiency Virus Type 1 In Vitro, J. Virol., 2004, vol. 78, pp. 8654-8662.
Marozsan, A., et al., "Generation and properties of a human immunodeficiency virus type 1 isolate resistant to the small molecule CCR5 inhibitor, SCH-417690 (SCH-D)," Virology, Jul. 20, 2005, pp. 182-199, vol. 338, No. 1.

(Continued)

*Primary Examiner* — Tracy Vivlemore

(74) *Attorney, Agent, or Firm* — Fenwick & West LLP

(57) ABSTRACT

The invention relates to iRNA agents that preferably include a modification that targets CC chemokine receptor 5 (CCR5). The invention also relates to methods of making and using such modified iRNA agents.

24 Claims, 6 Drawing Sheets

OTHER PUBLICATIONS

Ribeiro, S., et al., "The clinical potential of chemokine receptor antagonists," Pharmacology and Therapeutics, Jul. 2005, pp. 44-58, vol. 107, Issue 1.

Seto, M., et al., "Orally Active CCR5 Antagonists as Anti-HIV-1 Agents: Synthesis and Biological Activity of 1-Benzothiepine 1, 1-Dioxide and 1-Benzazepine Derivatives Containing a Tertiary Amine Moiety," Chem. Pharm. Bull. 52:577-590, 2004.

Thoma, G., et al., "Orally Bioavailable Competitive CCR5 Antagonists," J. Med. Chem. 47:1939-1955, 2004.

Veazey, R.S., et al., "Prevention of virus transmission to macaque monkeys by a vaginally applied monoclonal antibody to HIV-1 gp120," Nature Medicine, 2003, pp. 343-346, vol. 9.

NM_000579 (GenBank [online] Bethesda, MC USA: United States National Library of Medicine [version dated Nov. 17, 2006; retrieved on Feb. 1, 2009] Retrieved from the internet URL:http://www.ncbi.nlm.nih.gov/entrez/viewer.fcgi?4502638:NCBI:15626606>, GenBank Accession No. NM_000579), 5 pages.

NM_000579 for CCR5 mRNA (GenBank [online] Bethesda, MC USA: United States National Library of Medicine [version dated Sep. 23, 2005; retrieved on Sep. 27, 2005] Retrieved from the internet URL:http://www.ncbi.nlm.nih.gov/entrez/viewer.fcgi?db=nucleotide&val=4502638>, GenBank Accession No. NM_000579), 28 pages.

* cited by examiner

```
   1    cttcagatag attatatctg gagtgaagga tcctgccacc tacgtatctg gcatagtatt
  61    ctgtgtagtg ggatgagcag agaacaaaaa caaaataatc cagtgagaaa agcccgtaaa
 121    taaaccttca gaccagagat ctattctcca gcttatttta agctcaactt aaaaagaaga
 181    actgttctct gattcttttc gccttcaata cacttaatga tttaactcca ccctccttca
 241    aaagaaacag catttcctac tttttatactg tctatatgat tgatttgcac agctcatctg
 301    gccagaagag ctgagacatc cgttccccta caagaaactc tccccgggtg gaacaagatg
 361    gattatcaag tgtcaagtcc aatctatgac atcaattatt atacatcgga gccctgccaa
 421    aaaatcaatg tgaagcaaat cgcagcccgc ctcctgcctc cgctctactc actggtgttc
 481    atctttggtt ttgtgggcaa catgctggtc atcctcatcc tgataaactg caaaaggctg
 541    aagagcatga ctgacatcta cctgctcaac ctggccatct ctgacctgtt tttccttctt
 601    actgtcccct ctgggctca ctatgctgcc gcccagtggg actttggaaa tacaatgtgt
 661    caactcttga cagggctcta ttttataggc ttcttctctg aatcttctt catcatcctc
 721    ctgacaatcg ataggtacct ggctgtcgtc catgctgtgt ttgctttaaa agccaggacg
 781    gtcacctttg gggtggtgac aagtgtgatc acttgggtgg tggctgtgtt tgcgtctctc
 841    ccaggaatca tcttaccag atctcaaaaa gaaggtcttc attacacctg cagctctcat
 901    tttccataca gtcagtatca attctggaag aatttccaga cattaaagat agtcatcttg
 961    gggctggtcc tgccgctgct tgtcatggtc atctgctact cgggaatcct aaaaactctg
1021    cttcggtgtc gaaatgagaa gaagaggcac agggctgtga ggcttatctt caccatcatg
1081    attgtttatt ttctcttctg ggctccctac aacattgtcc ttctcctgaa caccttccag
1141    gaattctttg gcctgaataa ttgcagtagc ctaacaggt tggaccaagc tatgcaggtg
1201    acagagactc tgggatgac gcactgctgc atcaaccca tcatctatgc ctttgtcggg
1261    gagaagttca gaaactacct cttagtcttc ttccaaaagc acattgccaa acgcttctgc
1321    aaatgctgtt ctatttccca gcaagaggct cccgagcgag caagctcagt ttacacccga
1381    tccactgggg agcaggaaat atctgtgggc ttgtgacacg gactcaagtg ggctggtgac
1441    ccagtcagag ttgtgcacat ggcttagttt catacacag cctggctgg gggtggggtg
1501    ggagaggtct tttttaaaag gaagttactg ttatagaggg tctaagattc atccatttat
1561    ttggcatctg tttaaagtag attagatctt ttaagcccat caattataga aagccaaatc
1621    aaaatatgtt gatgaaaaat agcaacctt ttatctcccc ttcacatgca tcaagttatt
1681    gacaaactct cccttcactc cgaaagttcc ttatgtatat ttaaaagaaa gcctcagaga
1741    attgctgatt cttgagttta gtgatctgaa cagaaatacc aaaattattt cagaaatgta
1801    caactttta cctagtacaa ggcaacatat aggttgtaaa tgtgtttaaa acaggtcttt
1861    gtcttgctat ggggagaaaa gacatgaata tgattagtaa agaaatgaca cttttcatgt
1921    gtgatttccc ctccaaggta tggttaataa gtttcactga cttagaacca ggcgagagac
1981    ttgtggcctg ggagagctgg ggaagcttct taaatgagaa ggaatttgag ttggatcatc
2041    tattgctggc aaagacagaa gcctcactgc aagcactgca tgggcaagct tggctgtaga
2101    aggagacaga gctggttggg aagacatggg gaggaaggac aaggctagat catgaagaac
2161    cttgacggca ttgctccgtc taagtcatga gctgagcagg gagatcctgg ttggtgttgc
2221    agaaggttta ctctgtggcc aaaggagggt caggaaggat gagcatttag ggcaaggaga
2281    ccaccaacag ccctccaggtc agggtgagga tggcctctgc taagctcaag gcgtgaggat
2341    gggaaggagg gaggtattcg taaggatggg aaggagggag gtattcgtgc agcatatgag
2401    gatgcagagt cagcagaact ggggtggatt tggtttggaa gtgagggtca gagaggagtc
2461    agagagaatc cctagtcttc aagcagattg gagaaaccct tgaaaagaca tcaagcacag
2521    aaggaggagg aggaggttta ggtcaagaag aagatggatt ggtgtaaaag gatgggtctg
2581    gtttgcagag cttgaacaca gtctcaccca gactccaggc tgtctttcac tgaatgcttc
2641    tgacttcata gatttccttc ccatcccagc tgaaatactg aggggtctcc aggaggagac
2701    tagatttatg aatacacgag gtatgaggtc taggaacata cttcagctca cacatgagat
2761    ctaggtgagg attgattacc tagtagtcat ttcatgggtt gttgggagga ttctatgagg
2821    caaccacagg cagcatttag cacatactac acattcaata agcatcaaac tcttagttac
2881    tcattcaggg atagcactga gcaaagcatt gagcaaaggg gtcccatata ggtgagggaa
2941    gcctgaaaaa ctaagatgct gcctgcccag tgcacacaag tgtaggtatc atttttctgca
3001    tttaaccgtc aataggcaaa gggggaagg gacatattca tttggaaata agctgccttg
3061    agccttaaaa cccacaaaag tacaatttac cagcctccgt atttcagact gaatgggggt
```

FIG. 5

```
3121  gggggggggcg ccttaggtac ttattccaga tgccttctcc agacaaacca gaagcaacag
3181  aaaaaatcgt ctctccctcc ctttgaaatg aatatacccc ttagtgtttg ggtatattca
3241  tttcaaaggg agagagagag gttttttttct gttctttctc atatgattgt gcacatactt
3301  gagactgttt tgaatttggg ggatggctaa aaccatcata gtacaggtaa ggtgagggaa
3361  tagtaagtgg tgagaactac tcagggaatg aaggtgtcag aataataaga ggtgctactg
3421  actttctcag cctctgaata tgaacggtga gcattgtggc tgtcagcagg aagcaacgaa
3481  gggaaatgtc tttccttttg ctcttaagtt gtggagagtg caacagtagc ataggaccct
3541  accctctggg ccaagtcaaa gacattctga catcttagta tttgcatatt cttatgtatg
3601  tgaaagttac aaattgcttg aagaaaata tgcatctaat aaaaaacacc ttcta
```

SEQ ID NO:1

FIG. 5 (cont.)

IRNA AGENTS TARGETING CCR5 EXPRESSING CELLS AND USES THEREOF

CROSS REFERENCE TO RELATED APPLICATIONS

Pursuant to 35 USC §119, this application claims the benefit of provisional Application Ser. No. 60/866,639 filed Nov. 21, 2006, the entire contents of which are incorporated herein by reference.

TECHNICAL FIELD

The invention relates to iRNA agents that preferably include a modification that targets CC chemokine receptor 5 (CCR5). The invention also relates to methods of making and using such modified iRNA agents.

BACKGROUND

CC Chemokine receptor 5 (CCR5) is a coreceptor for the human immunodeficiency virus-1 (HIV-1). CCR5 is expressed by bone marrow-derived cells known to be targets for HIV-1 infection, including a subpopulation of lymphocytes and monocytes/macrophages in blood, primary and secondary lymphoid organs, and noninflamed tissues. An increased number of CCR5-positive mononuclear cells have been found in chronically inflamed tissues, and the number of immunoreactive cells in these tissues was directly associated with a histopathologic correlate of inflammatory severity.

SUMMARY

The inventor has discovered, inter alia, that CCR5-binding ligands conjugated to iRNA agents are useful for the delivery of the iRNA agents to cells expressing CCR5. CCR5-binding ligands include CCR5 antagonists such as those described in Table 1, column 1, and the means for conjugating the CCR5 antagonists are illustrated in Table 1, column 2, as well as in the schematics of FIGS. 1, 2, and 3. The CCR5-binding ligand can be any molecule, including a chemical compound, antibody, or antibody fragment.

In one aspect the invention features an iRNA agent modified for enhanced delivery and uptake into a CCR5-expressing cell. The modified iRNA agent includes a CCR5-binding ligand, which, in some embodiments, is a CCR5 antagonist (e.g., a CCR5 antagonist listed in Table 1). In a preferred embodiment, the CCR5-binding ligand is conjugated to the iRNA agent. In one embodiment, the CCR5-binding ligand is conjugated to the iRNA agent via an intermediate (e.g., a tether and, optionally, a linker). In a preferred embodiment, the coupling is by a tether or a linker (or both) as described herein, and the complex has the formula represented by:

Ligand–[linker]$_{optional}$–[tether]$_{optional}$–iRNA agent

In certain embodiments, the ligand is a CCR5 antagonist attached to the iRNA agent as shown in Table 1, column I, and according to the schematics in FIGS. 1, 2, and 3.

TABLE 1
CCR5 antagonists and the corresponding conjugates.
| CCR5 Antagonist I | CCR5 antagonist conjugate[1] II |
|---|---|
| 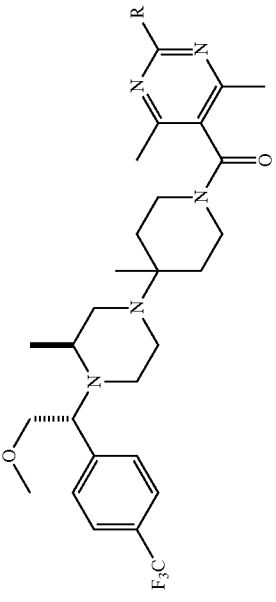 1 (IC$_{50}$ = 0.45 nM)<br>Ref: (a) IDdb Drug Report, 2004, C-6448; (b) IDdb Drug Report, 2005, Sch-417690; (c) Ribeiro, Honk, Pharmacology and Therapeutics, 107: 44-58, 2005. |  2 |
| 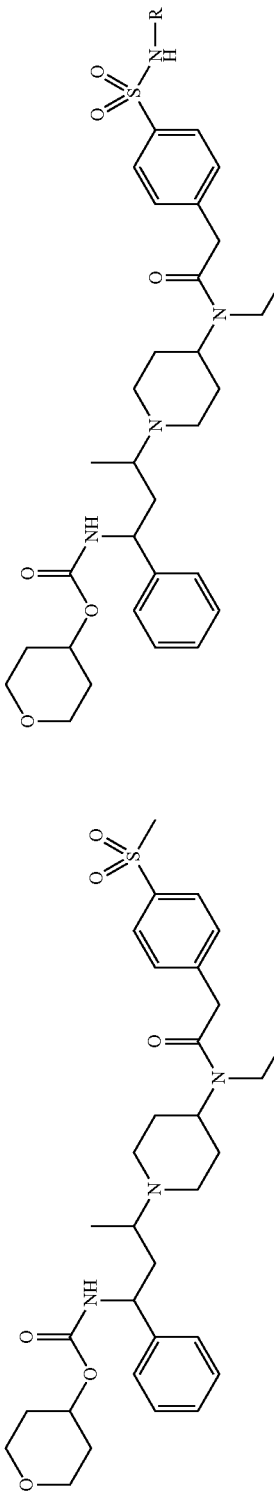 3 (IC$_{50}$ = 0.19 nM)<br>Ref: (a) EP1448525 A1; (b) Ribeiro and Honuk, Pharmacology and Therapeutics, 107: 44-58, 2005. | 4 |

TABLE 1-continued

CCR5 antagonists and the corresponding conjugates.

| CCR5 Antagonist I | CCR5 antagonist conjugate¹ II |
|---|---|
| 5a (X = NH2, IC₅₀ = 38 nM)<br>5b (X = NMe₂, IC₅₀ 10 nM)<br>Ref: Burrows et al., Bioorg. Med. Chem. Lett. 15: 25-28, 2005. | 6<br>R' = H, Me, Et, Allyl, Cyclopropyl isobutyl, isopropyl |
| 7 (IC₅₀ = 49 nM)<br>Ref: Burrows et al., Bioorg. Med. Chem. Lett. 15: 25-28, 2005. | 8 |
| 9a (X = SO₂NH₂, IC₅₀ = 3.4 nM)<br>9b (X = SO₂NHMe, IC₅₀ = 1.5 nM)<br>9c (X = SO₂NMe₂, IC₅₀ = 1.2 nM)<br>9d (X = SO₂(morpholino), IC₅₀ = 1.3 nM)<br>Ref: Imamura et al., Bioorg. Med. Chem. Lett. 13: 397-416, 2005. | 10 |

TABLE 1-continued

CCR5 antagonists and the corresponding conjugates.

| CCR5 Antagonist I | CCR5 antagonist conjugate¹ II |
|---|---|
| 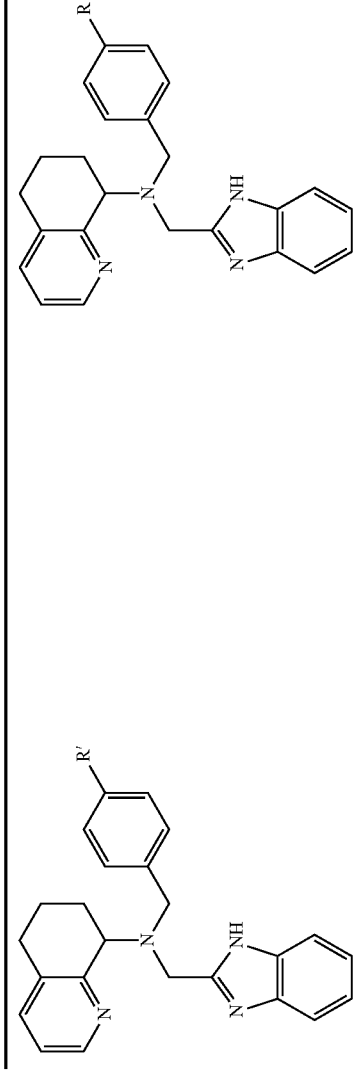<br>11 (IC$_{50}$ = 0.002-20 μg/mL, HIV replication)<br>Ref: (a) *WO00222599*; (b) Ribeiro and Horuk, *Pharmacology and Therapeutics*, 107: 44-58, 2005. | 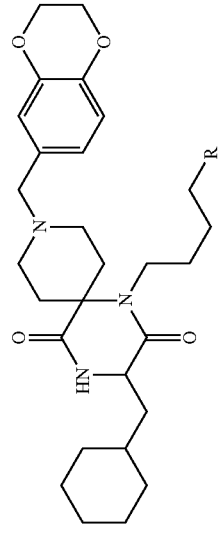<br>12 |
| 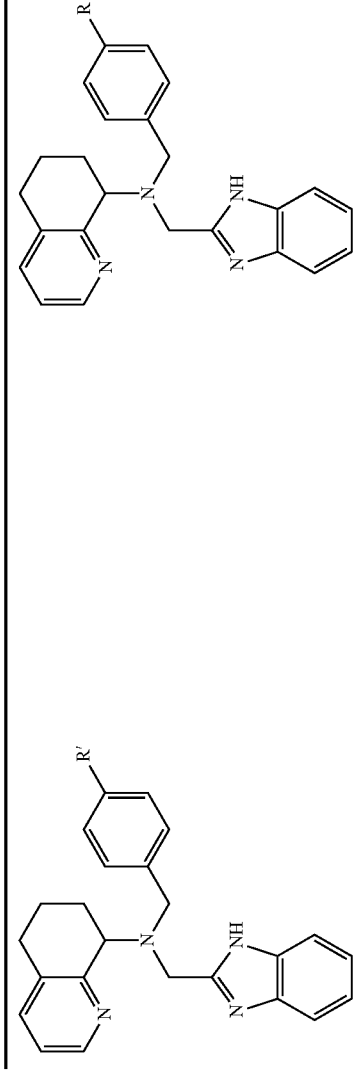<br>13 (IC$_{50}$ = 1 nM, viral replication)<br>Ref: (a) Maeda et al., *J. Virol.* 78: 8654-8662, 2004;<br>(b) Ribeiro and Horuk, *Pharmacology and Therapeutics*, 107: 44-58, 2005. | 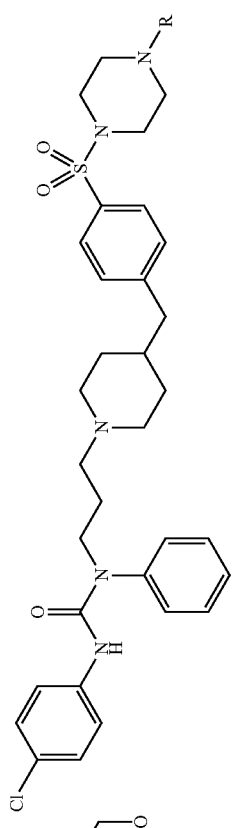<br>14 |
| 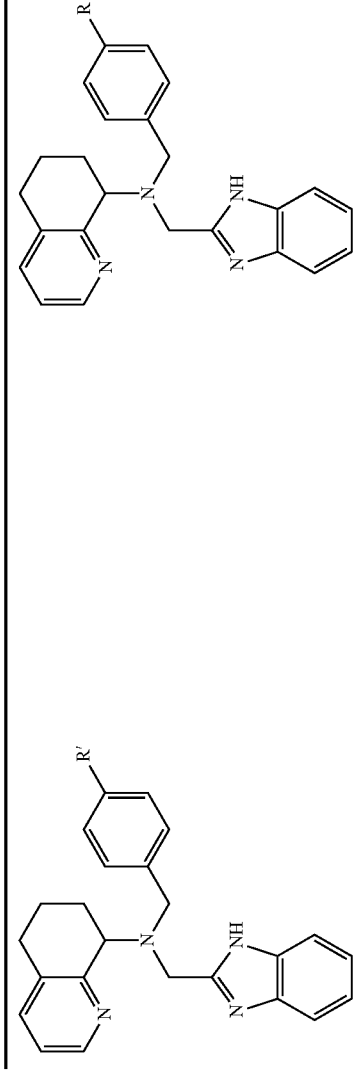<br>15 (IC$_{50}$ = 1.0 nM, CHO cells)<br>Ref: Imamura et al., *Bioorg. Med. Chem.* 12: 2295-2306, 2004. | 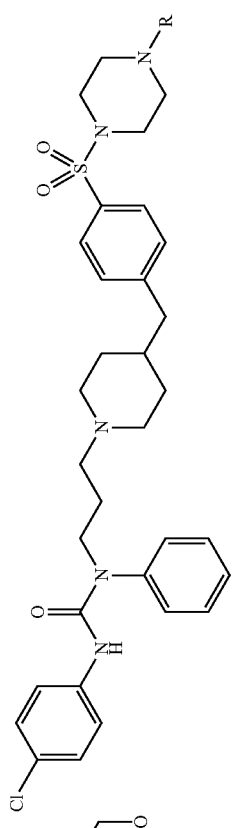<br>16 |

TABLE 1-continued
CCR5 antagonists and the corresponding conjugates.
| CCR5 Antagonist I | CCR5 antagonist conjugate¹ II |
|---|---|
| 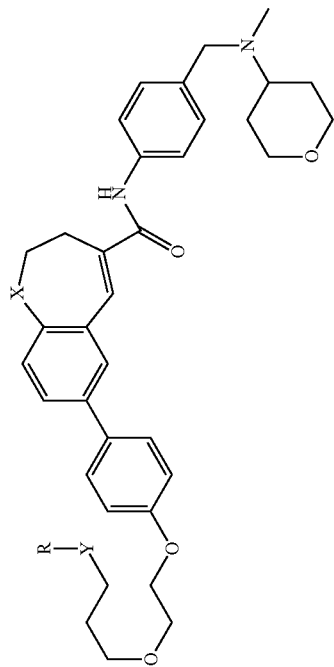 | 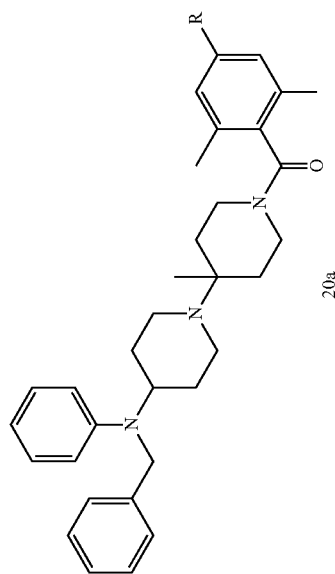 |
| | Y = O, NH, CO |
| | 18 |
| 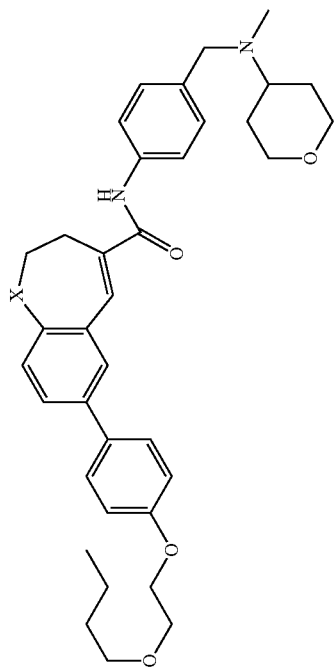 | 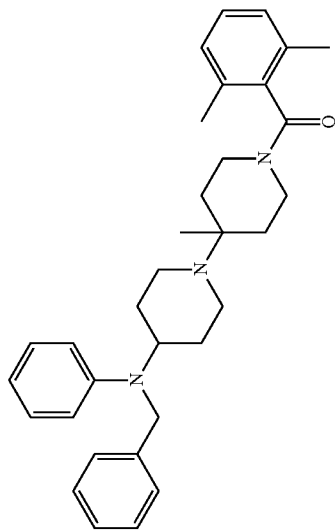 |
| 17a (X = SO₂, IC₅₀ = 27 nM) | 20a |
| 17b (X = N-i-Bu, IC₅₀ = 3.6 nM) | |
| Ref: Seto et al., Chem. Pharm. Bull. 52: 577-590, 2004. | |

TABLE 1-continued

CCR5 antagonists and the corresponding conjugates.

| CCR5 Antagonist I | CCR5 antagonist conjugate[1] II |
|---|---|
| 19 ($IC_{50}$ = 2.6 nM, human; 0.7 nM, Cyano-transfected CHO cells)<br>Ref: Thoma et al., J. Med. Chem. 47: 1939-1955, 2004.<br>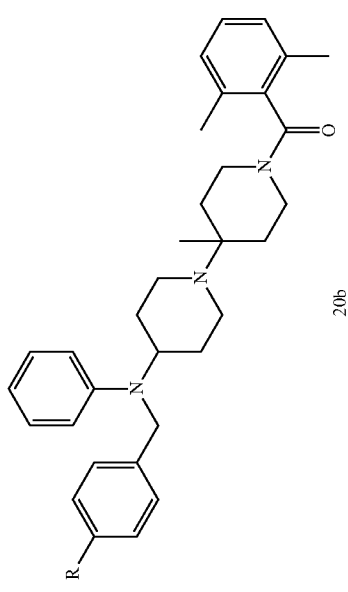20b | 21 ($IC_{50}$ = 4.4 nM, [$^{125}$I]-MIP-1$^{\alpha}$ binding)<br>Ref: Kazmierski et al., Bioorg. Med. Chem. 11: 2663-2676, 2003.<br>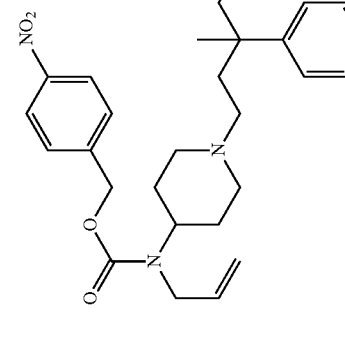<br>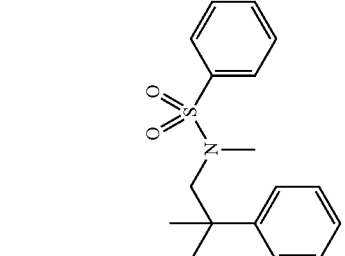22a (X = phosphoramidite)<br>22b (X = CPG)<br>22c (X = oligonucleotide) |

[1]R indicates the site of the tether, linker, and oligonucleotide as illustrated in FIGS. 1, 2 and 3.

Ligands shown in Table 1, column I were selected on the basis of biological data regarding their affinity for CCR5. Compound 1 (Table 1) has successfully completed a phase I clinical trial and was well tolerated in this study in 48 HIV-infected patients. A dose-dependent reduction in viral load was observed with no cardiovascular side effects. Compound 1 has a good pharmacokinetic profile, 100% bioavailability, and 84% protein binding with good central nervous system (CNS) penetration. The compound also did not cause an inhibition or induction of liver enzymes (Ribeiro and Horuk, Pharmacology and Therapeutics 107:44-58, 2005). Compound 1 can be linked to an oligonucleotide as shown on Conjugate 2, where R stands for the oligonucleotide, linker and tether. The conjugate with an oligonucleotide is expected to maintain the favorable drug-like properties of both the ligand and oligonucleotide.

CCR5 antagonist 3 (of the piperidine family) showed an $IC_{50}$ value in the sub-nanomolar range for the inhibition of CCL3 and CCL5 binding to Chinese Hamster Ovary (CHO) cells expressing recombinant human CCR5 (Ribeiro and Horuk, Pharmacology and Therapeutics 107:44-58, 2005). The structure for conjugation of Compound 3 with an oligonucleotide is shown as Conjugate 4 in (Table 1).

Compounds 5a and 5b (Table 1) showed $IC_{50}$ values of 38 and <10 nM, respectively, in an assay that measures binding of [$^{125}$I]RANTES (a natural ligand of CCR5) to membranes prepared from CHO cells that stably express recombinant human CCR5 (Burrows et al., org. Med. Chem. Lett. 15:25-28, 2005). Compound 7, a structural variant with a urea linkage, gave an $IC_{50}$ value of 49 nM in a similar assay (Burrows et al., org. Med. Chem. Lett. 15:25-28, 2005). Conjugate 6 represents the structure for conjugation of Compounds 5a and 5b. Conjugate 8 is the conjugate form of the antagonist Compound 7.

Compounds 9a-d (Table 1) inhibited binding of [$^{125}$I] RANTES to CHO cells that express CCR5 with $IC_{50}$ values of 3.4, 1.5, 1.2, and 1.3 nM, respectively (Imamura et al., org. Med. Chem. Lett. 13:397-416, 2005). A conjugate form of Conjugate 10 was designed to attach these highly potent antagonists to oligonucleotides in order to deliver these compounds to cells that express the CCR5 receptor.

A benzimidazole tetrahydroquinoline derivative, Compound 11, another antagonist of CCR5, inhibited HIV-1 NL4.3 or IIIB replication in MT-4 cells with an $EC_{50}$ of 20 μ(Ribeiro and Horuk, Pharmacology and Therapeutics 107: 44-58, 2005). An oligonucleotide-ligand conjugate of this antagonist can be prepared using Conjugate 12 as shown in Table 1.

The spirodiketopiperazine derivative Compound 13 effectively blocked HIV-1 gp120/CCR5 binding ($IC_{50}$=1 nM) and showed potent activity against a wide range of R5 HIV-1 isolates. Pharmacokinetic studies revealed favorable oral bioavailability in rodents. Preliminary phase I clinical studies conducted in 70 healthy volunteers indicated tolerance of dose of 1200 mg following single dose and 800 mg following multiple dosing twice a day. No serious adverse events were reported, although some incidents of QTc prolongation were noted following the administration of the drug in healthy volunteers (Maeda et al., J. Virol. 78:8654-8662, 2004; Ribeiro and Horuk, Pharmacology and Therapeutics 107:44-58, 2005). Conjugate 14 represents the conjugate structure with the desirable properties of the antagonist Compound 13.

Compound 15 inhibited [$^{125}$I]RANTES binding to CCR5-expressing CHO cells with an $IC_{50}$ of 1 nM $IC_{50}$ (Imamura et al., org. Med. Chem. 12:2295-2306, 2004). An oligonucleotide ligand conjugate was designed in which the morpholino moiety of the parent ligand is substituted by a piperazine moiety to link to the oligonucleotide via the second N-atom of the piperazine ring (Compound 16).

Compounds 17a and 17b inhibited [$^{125}$I]RANTES biding to CCR5-expressing CHO cells with $IC_{50}$ values 27 and 3.6 nM, respectively (Seto et al., Chem. Pharm. Bull. 52:577-590, 2004). Conjugate 18 is designed to attach these ligands to oligonucleotides for therapeutic evaluation.

In vitro CCR5 binding assays using membranes prepared from CHO cells transfected with human or cyano CCR5 with Compound 19 against [$^{125}$I]MI-1α showed inhibition with $IC_{50}$ values of 2.6 nM for human and 0.7 nM for cyano CCR5 (Thoma et al., J. Med. Chem. 47:1939-1955, 2004). Two conjugates (Table 1, 20a and 20b) of the ligand 19 with oligonucleotides were designed by changing the site of conjugation on the ligand.

Compound 21 inhibited [$^{125}$I]MIP-1α binding to CCR5 receptor with an $IC_{50}$ of 4.4 nM (Kazmierski et al., Bioorg. Med. Chem. 11:2663-2676, 2003). Compound 21 was been redesigned to allow conjugation to an oligonucleotide. Conjugate building blocks (22a and 22b) were designed and synthesized and conjugated to oligonucleotides (see Conjugate 22c). FIG. 4 depicts a conjugate of Compound 21 with an RNA duplex.

In one embodiment, the CCR5-binding ligand is an immunoglobulin (e.g., an antibody or antibody fragment that binds CCR5 iRNA).

In one embodiment, the iRNA agent is double-stranded, and the CCR5-binding ligand is attached to the 5' end or 3' end of the sense strand of the iRNA agent. In another embodiment, the CCR5-binding ligand is attached to the 5' end or 3' end of the antisense strand of the iRNA agent. In another embodiment, the CCR5-binding ligand is attached to one end of the sense strand of the iRNA agent, and a different moiety (e.g., a lipophilic moiety, such as cholesterol) is conjugated to the other end of the sense strand of the iRNA agent. In another embodiment, the iRNA agent includes a CCR5-binding ligand on each strand of the double-stranded iRNA agent (e.g., on the 5' end of the sense strand and the 5' end of the antisense strand). In yet another embodiment, the iRNA agent is single-stranded, and the CCR5-binding ligand is conjugated to the 5'end or 3'end of the oligonucleotide.

In one embodiment, the iRNA agent is at least 15 nucleotides long and includes a sense RNA strand and an antisense RNA strand, wherein the antisense RNA strand is 30 or fewer nucleotides in length, and the duplex region of the iRNA agent is 15-30, preferably 18-25 nucleotide pairs in length. The iRNA agent may further include a nucleotide overhang having 1 to 4, preferably 2 to 3, unpaired nucleotides, and the unpaired nucleotides may have at least one phosphorothioate dinucleotide linkage. The nucleotide overhang can be at the 3'-end of the antisense strand of the iRNA agent.

In one embodiment, the modified iRNA agent inhibits or reduces expression of a gene expressed in a cell that also expresses CCR5. The gene can be an endogenous gene (e.g., a gene responsible immune cell activation or cell viability) or a gene from an invading pathogen (e.g., a virus or a bacterium). Exemplary CCR5-expressing cells include granulocyte-derived cells, virus-infected cells, bone marrow-derived cells (e.g., lymphocytes, monocytes, macrophages), and/or mononuclear cells In one embodiment, a CCR5-expressing cell is infected with a virus, such as a human immunodeficiency virus (HIV), simian-human immunodeficiency virus (SIV), or hepatits virus (e.g., hepatitis B). For example, a modified iRNA agent that targets a CCR5-expressing cell infected with HIV-1 can target a gene expressed by the HIV-1 virus (e.g., gp120, gp41, Env, TAT). In one exemplary embodiment, the iRNA agent inhibits or reduces expression of the HIV-1 gp120 gene. In another example, a modified iRNA agent that targets a CCR5-expressing cell infected with hepatitis B, targets the hepatitis B virus X protein gene.

In another embodiment, the modified iRNA agent inhibits or reduces expression of a gene expressed in a cell that also expresses CCR5. In one embodiment, a CCR5-expressing cell is infected with a bacterium, such as a *Trypanosoma cruzi, Borrelia burgdorferi, Mycobacterium tuberculosis, Mycobacterium leprae, Mycobacterium avium, Mycobacterium bovis,* or *Helicobacter pylori*, and the iRNA agent conjugated to a CCR5-binding ligand inhibits or reduces expression of a gene expressed by the bacterium.

In another embodiment, it is preferred that the modified iRNA agent be further modified to improve stability. Preferred modifications are phosphorothioate linkages and 2'-substitutions on the ribose unit (e.g., 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA) substitutions).

Preferably, these 2'-substitutions are made to the 5' nucleotide of a 5'-UA-3' dinucleotide, a 5'-UG-3' dinucleotide, a 5'-CA-3' dinucleotide, a 5'-UU-3' dinucleotide, or a 5'-CC-3' dinucleotide on the sense strand and, optionally, also on the antisense strand of the iRNA agent, or to all pyrimidine-base comprising nucleotides. More, preferably, the 5'-most pyrimidines in all occurrences of the sequence motifs 5'-UA-3', 5'-CA-3', 5'-UU-3', and 5'-UG-3' are 2'-modified nucleotides. Yet more preferably, all pyrimidines in the sense strand are 2'-modified nucleotides, and the 5'-most pyrimidines in all occurrences of the sequence motifs 5'-UA-3' and 5'-CA-3' are modified. Most preferably, all pyrimidines in the sense strand are 2'-modified nucleotides, and the 5'-most pyrimidines in all occurrences of the sequence motifs 5'-UA-3', 5'-CA-3', 5'-UU-3', and 5'-UG-3' in the antisense strand are 2'-modified nucleotides.

In another embodiment, a CCR5-binding ligand (e.g., on the 3'-end of the sense strand), a 2'-modification (e.g., a 2'-O-methyl or 2'-deoxy-2'-fluoro-modification), and a phosphorothioate (e.g., on the 3'-most one or two nucleotides of the sense and antisense strands) are present in the same iRNA agent.

In another aspect, the invention features a method of targeting a modified iRNA agent to a cell expressing CCR5. In one embodiment, the method includes administering the modified iRNA agent to a subject, wherein the iRNA agent comprises a CCR5-binding ligand conjugated to at least one strand of the iRNA agent.

In one embodiment, the CCR5-binding molecule is a CCR5 antagonist, such as an antagonist listed in column 1 of Table 1 above. The iRNA agent is double-stranded, and the ligand is attached to the 5' end or the 3' end of the sense strand of the iRNA agent. In another embodiment, the ligand is attached to one end of the sense strand of the iRNA agent by a tether and linker as shown in column II of Table 1.

In another aspect, the invention features a method of treating a human having or at risk for developing a disease or disorder associated with CCR5 gene expression. The method includes administering an iRNA agent conjugated to a CCR5-binding ligand, such that the iRNA agent inhibits or reduces expression of CCR5.

In one embodiment, the human has or is at risk for developing a viral or bacterial infection. For example, the human can be infected with immunodeficiency virus (HIV) or simian-human immunodeficiency virus (SIV). In one embodiment, a CCR5-expressing cell is infected with HIV-1, and the iRNA agent inhibits or reduces expression of a gene expressed by the HIV-1 virus (e.g., gp120, gp41, Env, TAT).

In a preferred embodiment, administration of a modified iRNA agent (e.g., an iRNA agent described herein) is for treatment of a disease or disorder present in the subject wherein the disease effects cells expressing (e.g., overexpressing) CCR5. In another preferred embodiment, administration of the iRNA agent is for prophylactic treatment of a disease or disorder that affects cells expressing CCR5.

In another embodiment, the human has or is at risk for developing a bacterial infection, such as an infection by *Trypanosoma cruzi, Borrelia burgdorferi, Mycobacterium tuberculosis, Mycobacterium leprae, Mycobacterium avium, Mycobacterium bovis,* or *Helicobacter pylori*. In one embodiment, a CCR5-expressing cell is infected with a bacterium, and the iRNA agent conjugated to a CCR5-binding ligand inhibits or reduces expression of a gene expressed by the bacterium.

In one embodiment, the human is at risk for developing an infection (e.g., a viral or bacterial infection) and the iRNA agent modified for enhanced targeting and uptake into CCR5-expressing cells prevents infection. For example, a composition including the modified iRNA agent can be applied intravaginally to prevent transmission of HIV.

In another embodiment, the human has or is at risk for developing an autoimmune disease (e.g., uveitis, Acquired Immune Deficiency Syndrome (AIDS), rheumatoid arthritis, IgA nephropathy, giant cell arteritis, or multiple sclerosis). Administration of an iRNA agent modified for enhanced targeting to CCR5-expressing cells (e.g., by conjugation to a CCR5-binding ligand) targets the iRNA agent to cells particularly affected by the disease. The iRNA agent targets a gene expressed in the CCR5-expressing cell to reduce or relieve one or more symptoms of the disease or disorder.

In another embodiment, the human has or is at risk for developing an inflammatory disease or disorder (e.g., asthma, interstitial lung disease, coronary heart disease, or allergic pulmonary disease). Administration of an iRNA agent modified for enhanced targeting to CCR5-expressing cells (e.g., by conjugation to a CCR5-binding ligand) targets the iRNA agent to cells particularly affected by the disease. The iRNA agent targets a gene expressed in the CCR5-expressing cell to reduce or relieve one or more symptoms of the disease or disorder.

In another aspect, the invention features a method of making an iRNA agent modified for enhanced uptake into CCR5-expressing cells. In one embodiment, the method includes providing (e.g., by synthesizing the iRNA agent) and conjugating a CCR5-binding ligand (e.g., a CCR5-binding antagonist) to at least one end of at least one strand of the iRNA agent.

In another aspect, the invention features preparations, including substantially pure or pharmaceutically acceptable preparations of iRNA agents that are modified for enhanced targeting and uptake by CCR5-expressing cells. The preparations can include an iRNA agent that targets a CCR5-expressing cell and a pharmaceutically acceptable carrier.

The pharmaceutical composition featured in the invention can be administered in an amount sufficient to reduce expression of a target RNA expressed in the CCR5-expressing cell. In one embodiment, the iRNA agent is administered in an amount sufficient to reduce expression of the target RNA (e.g., by at least 10%, 20%, 40%, 60%, or greater).

The pharmaceutical composition featured in the invention can be administered to a subject, wherein the subject is at risk for or is suffering from a disorder characterized by elevated or otherwise unwanted expression of a gene expressed in the CCR5-expressing cell. The modified iRNA agent can be administered to an individual diagnosed with or having the disorder, or at risk for the disorder, to delay onset of the disorder or a symptom. In one embodiment, the modified iRNA agent is administered to an individual diagnosed with or having an HIV-1 infection, or at risk for the disorder to delay onset of the disorder or a symptom. In another embodiment, the modified iRNA targets a gene expressed by HIV-1.

In one aspect the invention features a method of inhibiting expression of an HIV-1 gene (e.g., gp120, gp41, Env, TAT) in a cell of a subject. The method includes administering an effective amount of an iRNA agent to the subject, where the iRNA agent includes (i) a CCR5-binding molecule, and (ii) a sequence that is substantially complementary to a sequence of the HIV- 1 gene.

In a preferred embodiment the composition is suitable for delivery to a cell in vivo (e.g., to a cell in an organism). In another aspect, the iRNA agent is suitable for delivery to a cell in vitro (e.g., to a cell in a cell line).

The iRNA agents can be used in any of the methods described herein (e.g., to target any of the genes described herein or to treat any of the disorders described herein). They can be incorporated into any of the formulations, modes of delivery, delivery modalities, kits or preparations (e.g., pharmaceutical preparations) described herein. For example, a kit includes one or more of the iRNA agents described herein in a sterile container and instructions for use.

In one aspect, the invention features a compound having structure of formula (I):

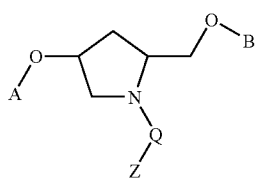

formula (I)

wherein,

A is H, a hydroxyl protecting group, a phosphate group, an activated phosphate group, an activated phosphite group, a phosphoramidite, a solid support, a nucleotide, or an oligonucleotide;

B is H, a hydroxyl protecting group, a phosphate group, an activated phosphate group, an activated phosphate group, a phosphoramidite, a solid support, a nucleotide, or an oligonucleotide;

Z is a CCR5-binding ligand;

Q is —(CH$_2$)$_n$NH—, —C(O)(CH$_2$)$_n$NH—, —(CH$_2$)$_n$ONH—, —C(O)(CH$_2$)$_n$ONH—, —C(O)—(CH$_2$)$_n$—, —(CH$_2$)$_n$NHNH$_2$—, —C(O)(CH$_2$)$_n$NHNH$_2$—, —C(O)—O—, —(CH$_2$)$_n$—C(O)—, —C(O)—NH—, —C(O)—, —C(O)—(CH$_2$)$_n$—C(O)—, —C(O)—(CH$_2$)$_n$—C(O)O—, —C(O)—(CH$_2$)$_n$—NH—C(O)—, —(CH$_2$)$_n$—C(O)O—, —C(O)(CH$_2$)$_n$NHC(O)(CH$_2$)$_m$—, —C(O)(CH$_2$)$_n$NHC(O)(CH$_2$)$_m$NH—, —(CH$_2$)$_n$—NH—C(O)—, or (CH$_2$)$_n$—, n is 1-20; and m is 1-6.

In one embodiment, A is an activated phosphite group, a phosphoramidite, or a solid support.

In one embodiment, B is a hydroxyl protecting group.

In one embodiment, Q is —C(O)(CH$_2$)$_n$NHC(O)(CH$_2$)$_m$NH—, —C(O)(CH$_2$)$_n$NHC(O)(CH$_2$)$_m$—, —C(O)(CH$_2$)$_n$NH—, preferably —C(O)(CH$_2$)$_n$NHC(O)(CH$_2$)$_m$NH—.

In one embodiment, the CCR5-binding ligand is a CCR5 antagonist, for example, an antagonist listed in column 1 of Table 1. In some preferred embodiments, the CCR5 antagonist has the structure # 2 from Table 1, has the structure # 4 from Table 1, has the structure # 6 from Table has the structure # 8 from Table 1, has the structure # 10 from Table 1, has the structure # 12 from Table 1, has the structure # 14 from Table 1, has the structure # 16 from Table 1, has the structure # 18 from Table 1, has the structure # 20a from Table 1, has the structure # 20b from Table 1, or has the structure # 21 from Table 1.

In one embodiment, A is an oligonucleotide, for example a double stranded oligonucleotide.

In one embodiment, B is an oligonucleotide, for example a double stranded oligonucleotide.

In one embodiment, A is an oligonucleotide and B is an oligonucleotide, for example a double stranded nucleotide.

In some preferred embodiments, the invention features a compound having structure of formula (I):

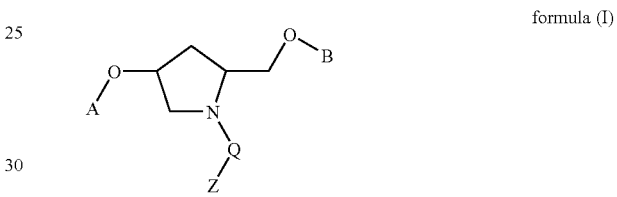

formula (I)

wherein,

A and B are each independently is H, a solid support, a nucleotide, or an oligonucleotide;

Q is —C(O)(CH$_2$)$_n$NHC(O)(CH$_2$)$_m$NH—, n is 1-20 (e.g., 4-10); and m is 1-6.

In some preferred embodiments, at least one of A or B is H or a solid support.

The methods and compositions featured in the invention (e.g., the iRNA agents described herein) can be used in any way described herein. For example, the methods and compositions featured in the invention can be used for the treatment of any disease or disorder described herein, and for the treatment of any subject (e.g., any animal, any mammal, such as any human).

The methods and compositions featured in the invention (e.g., the iRNA agents described herein) can be used with any dosage and/or formulation described herein, as well as with any route of administration described herein.

The details of one or more embodiments featured in the invention are set forth in the accompanying drawings and the description below. Other features and advantages featured in the invention will be apparent from the description and drawings, and from the claims. This application incorporates all cited references, patents, and patent applications by references in their entirety for all purposes.

DESCRIPTION OF DRAWINGS

FIG. 5 is the sequence of human CCR5 (GenBank Accession No. NM_000579).

DETAILED DESCRIPTION

Figure 1:
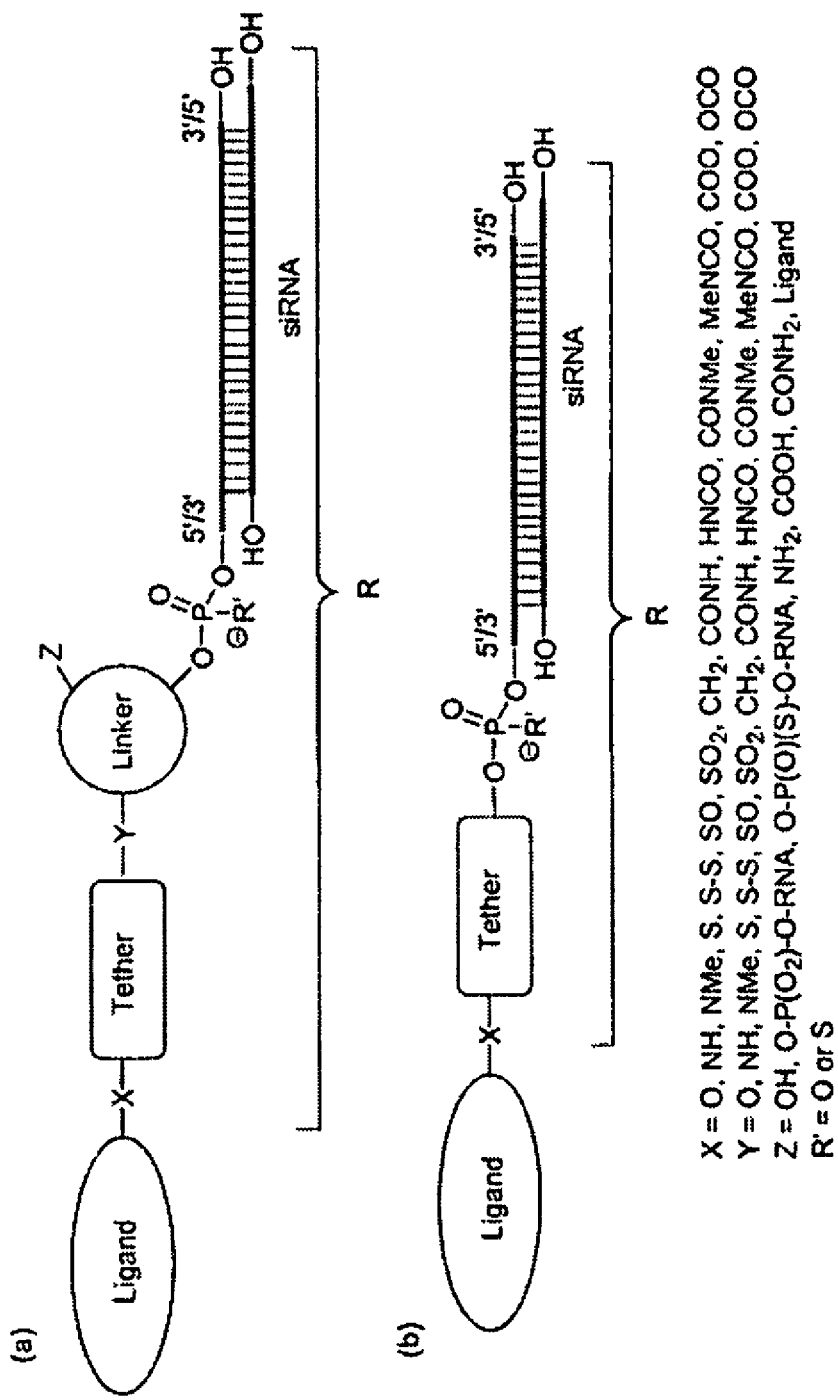
FIG. 1 is a schematic of a ligand-siRNA (double-stranded) conjugate.

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing (e.g., by causing RNA degradation or translation inhibition). While not wishing to be bound by theory, it may be that a molecular signal, which may be merely the specific length of the fragments, present in these 21-23 nt fragments recruits cellular factors that mediate RNAi. Described herein are methods for preparing and administering these 21-23 nt fragments, and other iRNA agents, and their use for specifically inactivating gene function. The use of iRNA agents (or recombinantly produced or chemically synthesized oligonucleotides of the same or similar nature) enables the targeting of specific RNAs for silencing in mammalian cells. In addition, longer dsRNA agent fragments can also be used as described below.

iRNA agents modified for enhanced delivery to CCR5-expressing cells are useful for delivery to a variety of cell types and for the treatment of a variety of diseases and disorders. For example, the modified iRNA agents can be used to target a cell infected by a pathogen, such as a virus or bacteria. In a preferred embodiment, the iRNA agent targets a gene of a pathogen or an endogenous gene, such as a receptor that facilitates infection by the pathogen. Administration of the iRNA agent therefore treats, or prevents, infection. An infection by a pathogen can cause CCR5 expression in the cell, or CCR5 expression may be unrelated to the infection. CCR5-expressing cells can include cells infected by a virus, such as HIV (e.g., HIV-1, or HIV-2) or SIV (e.g., SHIV). CCR5-expressing cells suitable for treatment with the modified iRNA agent featured in the invention can include cells infected with a picornavirus, calicivirus, nodavirus, coronavirus, arterivirus, flavivirus, and togavirus. Examples of picornaviruses include enterovirus (poliovirus 1), rhinovirus (human rhinovirus 1A), hepatovirus (hepatitis A and hepatitis B virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is a representative nodavirus. Coronaviruses include coronavirus (avian infections bronchitis virus) and torovirus (Berne virus). Arterivirus (equine arteritis virus) is a representative arteriviridus. Togaviruses include alphavirus (Sindbis virus) and rubivirus (Rubella virus). Finally, the flaviviruses include flavivirus (Yellow fever virus), pestivirus (bovine diarrhea virus).

iRNA agents modified for enhanced delivery to CCR5-expressing cells are useful for delivery to cells infected with a bacteria (e.g., for treatment of the bacterial infection). CCR5-expressing cells can include cells infected by bacteria, such as *Trypanosoma cruzi, Borrelia burgdorferi, Actinobacillus actinomycetemcomitans, Mycobacterium tuberculosis, Mycobacterium leprae, Mycobacterium avium, Mycobacterium bovis, Yersinia pestis, Listeria monocytogenes, Helicobacter pylori, Haemophilus ducreyi*, and *Chlamydia trachomatis*. The modified iRNA agent can target a bacterial mRNA for degradation, thereby inhibiting bacterial gene expression, and killing the bacterial cell, or can weaken the effect of the bacterial infection on the host subject.

iRNA agents modified for enhanced delivery to CCR5-expressing cells are useful for delivery to cells affected by an autoimmune disease and therefore the iRNA agents featured in the invention can be useful for treating a human having or at risk for developing an autoimmune disorder. For example, the human can have or be at risk for developing (1) a rheumatic disease such as rheumatoid arthritis, systemic lupus erythematosus, Sjögren's syndrome, scleroderma, mixed connective tissue disease, dermatomyositis, polymyositis, Reiter's syndrome or Behcet's disease; (2) type I (insulin-dependent) or type II diabetes mellitus; (3) an autoimmune disease of the thyroid, such as Hashimoto's thyroiditis or Graves' Disease; (4) an autoimmune disease of the central nervous system, such as multiple sclerosis, myasthenia gravis, or encephalomyelitis; (5) a variety of phemphigus, such as phemphigus vulgaris, phemphigus vegetans, phemphigus foliaceus, Senear-Usher syndrome, or Brazilian phemphigus; (6) psoriasis (e.g., psoriasis vulgaris) or atopic dermatitis; (7) inflammatory bowel disease (e.g., ulcerative colitis or Crohn's Disease); and (8) a disorder resulting from an organ, tissue, or cell transplant (e.g., a bone marrow transplant), such as acute or chronic GVHD, or Aplastic Anaemia. The iRNA agents featured in the invention can also be used to treat other autoimmune disorders including, but not limited to endogenous uveitis, nephrotic syndrome, primary biliary cirrhosis, lichen planus, pyoderma gangrenosum, alopecia areata, a Bullous disorder, chronic viral active hepatitis, auto immune chronic active hepatitis, and AIDS. In addition, patients who have received a vascular injury would benefit from the methods described herein.

As used herein, a "subject" refers to a mammalian organism undergoing treatment for a disorder mediated by unwanted target gene expression. The subject can be any mammal, such as a cow, horse, mouse, rat, dog, pig, goat, or a primate. In the preferred embodiment, the subject is a human.

An "RNA agent" as used herein, is an unmodified RNA, modified RNA, or nucleoside surrogates, all of which are described herein or are well known in the RNA synthetic art. While numerous modified RNAs and nucleoside surrogates are described, preferred examples include those that have greater resistance to nuclease degradation than do unmodified RNAs. Preferred examples include those that have a 2' sugar modification, a modification in a single strand overhang, preferably a 3' single strand overhang, or, particularly if single stranded, a 5'-modification that includes one or more phosphate groups or one or more analogs of a phosphate group.

An "iRNA agent" (abbreviation for "interfering RNA agent") as used herein, is an RNA agent that can downregulate the expression of a target gene (e.g., a gene expressed in a cell that also expresses the CCR5 gene). While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand (e.g., a structure that resembles an antisense or microRNA), or can include more than one strand (e.g., it can be a double stranded (ds) iRNA agent, also called an siRNA). If the iRNA agent is a single strand it is particularly preferred that it include a 5' modification that includes one or more phosphate groups or one or more analogs of a phosphate group. A single-stranded iRNA agent is at times referred to herein as an oligonucleotide agent.

A "CCR5 antagonist" can bind a CCR5 receptor or a CCR5 receptor ligand (e.g., a natural ligand, such as CCL3L1, CCL4 and CCL5). A CCR5 antagonist can block or reduce CCR5 receptor activity. For example, a CCR5 antagonist can compete with a natural ligand or a ligand from a pathogen (e.g., HIV-1 gp120) for binding to a CCR5 receptor. "Enhanced targeting to CCR5-expressing cells" means that iRNA agents modified for such enhanced targeting are more likely than an unmodified iRNA agent to bind to and be taken up by a CCR5-expressing cell. For example, the modified iRNA agent is at least 20%, 30%, 50%, 70%, or 80% or more likely to bind to and be taken up by a CCR5-expressing cell than is an unmodified iRNA agent. Preferably, the CCR5-binding ligand is specific for binding to CCR5 (e.g., it binds to a cell that is expressing CCR5 at least 10, $10^2$, $10^3$, or $10^4$ times more than to another similar cell that does not express CCR5. In some embodiments, the CCR5-binding ligand is an antagonist from Table 1.

Targeting

For ease of exposition the formulations, compositions and methods in this section are discussed largely with regard to iRNA agents that are conjugated to a CCR5-targeting ligand and are otherwise unmodified. It should be understood, however, that these formulations, compositions and methods can be practiced with other iRNA agents that are targeted to CCR5-expressing cells.

In a particularly preferred embodiment, an iRNA agent, or a DNA that encodes an iRNA agent, or precursor thereof, is targeted to a cell expressing CCR5. For example, the targeting moiety can be a molecule with a specific affinity for the CCR5 polypeptide. Targeting moieties can include antibodies or antibody fragments directed against CCR5, or a CCR5 ligand or a CCR5-binding portion of a CCR5 ligand. The incorporation of the targeting moiety thereby facilitates delivery of the iRNA agent to cells that express CCR5, such as cells infected with a pathogen (e.g., a viral or bacterial pathogen) or a cell in an inflamed tissue. Exemplary CCR5-targeting moieties include antibodies and the ligands in Table 1. In another example, a liposome or particle or other structure that includes an iRNA agent can also include a targeting moiety that recognizes a CCR5 polypeptide on a target cell.

An iRNA agent modified for enhanced targeting and uptake into CCR5-expressing cells can target a gene expressed in the cell of interest. For example, the modified iRNA agent can target an HIV gene in a CCR5-expressing cell infected with HIV-1. CCR5 is a coreceptor for HIV-1 and has been shown to be expressed in bone marrow-derived cells known to be targets for HIV-1 infection, including a subpopulation of lymphocytes, and monocytes and macrophages in blood, primary and secondary lymphoid organs, and noninflamed tissues. Chronically inflamed tissues in HIV-1-infected patients have also been found to contain an increased number of CCR5-positive mononuclear cells. Thus an iRNA agent modified for enhanced uptake into CCR5-expressing cells can target a gene expressed in an HIV-1-infected cell, such as one of the aforementioned cells. In the case of a cell infected with a pathogen (e.g., a bacterium or virus such as HIV) the iRNA agent can be one that targets a gene of the pathogen or a cellular gene needed for propagation of the pathogen's life cycle (e.g., viral replication). For example, in the case of a cell infected with HIV-1, the modified iRNA agent can target a gene expressed by HIV-1 (e.g., gp120, gp40, TAT, or Env). In other embodiments (e.g., in the case of treating inflammation) the modified iRNA agent can target a gene required for cell viability (e.g., a gene required for cell division) or a gene involved in immune cell activation.

To target a particular tissue or cell type, a modified iRNA agent featured in the invention can include an additional modification that facilitates targeting to the tissue or cell type. For example, an iRNA agent can be targeted to a CCR5-expressing cell of the liver or kidney, a CCR5-expressing cell of the nervous system, or a CCR5-expressing muscle cell. For example, CCR5 expression occurs in livers cells infected with hepatitis B. In one embodiment, an iRNA agent conjugated to a CCR5-binding ligand targets a hepatitis B gene and can include a lipophilic moiety for enhanced targeting to the liver. The lipophilic moiety can be conjugated to the same strand of the iRNA agent as the CCR5-binding ligand or to a different strand. Lipophilic moieties include lipids, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. An iRNA agent can also be targeted to the liver by association with a low-density lipoprotein (LDL), such as lactosylated LDL. Polymeric carriers complexed with sugar residues can also function to target iRNA agents to the liver.

In one embodiment, an iRNA agent modified for enhanced uptake into CCR5-expressing cells can be further conjugated with a serum albumin (SA), such as human serum albumin that can target the iRNA agent to a CCR5-expressing cell in a non-kidney tissue.

Conjugation With Ligands to Promote Entry Into Cells

An iRNA agent modified for enhanced uptake into CCR5-expressing cells can be taken up into a cell through its interaction with the CCR5 receptor. Alternatively, an iRNA agent modified for enhanced uptake into CCR5-expressing cells can be further modified so as to enhance entry into cells through an endocytic or non-endocytic mechanism. A ligand that increases cell permeability can be attached to an iRNA agent in a number of ways, such as by attachment to a sugar replacement-based monomer (SRMS) (e.g., a pyrroline-based SRMS). In one embodiment, a CCR5-binding ligand is attached to one end of the sense strand of an iRNA agent and a ligand that increases cell permeability is attached to the other end of the sense strand of the iRNA agent.

In one embodiment, a modified iRNA agent can be conjugated to a polyarginine that will enhance uptake into a wide range of cell-types expressing CCR5. While not being bound by theory, the enhanced uptake is believed to be by a nonendocytic route. In another embodiment, an oligonucleotide can be conjugated to a guanidium analog of an aminoglycoside to promote cell permeability.

In another embodiment, an iRNA agent modified for enhanced uptake into CCR5-expressing cells can be conjugated with a lipophilic moiety. The lipophilic moiety can be attached at the nitrogen atom of a pyrroline-based SRMS. Examples of lipophilic moieties include cholesterols, lipid, oleyl, retinyl, or cholesteryl residues. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Cholesterol is a particularly preferred example.

The ligand that enhances cell permeability can be attached at the 3' terminus, the 5'terminus, or internally. The ligand can be attached to an SRMS (e.g., a pyrroline-based SRMS) at the 3' terminus, the 5'terminus, or at an internal linkage. The attachment can be direct or through a tethering molecule. Tethers, spacers or linkers discussed herein can be used to attach the moiety to the SRMS.

An iRNA agent to which one or more cell-permeability ligands is conjugated (called an "OA-cell permeability conjugate") can be delivered in vivo to cells of a subject, such as a mammalian subject (e.g., a human or mouse). Alternatively, or in addition, the iRNA agent can be delivered in vitro (e.g., to a cell in a cell line). Cell lines can be, for example, from a vertebrate organism, such as a mammal (e.g., a human or a mouse). Delivery of an OA-cell permeability conjugate to a cell line can be in the absence of other transfection reagents. For example, delivery of an OA-cell permeability conjugate to a cell can be in the absence of, or optionally in the presence of, Lipofectamine™ (Invitrogen, Carlsbad, Calif.), Lipofectamine 2000, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, or Metafectene™ (Biontex, Munich, Germany), or another transfection reagent. Exemplary cell lines can be provided by the American Type Culture Collection (ATCC) (Manassus, Virginia). An OA-cell permeability conjugate can be delivered to a cell line, such as any cell line described herein, to target a specific gene for downregulation.

In one example, an iRNA agent-lipophilic conjugate can be delivered to a primary cell line expressing CCR5 (e.g., a synoviocyte (such as type B), myocyte, keratinocyte, hepatocyte, smooth muscle cell, endothelial cell, or fibroblast cell line).

Sugar Replacement Modification Subunit

An iRNA agent modified for enhanced uptake into CCR5-expressing cells is coupled to a ligand (e.g., a CCR5-binding ligand). The ligand can be attached to the iRNA agent can be through a monomer (e.g., a chemically modified monomer that is integrated into the iRNA agent). In a preferred embodiment, the coupling is by a tether or a linker (or both) as described herein, and the complex has the formula represented by:

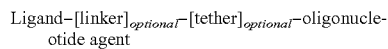
Ligand–[linker]$_{optional}$–[tether]$_{optional}$–oligonucleotide agent While, in most cases, embodiments are described with respect to an iRNA agent that includes a number of nucleotides, the invention includes monomeric subunits having the structure:

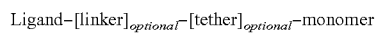
Ligand–[linker]$_{optional}$–[tether]$_{optional}$–monomer

Methods of making and incorporating the monomers into the iRNA agents and methods of using of those agents are included in the invention.

In preferred embodiments, the sugar subunits (e.g., the ribose sugars of one or more of the nucleotides, that can be ribonucleotide, deoxynucleotide, or modified nucleotide) of an iRNA agent can be replaced with another moiety (e.g., a non-carbohydrate (preferably cyclic) carrier). A nucleotide subunit in which the sugar of the subunit has been so replaced is referred to herein as an SRMS. This is often referred to herein as a "tether." A cyclic carrier may be a carbocyclic ring system (i.e., all ring atoms are carbon atoms or a heterocyclic ring system with one or more ring atoms that may be a heteroatom, e.g., nitrogen, oxygen, or sulfur). The cyclic carrier may be a monocyclic ring system, or may contain two or more rings (e.g. fused rings). The cyclic carrier may be a fully saturated ring system or it may contain one or more double bonds.

The carriers further include (i) at least two "backbone attachment points" and (ii) at least one "tethering attachment point." A "backbone attachment point" as used herein refers to a functional group (e.g. a hydroxyl group) or generally, a bond available for, and that is suitable for incorporation of the carrier into the phosphate, or modified phosphate (e.g., sulfur containing) backbone of a ribonucleic acid. A "tethering attachment point" as used herein refers to a constituent ring atom of the cyclic carrier (e.g., a carbon atom or a heteroatom, distinct from an atom which provides a backbone attachment point) that connects a selected moiety. The moiety can be a ligand (e.g., a targeting or delivery moiety) or a moiety that alters a physical property. One of the most preferred moieties is a moiety that targets the iRNA agent to a CCR5-expressing cell (e.g., a ligand that binds CCR5, such as a CCR5 antagonist or anti-CCR5 antibody or anti-CCR5 antibody fragment). Another exemplary moiety that promotes entry into a cell is a lipophilic moiety (e.g., cholesterol). While not wishing to be bound by theory it is believed the attachment of a lipophilic agent increases the lipophilicity of an iRNA agent. Optionally, the selected moiety is connected by an intervening tether to the cyclic carrier. Thus, it will often include a functional group (e.g., an amino group) and will generally provide a bond suitable for incorporation or tethering of another chemical entity (e.g., a ligand) to the constituent ring.

Incorporation of one or more SRMSs described herein into an iRNA agent, particularly when tethered to an appropriate entity, can confer one or more new properties to the iRNA agent and/or alter, enhance, or modulate one or more existing properties in the iRNA agent (e.g., it can alter one or more of cell-targeting properties, lipophilicity, or nuclease resistance). Incorporation of one or more SRMSs described herein into an iRNA agent can, particularly when the SRMS is tethered to an appropriate entity, modulate (e.g., increase) binding affinity of an iRNA agent to a target RNA (e.g., a target RNA expressed in a cell that also expresses CCR5). Incorporation of one or more SRMSs can alter distribution, target the iRNA agent to a particular part of the body, modify the interaction with nucleic acid binding proteins (e.g., during RISC formation and strand separation), or increase sequence specificity (e.g, inhibit off-site targeting).

Accordingly, in one aspect, the invention features, an iRNA agent preferably comprising at least one subunit having the structure of formula (I):

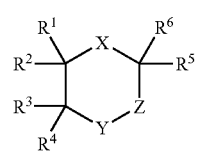

(I)

wherein:
X is N(CO)R$^7$, NR$^7$ or CH$_2$;
Y is NR$^8$, O, S, CR$^9$R$^{10}$, or absent;
Z is CR$^{11}$R$^{12}$ or absent;
Each of R$^1$, R$^2$, R$^3$, R$^4$, R$^9$, and R$^{10}$ is, independently, H, OR$^a$, OR$^b$, (CH$_2$)$_n$OR$^a$, or (CH$_2$)$_n$OR$^b$, provided that at least one of R$^1$, R$^2$, R$^3$, R$^4$, R$^9$, and R$^{10}$ is OR$^a$ or OR$^b$ and that at least one of R$^1$, R$^2$, R$^3$, R$^4$, R$^9$, and R$^{10}$ is (CH$_2$)$_n$OR$^a$, or (CH$_2$)$_n$OR$^b$ (when the SRMS is terminal, one of R$^1$, R$^2$, R$^3$, R$^4$, R$^9$, and R$^{10}$ will include R$^a$ and one will include R$^b$; when the SRMSS is internal, two of $R^1$, $R^2$, $R^3$, $R^4$, $R^9$, and $R^{10}$ will each include an $R^b$); further provided that preferably $OR^a$ may only be present with $(CH_2)_nOR^b$ and $(CH_2)_nOR^a$ may only be present with $OR^b$;

Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;

$R^7$ can be a ligand (e.g., $R^7$ can be $R^d$) or $R^7$ can be a ligand tethered indirectly to the carrier (e.g., through a tethering moiety such as $C_1$-$C_{20}$ alkyl substituted with $NR^cR^d$; or $C_1$-$C_{20}$ alkyl substituted with $NHC(O)R^d$);

$R^8$ is $C_1$-$C_6$ alkyl;
$R^{13}$ is hydroxy, $C_1$-$C_4$ alkoxy, or halo;
$R^{14}$ is $NR^cR^7$;
$R^a$ is:

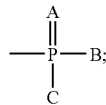

$R^b$ is:

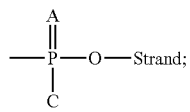

Each of A and C is, independently, O or S;
B is OH, O⁻, or

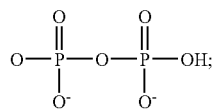

$R^c$ is H or $C_1$-$C_6$ alkyl;
$R^d$ is H or a ligand (e.g., a lipophilic ligand such as cholesterol); and
n is 1-4.

Embodiments can include one or more of the following features:

$R^1$ can be $CH_2OR^a$ and $R^3$ can be $OR^b$; or $R^1$ can be $CH_2OR^a$ and $R^9$ can be $OR^b$; or $R^1$ can be $CH_2OR^a$ and $R^2$ can be $OR^b$.

$R^1$ can be $CH_2OR^b$ and $R^3$ can be $OR^b$; or $R^1$ can be $CH_2OR^b$ and $R^9$ can be $OR^b$; or $R^1$ can be $CH_2OR^b$ and $R^2$ can be $OR^b$; or $R^1$ can be $CH_2OR^b$ and $R^3$ can be $OR^a$; or $R^1$ can be $CH_2OR^b$ and $R^9$ can be $OR^a$; or $R^1$ can be $CH_2OR^b$ and $R^2$ can be $OR^a$.

$R^1$ can be $OR^a$ and $R^3$ can be $CH_2OR^b$; or $R^1$ can be $OR^a$ and $R^9$ can be $CH_2OR^b$; or $R^1$ can be $OR^a$ and $R^2$ can be $CH_2OR^b$.

$R^1$ can be $OR^b$ and $R^3$ can be $CH_2OR^b$; or $R^1$ can be $OR^b$ and $R^9$ can be $CH_2OR^b$; or $R^1$ can be $OR^b$ and $R^2$ can be $CH_2OR^b$; or $R^1$ can be $OR^b$ and $R^3$ can be $CH_2OR^a$; or $R^1$ can be $OR^b$ and $R^9$ can be $CH_2OR^a$; or $R^1$ can be $OR^b$ and $R^2$ can be $CH_2OR^a$.

$R^3$ can be $CH_2OR^a$ and $R^9$ can be $OR^b$; or $R^3$ can be $CH_2OR^a$ and $R^4$ can be $OR^b$.

$R^3$ can be $CH_2OR^b$ and $R^9$ can be $OR^b$; or $R^3$ can be $CH_2OR^b$ and $R^4$ can be $OR^b$; or $R^3$ can be $CH_2OR^b$ and $R^9$ can be $OR^a$; or $R^3$ can be $CH_2OR^b$ and $R^4$ can be $OR^a$.

$R^3$ can be $OR^b$ and $R^9$ can be $CH_2OR^a$; or $R^3$ can be $OR^b$ and $R^4$ can be $CH_2OR^a$; or $R^3$ can be $OR^b$ and $R^9$ can be $CH_2OR^b$; or $R^3$ can be $OR^b$ and $R^4$ can be $CH_2OR^b$.

$R^3$ can be $OR^a$ and $R^9$ can be $CH_2OR^b$; or $R^3$ can be $OR^a$ and $R^4$ can be $CH_2OR^b$.

$R^9$ can be $CH_2OR^a$ and $R^{10}$ can be $OR^b$.

$R^9$ can be $CH_2OR^b$ and $R^{10}$ can be $OR^b$; or $R^9$ can be $CH_2OR^b$ and $R^{10}$ can be $OR^a$.

In a preferred embodiment the ribose is replaced with a pyrroline scaffold or with a 4-hydroxyproline-derived scaffold, and X is $N(CO)R^7$ or $NR^7$, Y is $CR^9R^{10}$, and Z is absent.

$R^1$ and $R^3$ can be cis or $R^1$ and $R^3$ can be trans.
n can be 1.
A can be O or S.
$R^1$ can be $(CH_2)_nOR^b$ and $R^3$ can be $OR^b$; or $R^1$ can be $(CH_2)_nOR^a$ and $R^3$ can be $OR^b$.

$R^7$ can be $(CH_2)_5NHR^d$ or $(CH_2)_5NHR^d$. $R^d$ can be chosen from a folic acid radical, a cholesterol radical, a carbohydrate radical, a vitamin A radical, a vitamin E radical, or a vitamin K radical. Preferably, $R^d$ is a cholesterol radical.

$R^1$ can be $OR^b$ and $R^3$ can be $(CH_2)_nOR^b$; or $R^1$ can be $OR^b$ and $R^3$ can be $(CH_2)_nOR^a$; or $R^1$ can be $OR^a$ and $R^3$ can be $(CH_2)_nOR^b$; or $R^1$ can be $(CH_2)_nOR^b$ and $R^9$ can be $OR^a$.

$R^1$ and $R^9$ can be cis or $R^1$ and $R^9$ can be trans.

$R^1$ can be $OR^a$ and $R^9$ can be $(CH_2)_nOR^b$; or $R^1$ can be $(CH_2)_nOR^b$ and $R^9$ can be $OR^b$; or $R^1$ can be $(CH_2)_nOR^a$ and $R^9$ can be $OR^b$; or $R^1$ can be $OR^b$ and $R^9$ can be $(CH_2)_nOR^b$; or $R^1$ can be $OR^b$ and $R^9$ can be $(CH_2)_nOR^a$.

$R^3$ can be $(CH_2)_nOR^b$ and $R^9$ can be $OR^a$; or $R^3$ can be $(CH_2)_nOR^b$ and $R^9$ can be $OR^b$; or $R^3$ can be $(CH_2)_nOR^a$ and $R^9$ can be $OR^b$; or $R^3$ can be $OR^a$ and $R^9$ can be $(CH_2)_nOR^b$; or $R^3$ can be $OR^b$ and $R^9$ can be $(CH_2)_nOR^b$; or $R^3$ can be $OR^b$ and $R^9$ can be $(CH_2)_nOR^a$.

$R^3$ and $R^9$ can be cis or $R^3$ and $R^9$ can be trans.

In other preferred embodiments the ribose is replaced with a piperidine scaffold, and X is $N(CO)R^7$ or $NR^7$, Y is $CR^9R^{10}$, and Z is $CR^{11}R^{12}$.

$R^9$ can be $(CH_2)_nOR^b$ and $R^{10}$ can be $OR^a$.
n can be 1 or 2.
$R^9$ can be $(CH_2)_nOR^b$ and $R^{10}$ can be $OR^b$; or $R^9$ can be $(CH_2)_nOR^a$ and $R^{10}$ can be $OR^b$.
A can be O or S.
$R^7$ can be $(CH_2)_5NHR^d$ or $(CH_2)_5NHR^d$. $R^d$ can be selected from a folic acid radical, a cholesterol radical, a carbohydrate radical, a vitamin A radical, a vitamin E radical, or a vitamin K radical. Preferably, $R^d$ is a cholesterol radical.

$R^3$ can be $(CH_2)_nOR^b$ and $R^4$ can be $OR^a$; or $R^3$ can be $(CH_2)_nOR^b$ and $R^4$ can be $OR^b$; or
$R^3$ can be $(CH_2)_nOR^a$ and $R^4$ can be $OR^b$.

$R^1$ can be $(CH_2)_nOR^b$ and $R^2$ can be $OR^a$; or $R^1$ can be $(CH_2)_nOR^b$ and $R^2$ can be $OR^b$; or $R^1$ can be $(CH_2)_nOR^a$ and $R^2$ can be $OR^b$.

$R^3$ can be $(CH_2)_nOR^b$ and $R^9$ can be $OR^a$.
$R^3$ and $R^9$ can be cis, or $R^3$ and $R^9$ can be trans.
$R^3$ can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^a$ and $R^9$ can be $OR^b$.

$R^1$ can be $(CH_2)_nOR^b$ and $R^3$ can be $OR^a$.
$R^1$ and $R^3$ can be cis, or $R^1$ and $R^3$ can be trans.
$R^3$ can be $OR^a$ and $R^9$ can be $(CH_2)_nOR^b$.
$R^1$ can be $OR^a$ and $R^3$ can be $(CH_2)_nOR^b$.

In other preferred embodiments the ribose is replaced with a piperazine scaffold, and X is $N(CO)R^7$ or $NR^7$ Y is $NR^8$, and Z is $CR^{11}R^{12}$.

$R^1$ can be $(CH_2)_nOR^b$ and $R^3$ can be $OR^a$.

$R^1$ and $R^3$ can be cis or $R^1$ and $R^3$ can be trans.

n can be 1.

R can be $(CH_2)_nOR^b$ and $R^3$ can be $OR^b$; or $R^1$ can be $(CH_2)_nOR^a$ and $R^3$ can be $OR^b$.

A can be O or S, preferably S.

$R^7$ can be $(CH_2)_5NHR^d$ or $(CH_2)_5NHR^d$. $R^d$ can be chosen from the group of a folic acid radical, a cholesterol radical, a carbohydrate radical, a vitamin A radical, a vitamin E radical, or a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a morpholino scaffold, and X is $N(CO)R^7$ or $NR^7$, Y is O, and Z is $CR^{11}R^{12}$.

$R^1$ can be $(CH_2)_nOR^b$ and $R^3$ can be $OR^a$.

$R^1$ and $R^3$ can be cis, or $R^1$ and $R^3$ can be trans. n can be 1.

$R^1$ can be $(CH_2)_nOR^b$ and $R^3$ can be $OR^b$; of $R^1$ can be $(CH_2)_nOR^a$ and $R^3$ can be $OR^b$.

A can be O or S.

$R^7$ can be $(CH_2)_5NHR^d$ or $(CH_2)_5NHR$. $R^d$ can be chosen from the group of a folic acid radical, a cholesterol radical, a carbohydrate radical, a vitamin A radical, a vitamin E radical, or a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a decalin scaffold, and X is $CH_2$; Y is $CR^9R^{10}$; and Z is $CR^{11}R^{12}$; and $R^5$ and $R^{11}$ together are $C^6$ cycloalkyl.

$R^6$ can be $C(O)NHR^7$.

$R^{12}$ can be hydrogen.

$R^6$ and $R^{12}$ can be trans.

$R^3$ can be $OR^a$ and $R^9$ can be $(CH_2)_nOR^b$.

$R^3$ and $R^9$ can be cis, or $R^3$ and $R^9$ can be trans.

n can be 1 or 2.

$R^3$ can be $OR^b$ and $R^9$ can be $(CH_2)_nOR^b$; or $R^3$ can be $OR^b$ and $R^9$ can be $(CH_2)_nOR^a$.

A can be O or S.

$R^7$ can be $(CH_2)_5NHR^d$ or $(CH_2)_5NHR^d$. $R^d$ can be chosen from the group of a folic acid radical, a cholesterol radical, a carbohydrate radical, a vitamin A radical, a vitamin E radical, or a vitamin K radical. Preferably, $R^d$ is a cholesterol radical.

In other preferred embodiments the ribose is replaced with a decalin/indane scaffold (e.g., X is $CH_2$); Y is $CR^9R^{10}$; and Z is $CR^{11}R^{12}$; and $R^5$ and $R^{11}$ together are $C^5$ cycloalkyl.

$R^6$ can be $CH_3$.

$R^{12}$ can be hydrogen.

$R^6$ and $R^{12}$ can be trans.

$R^3$ can be $OR^a$ and $R^9$ can be $(CH_2)_nOR^a$.

$R^3$ and $R^9$ can be cis, or $R^3$ and $R^9$ can be trans.

n can be 1 or 2.

$R^3$ can be $OR^b$ and $R^9$ can be $(CH_2)_nOR^a$; or $R^3$ can be $OR^b$ and $R^9$ can be $(CH_2)_nOR^a$.

A can be O or S.

$R^{14}$ can be $N(CH3)R^7$. $R^7$ can be $(CH_2)_5NHR^d$ or $(CH_2)_5NHR^d$. $R^d$ can be chosen from the group of a folic acid radical, a cholesterol radical, a carbohydrate radical, a vitamin A radical, a vitamin E radical, or a vitamin K radical. Preferably, $R^d$ is a cholesterol radical.

In another aspect, this invention features an iRNA agent comprising at least one subunit having a structure of formula (II):

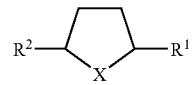

(II)

X is $N(CO)R^7$ or $NR^7$;

Each of $R^1$ and $R^2$ is, independently, $OR^a$, $OR^b$, $(CH_2)_nOR^a$, or $(CH_2)_nOR^b$, provided that one of $R^1$ and $R^2$ is $OR^a$ or $OR^b$ and the other is $(CH_2)_nOR^a$ or $(CH_2)_nOR^b$ (when the SRMS is terminal, one of $R^1$ or $R^2$ will include $R^a$ and one will include $R^b$; when the SRMSS is internal, both $R^1$ and $R^2$ will each include an $R^b$); further provided that preferably $OR^a$ may only be present with $(CH_2)_nOR^b$ and $(CH_2)_nOR^a$ may only be present with $OR^b$;

$R^7$ is $C_1$-$C_{20}$ alkyl substituted with $NR^cR^d$;

$R^8$ is $C_1$-$C_6$ alkyl;

$R^{13}$ is hydroxy, $C_1$-$C_4$ alkoxy, or halo;

$R^{14}$ is $NR^cR^7$;

$R^a$ is:

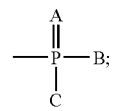

$R^b$ is

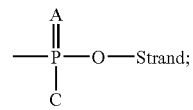

Each of A and C is, independently, O or S;

B is OH, O⁻, or

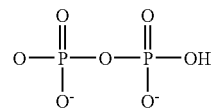

$R^c$ is H or $C_1$-$C_6$ alkyl;

$R^d$ is H or a ligand; and n is 1-4.

Embodiments can include one or more of the features described above.

In a further aspect, this invention features an iRNA agent having a first strand and a second strand, such that at least one subunit having a formula (I) or formula (II) is incorporated into at least one of said strands, and at least one CCR5-binding ligand is conjugated to one end of the first and/or second strand.

In another aspect, this invention features an iRNA agent having a first strand and a second strand, such that at least two subunits having a formula (I) and/or formula (II) are incorporated into at least one of said strands, and at least one CCR5-binding ligand is conjugated to one end of the first and/or second strand.

In another aspect, this invention provides a method of making an iRNA agent described herein having at least one subunit of formula (I) and/or (II), and at least one CCR5-binding ligand is conjugated to one end of the first and/or second strand.

SRMSs or tethers described herein may be incorporated into any iRNA agent described herein. An iRNA agent may include one or more of the SRMSs described herein. An SRMS can be introduced at one or more points in an iRNA agent. An SRMS can be placed at or near (within 1, 2, or 3 positions of) the 3' or 5' end of the oligonucleotide. In some embodiments, it is preferred to not have an SRMS at or near (within 1, 2, or 3 positions of) the 5' end of the oligonucleotide. An SRMS can be internal, and will preferably be positioned in regions not critical for binding to the target. In some embodiments, an iRNA agent has an SRMS at the 3' end and an SRMS at an internal position.

Other modifications to sugars, bases, or backbones described herein can be incorporated into the iRNA agents.

In a preferred embodiment, the iRNA agent has an architecture (architecture refers to one or more of the overall length) described herein.

In another aspect, the invention features an iRNA agent that is conjugated a CCR5-binding ligand (e.g., by conjugation to an SRMS of an iRNA agent). In a preferred embodiment, the CCR5-binding ligand enhances targeting of the iRNA agent to a cell expressing CCR5 (e.g., a cell infected with HIV-1). In a preferred embodiment, the cell is part of an organism, tissue, or cell line (e.g., a primary cell line, immortalized cell line, or any type of cell line disclosed herein). Thus, the conjugated iRNA agent can be used to inhibit expression of a target gene in an organism (e.g., a mammal such as a human) or to inhibit expression of a target gene in a cell line or in cells that are outside an organism.

Tethers

In certain embodiments, a ligand (e.g., a CCR5-binding ligand) may be connected indirectly to a carrier subunit via a tether. Tethers are connected to the carrier at a tethering attachment point (TAP) and may include any $C_1$-$C_{100}$ carbon-containing moiety, (e.g. $C_1$-$C_{75}$, $C_1$-$C_{50}$, $C_1$-$C_{20}$, $C_1$-$C_{10}$; $C_1$, $C_2$, $C_3$, $C_4$, $C_5$, $C_6$, $C_7$, $C_8$, $C_9$, or $C_{10}$), preferably having at least one nitrogen atom. In preferred embodiments, the nitrogen atom forms part of a terminal amino or amido (NHC(O)—) group on the tether and may serve as a connection point for the ligand. Preferred tethers (underlined) include TAP-$(CH_2)_n$NH-; TAP-C(O)$(CH_2)_n$NH-; TAP-NR""$(CH_2)_n$NH-, TAP-C(O)—$(CH_2)_n$—C(O)—; TAP-C(O)—$(CH_2)_n$—C(O)O—; TAP-C(O)—O—; TAP-C(O)—$(CH_2)_n$—NH—C(O)—; TAP-C(O)—$(CH_2)_n$—; TAP-C(O)—NH—; TAP-C(O)—; TAP-$(CH_2)_n$—C(O)—; TAP-$(CH_2)_n$—C(O)O—; TAP-$(CH_2)_n$—; or TAP-$(CH_2)_n$—NH—C(O)—; in which n is 1-20 (e.g., 1, 2, 3, 4, 5, 6, 7, 8, 9, 10, 11, 12, 13, 14, 15, 16, 17, 18, 19, or 20) and R"" is $C_1$-$C_6$ alkyl. Preferably, n is 5, 6, or 11. In other embodiments, the nitrogen may form part of a terminal oxyamino group (i.e., -ONH$_2$) or hydrazino group, (i.e., —NHNH$_2$). The tether may optionally be substituted (e.g., with hydroxy, alkoxy, perhaloalkyl) and/or optionally inserted with one or more additional heteroatoms (e.g., N, O, or S). Preferred tethered ligands may include TAP-$(CH_2)_n$NH(LIGAND); TAP-C(O)$(CH_2)_n$NH(LIGAND); TAP-NR""$(CH_2)_n$NH(LIGAND); TAP-$(CH_2)_n$ONH(LIGAND); TAP-C(O)$(CH_2)_n$ONH(LIGAND); TAP-NR""$(CH_2)_n$ONH(LIGAND); TAP-$(CH_2)_n$NHNH$_2$(LIGAND), TAP-C(O)$(CH_2)_n$NHNH$_2$(LIGAND); TAP-NR""$(CH_2)_n$NHNH$_2$(LIGAND); TAP-C(O)—$(CH_2)_n$—C(O)(LIGAND); TAP-C(O)—$(CH_2)_n$—C(O)O(LIGAND); TAP-C(O)—O(LIGAND); TAP-C(O)—$(CH_2)_n$—NH—C(O)(LIGAND); TAP-C(O)—$(CH_2)_n$(LIGAND); TAP-C(O)—NH(LIGAND); TAP-C(O)(LIGAND); TAP-$(CH_2)_n$-C(O) (LIGAND); TAP-$(CH_2)_n$—C(O)O(LIGAND); TAP-$(CH_2)_n$(LIGAND); or TAP-$(CH_2)_n$—NH—C(O)(LIGAND). In some embodiments, amino terminated tethers (e.g., NH$_2$, ONH$_2$, NH$_2$NH$_2$) can form an imino bond (i.e., C=N) with the ligand. In some embodiments, amino terminated tethers (e.g., NH$_2$, ONH$_2$, NH$_2$NH$_2$) can acylated (e.g., with C(O)CF$_3$).

In some embodiments, the tether can terminate with a mercapto group (i.e., SH) or an olefin (e.g., CH=CH$_2$). For example, the tether can be TAP—$(CH_2)_n$—SH, TAP-C(O)$(CH_2)_n$SH, TAP-$(CH_2)_n$—(CH=CH$_2$), or TAP-C(O)$(CH_2)_n$(CH=CH$_2$), in which n can be as described elsewhere. In certain embodiments, the olefin can be a Diels-Alder diene or dienophile. The tether may optionally be substituted (e.g., with hydroxy, alkoxy, perhaloalkyl) and/or optionally inserted with one or more additional heteroatoms (e.g., N, O, or S). The double bond can be cis or trans or E or Z.

In other embodiments the tether may include an electrophilic moiety, preferably at the terminal position of the tether. Preferred electrophilic moieties include an aldehyde, alkyl halide, mesylate, tosylate, nosylate, brosylate, or an activated carboxylic acid ester (e.g. an NHS ester or a pentafluorophenyl ester). Preferred tethers (underlined) include TAP-$(CH_2)_n$CHO; TAP-C(O)$(CH_2)_n$CHO; or TAP-NR""$(CH_2)_n$CHO, in which n is 1-6 and R"" is $C_1$-$C_6$ alkyl; or TAP-$(CH_2)_n$C(O)ONHS; TAP-C(O)$(CH_2)_n$C(O)ONHS; or TAP-NR""$(CH_2)_n$C(O)ONHS, in which n is 1-6 and R"" is $C_1$-$C_6$ alkyl; TAP-$(CH_2)_n$C(O)OC$_6$F$_5$; TAP-C(O)$(CH_2)_n$C(O)OC$_6$F$_5$; or TAP-NR""$(CH_2)_n$C(O)OC$_6$F$_5$, in which n is 1-11 and R"" is $C_1$-$C_6$ alkyl; or —$(CH_2)_n$CH$_2$LG; TAP-C(O)$(CH_2)_n$CH$_2$LG; or TAP-NR""$(CH_2)_n$CH$_2$LG, in which n can be as described elsewhere and R"" is $C_1$-$C_6$ alkyl (LG can be a leaving group, e.g., halide, mesylate, tosylate, nosylate, brosylate). Tethering can be carried out by coupling a nucleophilic group of a ligand (e.g., a thiol or amino group) with an electrophilic group on the tether.

In other embodiments, it can be desirable for the ligand-conjugated monomer or a ligand-conjugated monomer to include a phthalimido group (K) at the terminal position of the tether.

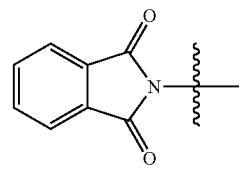

K

In other embodiments, other protected amino groups can be at the terminal position of the tether, including alloc, monomethoxy trityl (MMT), trifluoroacetyl, Fmoc, or aryl sulfonyl (e.g., the aryl portion can be ortho-nitrophenyl or ortho, para-dinitrophenyl).

Any of the tethers described herein may further include one or more additional linking groups, including —O—(CH$_2$)$_n$—, —(CH$_2$)$_n$—SS—, —(CH$_2$)$_n$—, or —(CH=CH)—.

Tethered Ligands

An iRNA agent modified for enhanced targeting and uptake into CCR5-expressing cells can include tethered ligands in addition to the conjugated CCR5-binding ligand. The properties of an iRNA agent, including its pharmacological properties, can be influenced and tailored by the introduction of ligands (e.g., tethered ligands) including ligands that bind CCR5.

A wide variety of entities (e.g., ligands) can be tethered to an iRNA agent (e.g., to the carrier of a ligand-conjugated monomer subunit). Examples are described below in the context of a ligand-conjugated monomer subunit but entities can be coupled at other points to an iRNA agent.

Preferred moieties are ligands, including CCR5-binding ligands that are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having an amino-terminated tether (e.g., $TAP-(CH_2)_nNH_2$) may be incorporated into the growing strand. In a subsequent operation (i.e., after incorporation of the precursor monomer subunit into the strand) a ligand having an electrophilic group (e.g., a pentafluorophenyl ester or aldehyde group) can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target (e.g., molecule, cell or cell type, or a compartment such as a cellular or organ compartment, tissue, organ or region of the body) as compared to a species absent such a ligand. In a much preferred embodiment, the ligand is a CCR5-targeting ligand that provides an enhanced affinity of the modified iRNA agent for a cell expressing CCR5, such as a cell infected with HIV-1.

Additional ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in addition to the CCR5-binding ligand can include therapeutic modifiers (e.g., for enhancing uptake), diagnostic compounds or reporter groups (e.g., for monitoring distribution), cross-linking agents, nuclease-resistance conferring moieties, and natural or unusual nucleobases. General examples include lipophilic molecules, lipids, lectins, steroids (e.g., uvaol, hecigenin, diosgenin), terpenes (e.g., triterpenes like sarsasapogenin, Friedelin, epifriedelanol-derivatized lithocholic acid), vitamins, carbohydrates (e.g., a dextran, pullulan, chitin, chitosan, inulin, cyclodextrin, or hyaluronic acid), proteins, protein binding agents, integrin targeting molecules, polycationics, peptides, polyamines, and peptide mimics.

A ligand may be a naturally occurring or recombinant or synthetic molecule, such as a synthetic polymer (e.g., a synthetic polyamino acid). Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include polyethylenimine, polylysine (PLL), spermine, spermidine, polyamine, pseudopeptide-polyamine, peptidomimetic polyamine, dendrimer polyamine, arginine, amidine, protamine, cationic moieties (e.g., cationic lipid, cationic porphyrin, quaternary salt of a polyamine), or an alpha helical peptide. In one embodiment, the iRNA agent is conjugated to a CCR5 single chain antibody-protamine fusion protein.

Ligands can be proteins (e.g., glycoproteins, lipoproteins such as low density lipoprotein (LDL), or albumins such as human serum albumin (HSA)) or peptides (e.g., amino acid segments having a specific affinity for a co-ligand) or antibodies (e.g., an antibody that binds to a specified cell type such as a cancer cell, endothelial cell, or bone cell, and in particular a cell that expresses CCR5). Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose.

A ligand can be a substance (e.g, a drug) that can increase the uptake of the iRNA agent into the cell, for example, by disrupting the cell's cytoskeleton (e.g., by disrupting the cell's microtubules, microfilaments, and/or intermediate filaments). The drug can be, for example, taxon, vincristine, vinblastine, cytochalasin, nocodazole, japlakinolide, latrunculin A, phalloidin, swinholide A, indanocine, or myoservin.

A ligand can be a lipid or lipid-based molecule. Such a lipid or lipid-based molecule preferably binds a serum protein (e.g., human serum albumin). An HSA binding ligand allows for distribution of the conjugate to a target tissue (e.g., liver tissue, including parenchymal cells of the liver). Other molecules that can bind HSA can also be used as ligands. For example, neproxin or aspirin can be used. A lipid or lipid-based ligand can (i) increase resistance to degradation of the conjugate, (ii) increase targeting or transport into a target cell or cell membrane (e.g., a target cell expressing CCR5), and/or (iii) can be used to adjust binding to a serum protein (e.g., HSA).

A lipid-based ligand can be used to modulate (e.g., control the binding) of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

A ligand can be a cell-permeation agent, such as a helical cell-permeation agent (e.g., an amphipathic agent). An exemplary agent is a peptide such as tat or antennapedia. If the agent is a peptide, it can be modified through use of peptidylmimetic, invertomers, non-peptide or pseudo-peptide linkages, and use of D-amino acids. The helical agent is preferably an alpha-helical agent that preferably has a lipophilic and a lipophobic phase.

iRNA Production

An iRNA agent modified for enhanced delivery and uptake into a CCR5-expressing cell can be produced (e.g., in bulk) by a variety of methods. Exemplary methods include organic synthesis and RNA cleavage (e.g., in vitro cleavage).

Organic Synthesis. An iRNA can be made by separately synthesizing each respective strand of a double-stranded RNA molecule. The component strands can then be annealed.

A large bioreactor (e.g., the OligoPilot II from Pharmacia Biotec AB, Uppsala Sweden) can be used to produce a large amount of a particular RNA strand for a given iRNA. The OligoPilot II reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed after release from the solid support and deprotection.

Organic synthesis can be used to produce a discrete iRNA species. The complementary of the species to a particular target gene can be precisely specified. For example, the species may be complementary to a region that includes a polymorphism (e.g., a single nucleotide polymorphism). Further the location of the polymorphism can be precisely defined. In some embodiments, the site complementary to the polymorphism is located in an internal region (e.g., at least 4, 5, 7, or 9 nucleotides from one or both of the termini).

dsRNA Cleavage. iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from Drosophila or using purified components (e.g. a purified RNAse III or RNA-induced silencing complex, RISC). See Ketting et al. *Genes Dev* 2001 October 15;15(20): 2654-9 and Hammond *Science* 2001 August 10;293(5532): 1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

In one embodiment, an iRNA agent modified for enhanced targeting to CCR5-expressing cells is synthesized using phosphoramidite technology on solid-phase support. Synthesis can be performed on solid supports made of controlled pore glass or polystyrene. RNA phosphoramidites, 5'-O-dimethoxytrityl-N6-(t-butylphenoxyacetyl)-2'-O-t-butyldimethylsilyl-adenosine-3'-O-(2-cyanoethyl-N,N-diisopropylamino) phosphoramidite, 5'-O-dimethoxytrityl-N4-(t-butylphenoxyacetyl)-2'-O-t-butyldimethylsilyl-cytidine-3'-O-(2-cyanoethyl-N,N-diisopropylamino) phosphoramidite, 5'-O-dimethoxytrityl-N2-(t-butylphenoxyacetyl)-2'-O-t-butyldimethylsilyl-guanosine-3'-O-(2-cyanoethyl-N,N-diisopropylamino) phosphoramidite, and 5'-0-dimethoxytrityl-2'-O-t-butyldimethylsilyl-uridine-3'-O-(2-cyanoethyl-N,N-diisopropylamino) phosphoramidite, can be purchased. 2'-O-Methyl-ribonucleoside phosphoramidites carry the same protecting groups as the RNA phosphoramidites with the exception of 2'-O-methyl-guanosine, which is N2 isobutyryl protected. Standard capping reagents can be used.

After solid-phase synthesis, the RNA can be cleaved from the support and stored.

Exemplary synthesis schemes follow. The monomers shown here are incorporated using standard RNA protocols.

Scheme 1ª

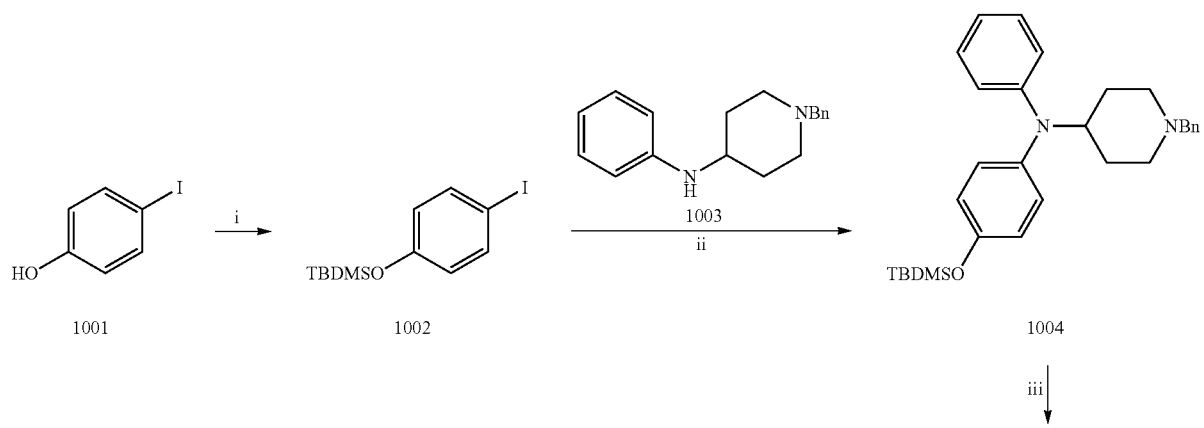

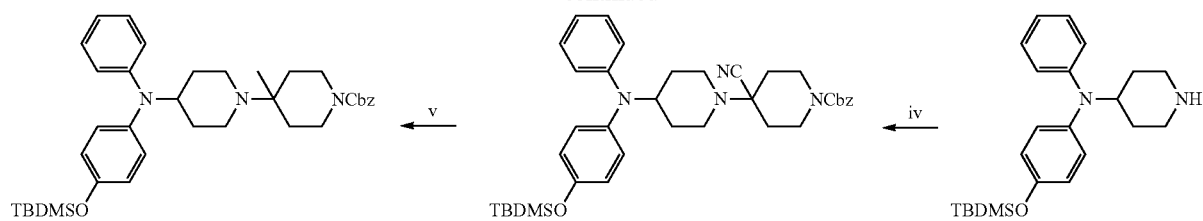
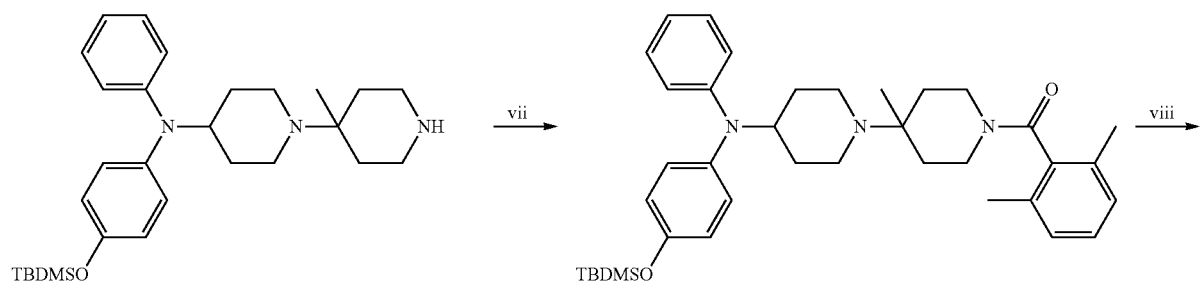
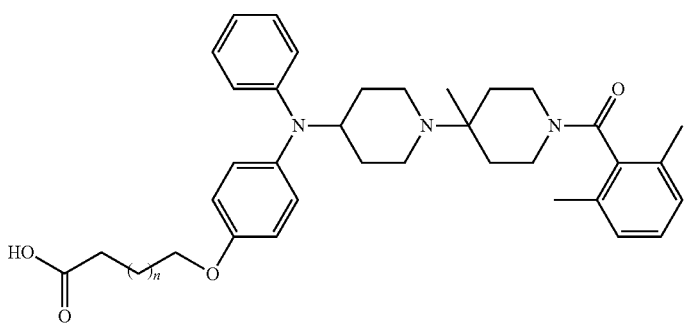

-continued

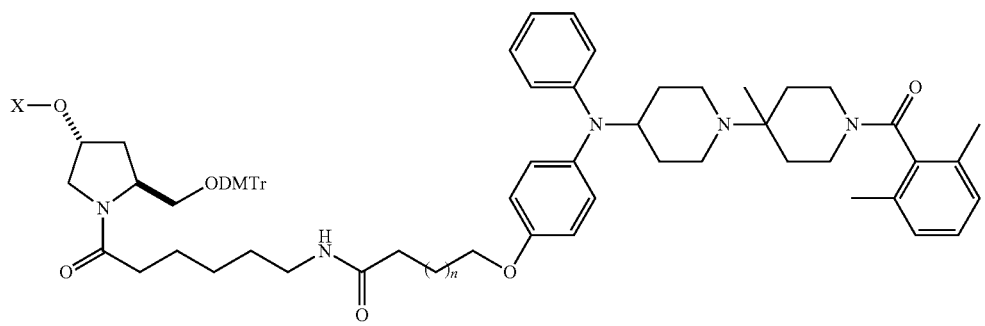

1012
X = Amidite or CPG
n = 1-15

<sup>a</sup>(i) TBDMS-Cl, imidazole/MeCN; (ii) Pd(OAc)₂, BINAP, KOtBu/toluene; (iii) H₂, Pd-C/EtOAc; (iv) 1-Cbz-4-piperidone, Ti(O-iPr)₄/CH₂Cl₂, then add Et₂AlCN; (v) MeMgBr (excess)/THF; (vi) H₂, Pd-C/EtOAc; (vii) amide coupling; (viii) TBAF/THF; (ix) (a) methyl(ethyl) ω-hydroxycarboxylate, Ph₃P, DIAD/MeCN; (b) LiOH/THF-H₂O; (x) (a) peptide coupling; (b) phosphitylation or conjugation to CPG.

Scheme 2ᵃ

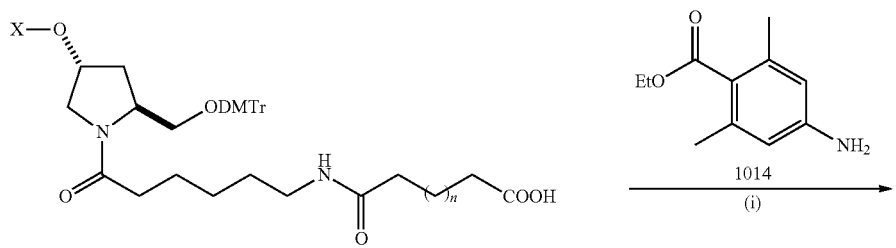

X = TBDMS and n = 1-15
1013

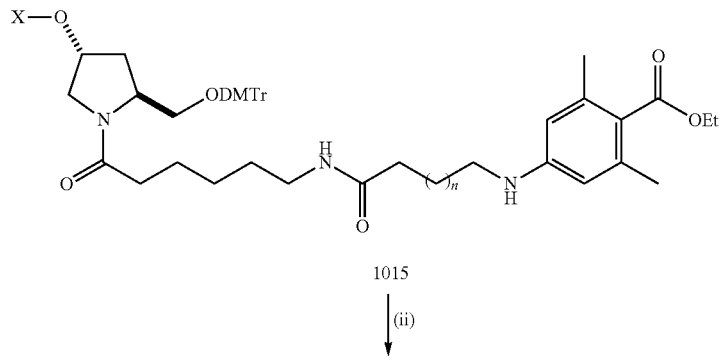

1015

(ii)

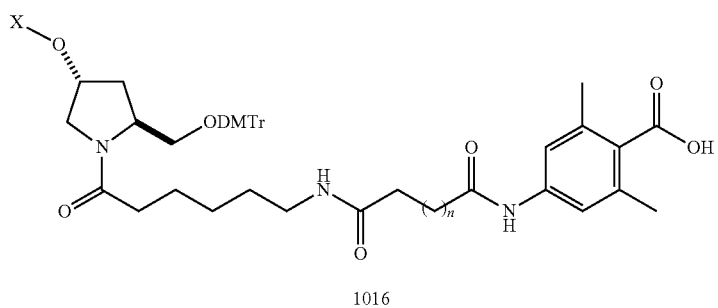

1016

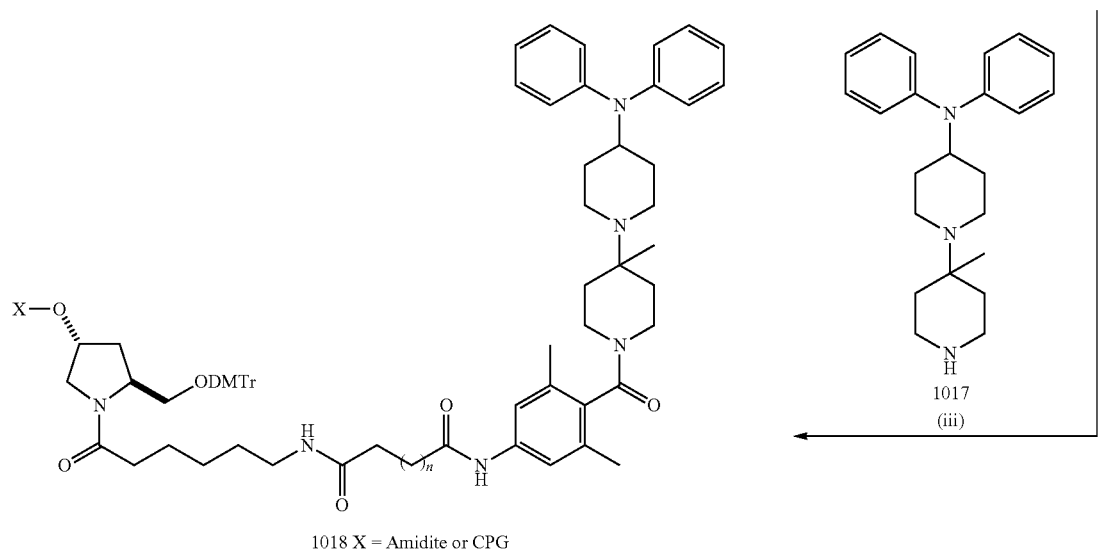
Scheme 3[a]
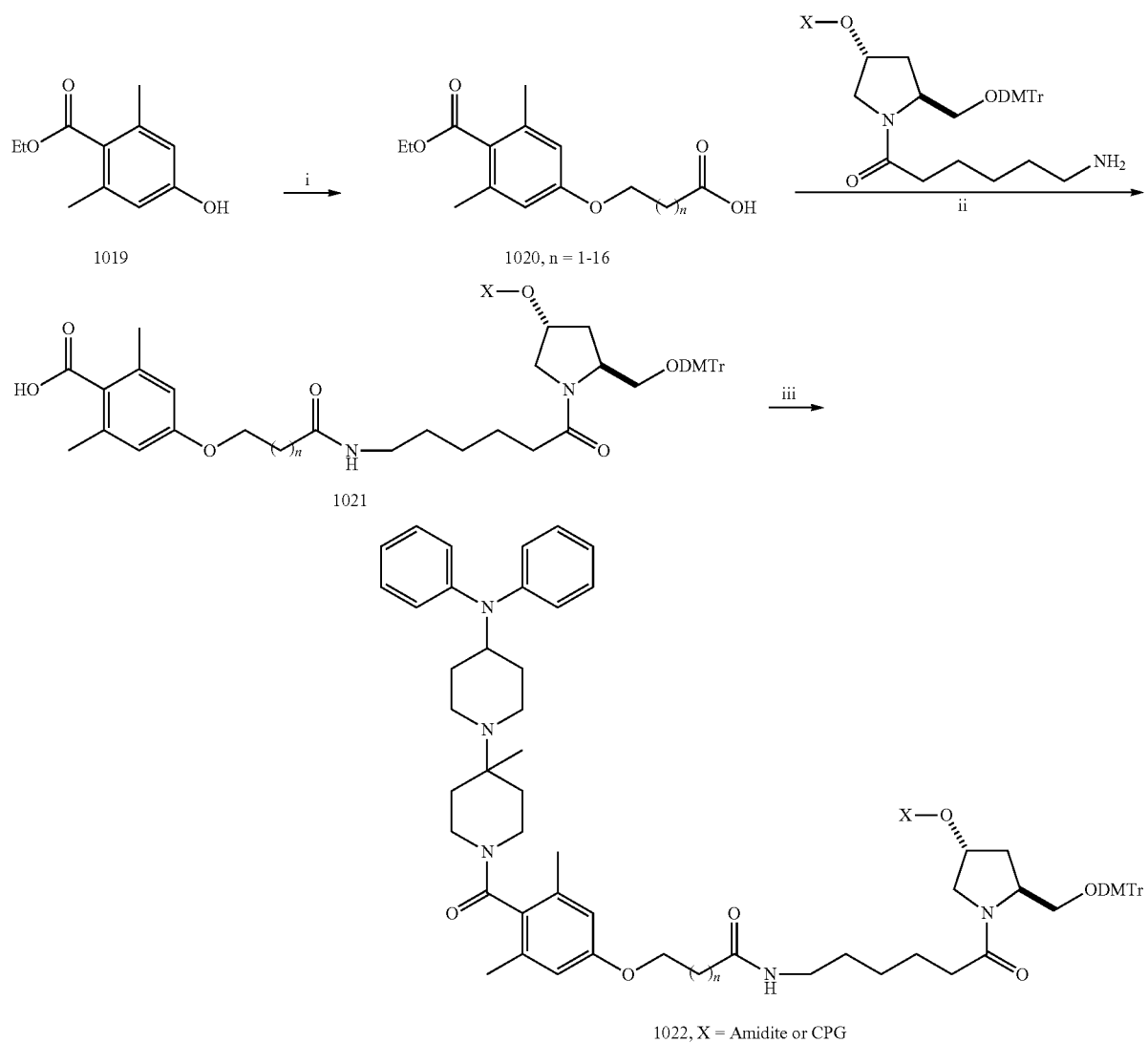

-continued
Scheme 4[a]
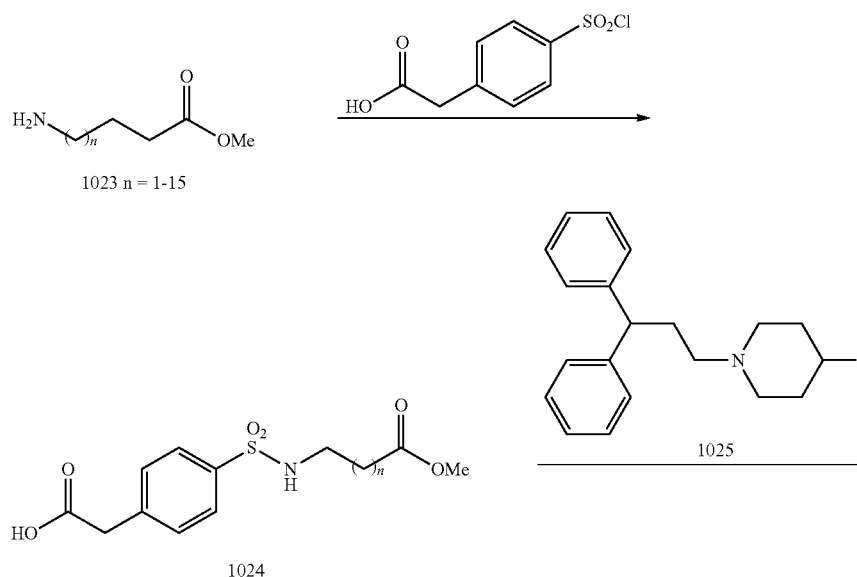
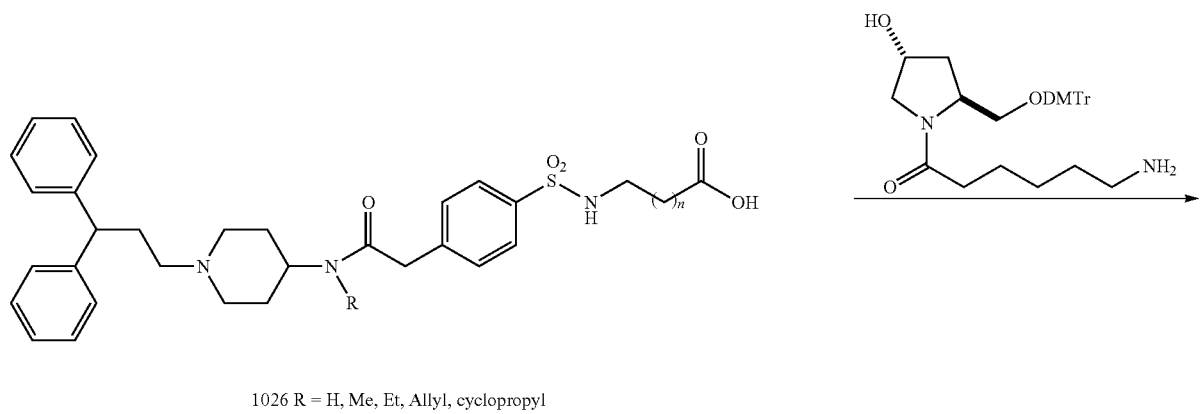
1026 R = H, Me, Et, Allyl, cyclopropyl
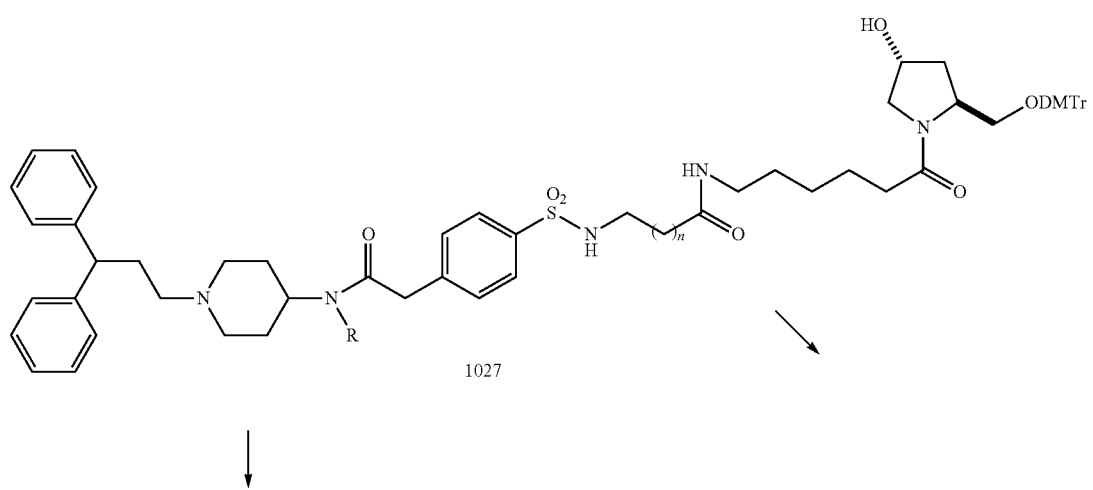
1027

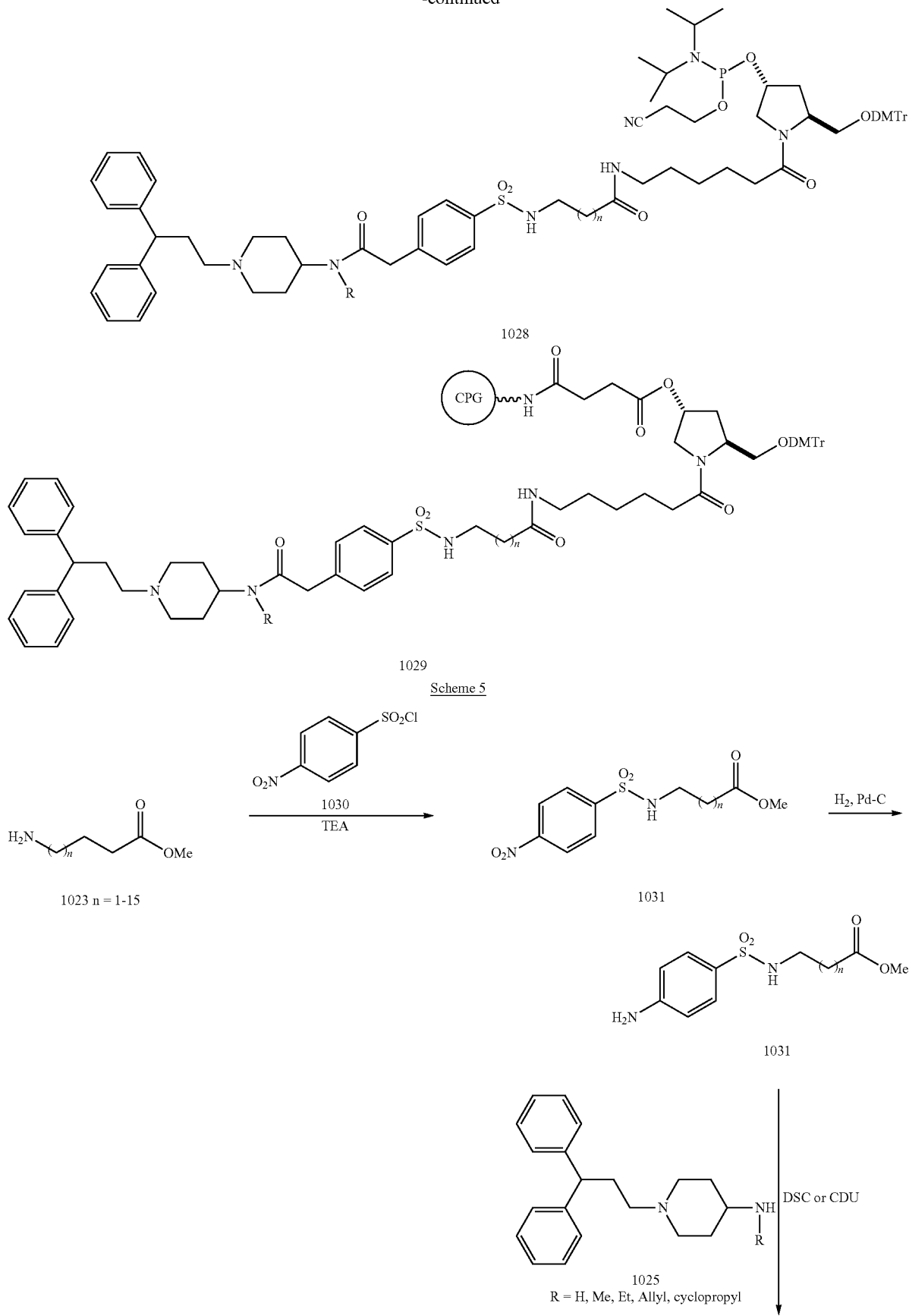

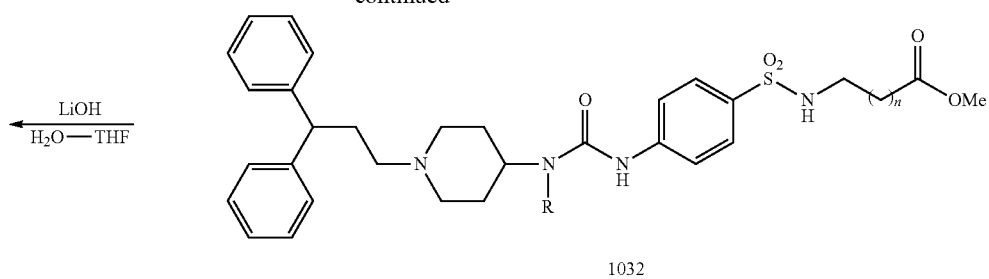
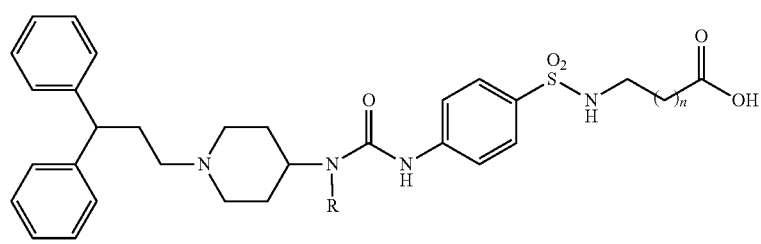
1033
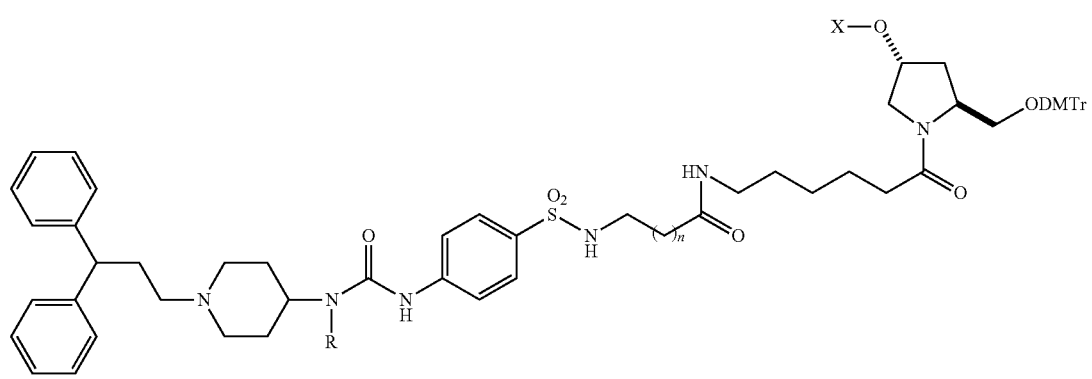
1034, X = 2-cyanoethylphosphoramidie
1035, X = succinimidyl-lcaa-CPG
Scheme 6
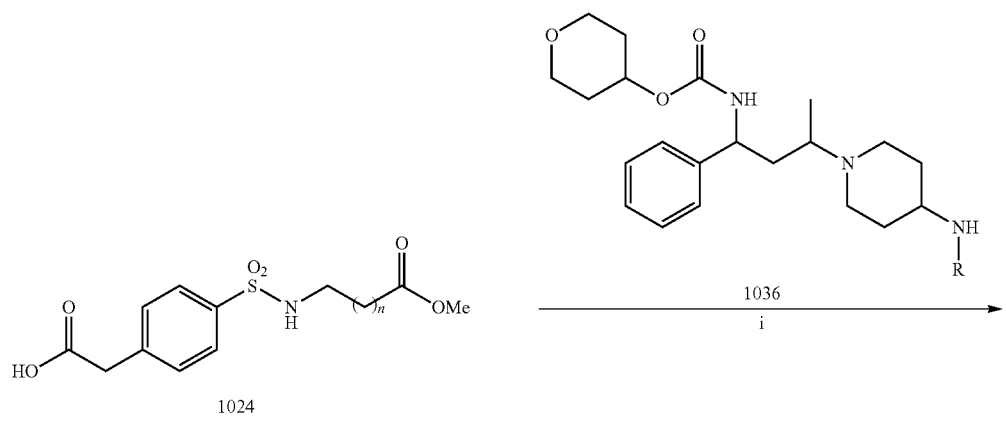

-continued
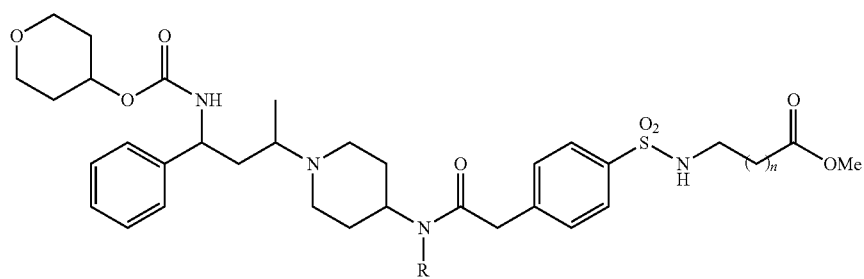
1037, R = H, Me, Et, Pr, isoPr, Allyl, cyclopropyl,
ii
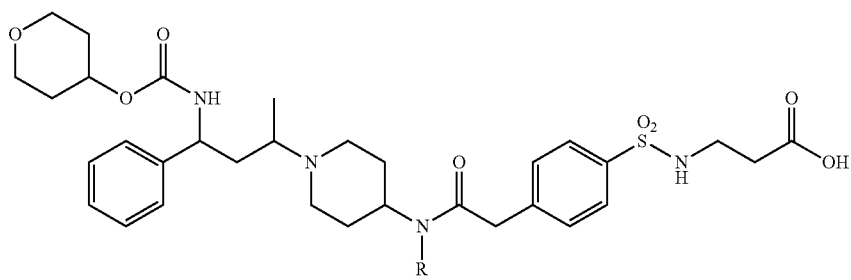
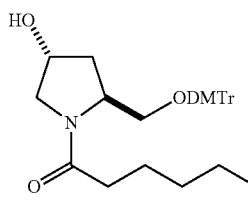
iii
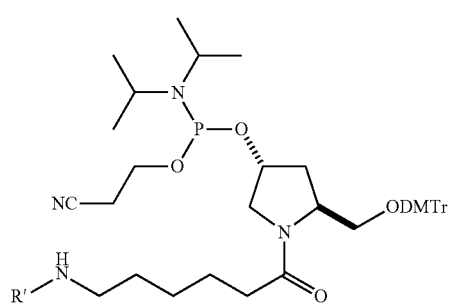
1040
iv -continued
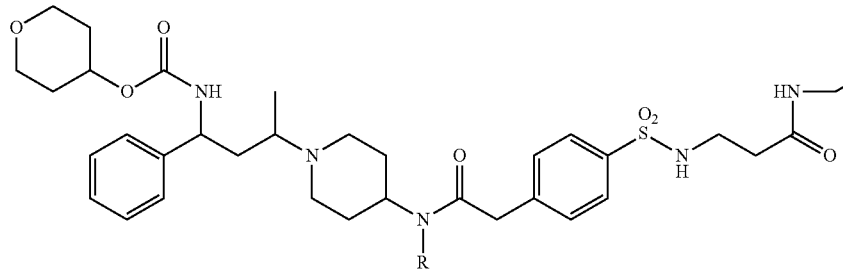
1039
↓ v
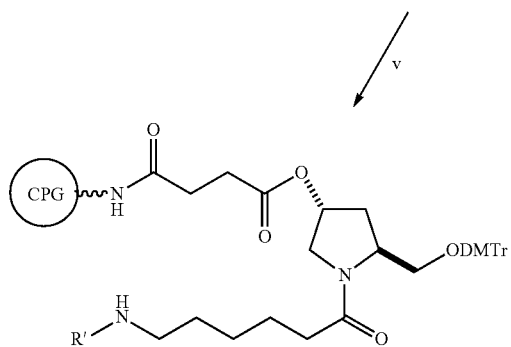
1041
Scheme 7
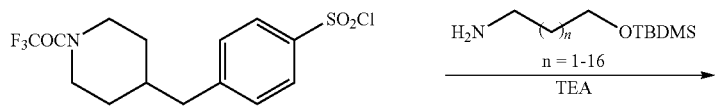
1042
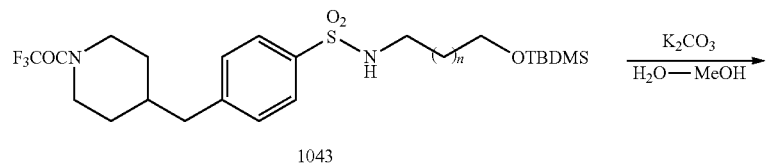
1043
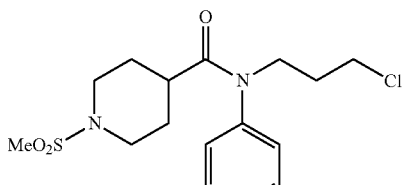
1045
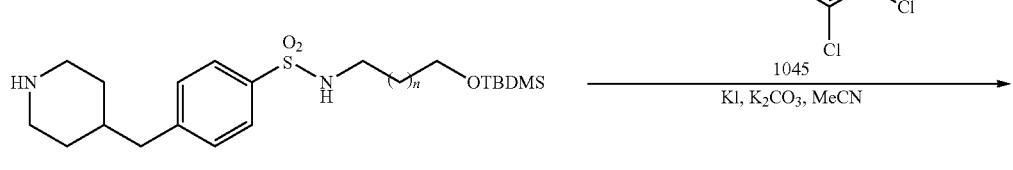
1044

-continued

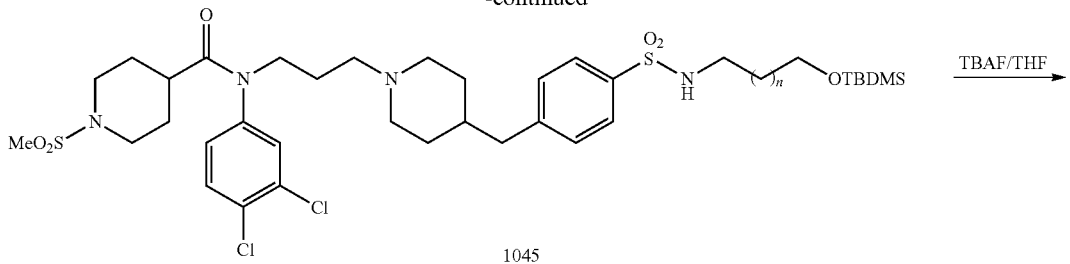

1045

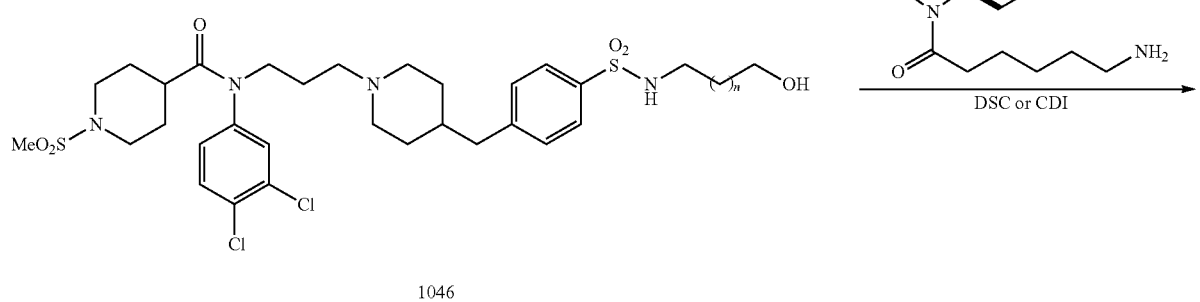

1046

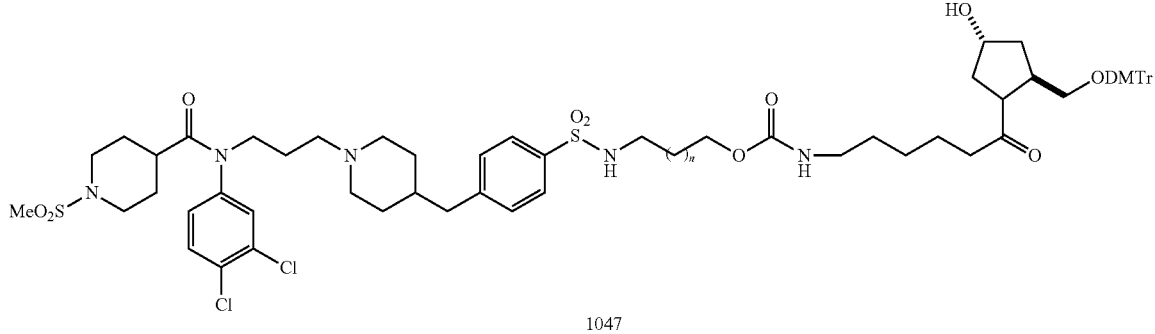

1047

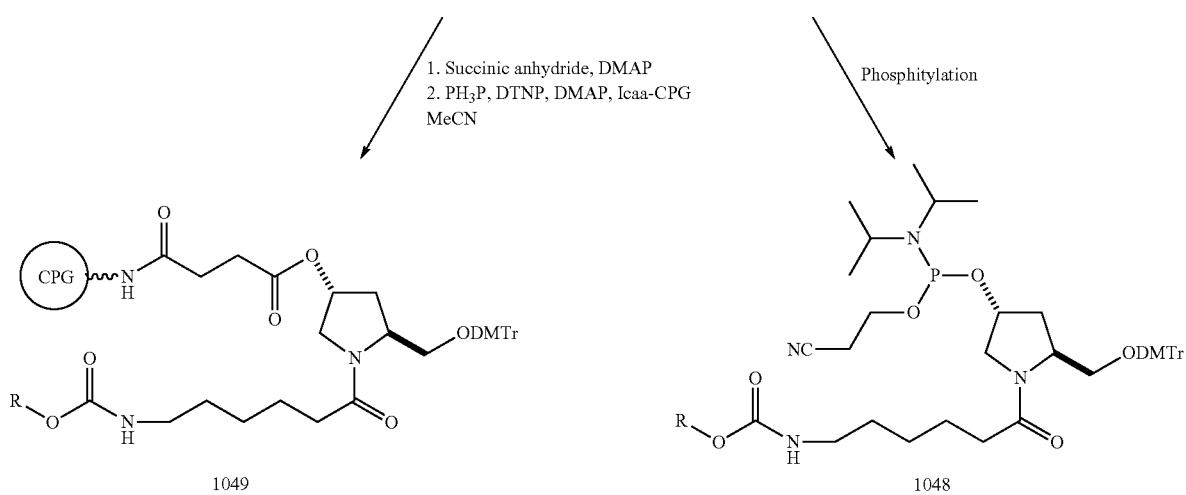

1049          1048

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Evaluation of Candidate iRNA Agents

One can evaluate a candidate iRNA agent (e.g., a modified candidate iRNA agent) for a selected property by exposing the agent and a control agent to the appropriate conditions and evaluating for the presence of the selected property. For example, the ability of an iRNA agent modified to target a CCR5-expressing cell can be evaluated as follows. A candidate modified iRNA agent and preferably a control iRNA agent of the unmodified form (e.g., an iRNA agent that is not conjugated to a CCR5-binding ligand) can be exposed to a cell expressing a gene (e.g., a reporter gene) targeted by the iRNA agent for degradation. The efficiency of uptake of the iRNA agent can be assayed by monitoring for a reduction in reporter gene activity. A candidate modified iRNA agent that targets a CCR5-expressing cell more efficiently than an unmodified iRNA agent can be selected for further assays (e.g., in vivo assays). Exemplary reporter genes include α-glucoronidase (GUS), luciferase, chloramphenicol transacetylase (CAT), horseradish peroxidase (HRP), alkaline phosphatase, acetylcholinesterase and β-galactosidase, red fluorescent protein (RFP), cyan fluorescent protein (CFP) and blue fluorescent protein (BFP).

To further test the specificity of a candidate iRNA agent, the candidate agent can be added to a mixture of cells, some expressing CCR5 (e.g., a CCR5+ Chinese hamster ovary cell line) and others not expressing CCR5 (e.g., a CCR5-peripheral blood mononuclear cell line). The candidate modified iRNA agent is added to the mixture of cells, and after a time sufficient to permit cell targeting and uptake, the cell mixture can be evaluated for uptake of the iRNA agent. For example, the CCR5+ and CCR5− cells can be separated by a cell sorter and assayed for the presence of the iRNA agent by Northern blot or RT-PCR analysis. A time course can be performed to determine the difference in efficiency of uptake of the modified iRNA agent in each cell type.

A functional assay can also be used to evaluate the candidate agent. A functional assay can be applied initially or after an earlier non-functional assay (e.g., an assay for targeting to a CCR5-expressing cell type) to determine if the modification alters the ability of the molecule to inhibit gene expression. For example, a CCR5+ cell (e.g., a mammalian CCR5+ cell, such as a mouse or human cell) can be co-transfected with a plasmid expressing a fluorescent protein (e.g., GFP) and a candidate iRNA agent homologous to the transcript encoding the fluorescent protein (see, e.g., WO 00/44914) and modified for enhanced targeting and uptake by CCR5-expressing cells. For example, a modified iRNA agent homologous to the GFP mRNA can be assayed for the ability to inhibit GFP expression by monitoring the decrease in cell fluorescence, as compared to a control cell, in which the transfection did not include the candidate iRNA agent (e.g., controls with no agent added and/or controls with a non-modified RNA added). Efficacy of the candidate agent on gene expression can be assessed by comparing cell fluorescence in the presence of the modified and unmodified iRNA agent.

In another functional assay, a candidate iRNA agent homologous to a gene expressed by SHIV-1 can be administered intravaginally or intrarectally to a mammal (e.g., a mouse or macaque monkey) and then the mammal can be exposed vaginally or rectally to SHIV-I (see e.g., *Nat Med.* 9:343-6, 2003). The mammal can then be assayed for infection by SHIV-1. The effect of the modified agent on target RNA levels can be further verified by northern blot to assay for the presence of the iRNA agent in the cells of the vagina or rectum or for the absence of the SHIV-1 RNA targeted by the iRNA agent. The exposed cells can also be monitored for CCR5 expression as compared to cells not exposed to SHIV-1 (mock-exposed cells) and uptake of the iRNA agent can be compared in the exposed and mock-exposed cell types. Controls can include cells that were exposed to an unmodified iRNA agent.

Physiological Effects

An iRNA agent conjugated to a CCR5-binding ligand can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal (e.g., a mouse, rat, dog, pig, goat, sheep, cow, macaque monkey, Pan paniscus, Pan troglodytes, Macaca mulatto, or Cynomolgus monkey). The sequence of the iRNA agent can be complementary to sequences within homologous genes of the non-human mammal and the human, or to a gene of a viral or bacterial pathogen that affects both animals. By determining the toxicity of the iRNA agent in the non-human mammal, one can extrapolate the toxicity of the iRNA agent in a human. For a more strenuous toxicity test, the iRNA agent can be complementary to a human and more than one (e.g., two or three or more) non-human animals.

The methods described herein can be used to correlate any physiological effect of an iRNA agent on a human, including any unwanted effect, such as a toxic effect, or any positive, or desired effect.

Formulations

The iRNA agents modified for enhanced targeting to CCR5-expressing cells can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents (e.g., modified iRNA agents) and such practice is within the invention.

A formulated iRNA composition featured in the invention can assume a variety of states. In some examples, the composition is at least partially crystalline, uniformly crystalline, and/or anhydrous (e.g., less than 80, 50, 30, 20, or 10% water). In another example, the modified iRNA agent is in an aqueous phase (e.g., in a solution that includes water). In some embodiments, the modified iRNA agent is in the form of an ointment, gel, or foam.

The aqueous phase or the crystalline compositions can be incorporated into a delivery vehicle (e.g., a liposome, particularly for the aqueous phase or, a microparticle appropriate for a crystalline composition). Generally, the iRNA composition is formulated in a manner that is compatible with the intended method of administration. In one embodiment, the iRNA agent conjugated to a CCR5-binding ligand is formulated for intravaginal delivery. In a preferred embodiment, the iRNA agent is formulated such that the modified iRNA agent featured in the invention is retained long-enough in the vagina to spread and adhere to cover the vaginal and cervical mucosa. For example, a composition formulated for intravaginal delivery can include a hydroxymethylcellulose (HMC) gel solution (e.g., a 2.5% HMC gel solution). In another preferred embodiment, the formulation does not substantially cause cell death, inflammation, or irritation of the vaginal epithelium or alteration of the normal vaginal flora. The CCR5-targeting iRNA agent featured in the invention and formulated for intravaginal administration preferably does not affect sperm viability or fertility. An exemplary formulation for intravaginal delivery includes a carrier matrix, a mucoadhesive, and a preservative. The formulation can include hydroxymethylcellulose, such as 0.0001-15% hydroxymethylcellulose (e.g., 0.01%, 0.1%, 2.5% 5%, 10%, 15% or more).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA preparation featured in the invention can be formulated in combination with another agent (e.g., another therapeutic agent or an agent that stabilizes an iRNA such as a protein that complexes with iRNA to form an iRNP). Still other agents include chelators (e.g., EDTA) to remove divalent cations such as $Mg^{2+}$, salts, RNAse inhibitors (e.g., a broad specificity RNAse inhibitor such as RNAsin) and so forth. In one embodiment the iRNA preparation comprises agents that block transmission of a virus (e.g., HIV-1) from one human to another. The agent can be a polyanion (e.g., Carbol 11382 or Carbopol 974P), mannan or its derivatives (e.g., to block C type lectin receptors), anti-inflammatory agents, or buffers (to lower pH). Formulations for intravaginal delivery can also include vaginal health-promoting ingredients, such as zinc.

In one embodiment, the iRNA preparation includes another iRNA agent (e.g., a second iRNA) that can inhibit translation of a second gene or the same gene. Still another preparation can include at least three, five, ten, twenty, fifty, or a hundred or more different iRNA species that interfere with a similar number of different genes, or one or more iRNA species can target the same gene. Preferably, at least one iRNA agent in a multi-iRNA agent preparation will be conjugated to a CCR5-ligand.

In one embodiment, the iRNA preparation includes a second therapeutic agent (e.g., an agent other than an RNA or a DNA). For example, an iRNA composition for the treatment of a viral infection (e.g., an HIV infection) might include a known HIV therapeutic (e.g., a dideoxynucleosides such as 3'-deoxy-3'-azidothymidine (AZT), 2',3'- dideoxyinosine (ddI), 2',3'- dideoxycytidine (ddC), and 2',3'-didehydro-3'-deoxythymidine).

Treatment Methods and Routes of Delivery

A composition that includes an iRNA agent conjugated to a CCR5-binding ligand can be delivered to a subject by a variety of routes. Exemplary routes include intravaginal, intrathecal, parenchymal (e.g., in the brain), nasal, and ocular delivery. The composition can also be delivered systemically (e.g., by intravenous, subcutaneous or intramuscular injection). The modified iRNA agents featured in the invention can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. A pharmaceutically acceptable carrier may include a transfection reagent or a reagent to facilitate uptake in a CCR5-expressing cell that is in addition to the CCR5-binding ligand conjugated to the iRNA agent featured in the invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including intravaginal, ophthalmic, intranasal, transdermal), oral, or parenteral. Parenteral administration includes intravenous drip, subcutaneous, intraperitoneal or intramuscular injection, intrathecal, or intraventricular (e.g., intracerebroventricular) administration.

The route of delivery can be dependent on the disorder of the patient. For example, a subject diagnosed with a viral infection can be administered an anti-viral iRNA agent conjugated to a CCR5-binding ligand intravenously. A female subject at risk for contracting HIV-1 from a sexual partner can be administered an iRNA agent intravaginally. In addition to an iRNA agent modified for enhanced delivery to CCr5-expressing cells, a patient can be administered a second therapy (e.g., a palliative therapy and/or disease-specific therapy). The secondary therapy can be, for example, symptomatic (e.g., for alleviating symptoms), neuroprotective (e.g., for slowing or halting disease progression), or restorative (e.g., for reversing the disease process).

Delivery methods that do not require passage of the composition across the blood-brain barrier can be utilized. For example, a pharmaceutical composition containing an iRNA agent can be delivered to the patient by injection directly into the area containing the disease-affected CCR5-expressing cells.

An iRNA agent conjugated to a CCR5-binding ligand can be further modified such that it is capable of traversing the blood brain barrier. For example, the iRNA agent can be conjugated to a molecule that enables the agent to traverse the barrier. Such modified iRNA agents can be administered by any desired method, such as by intraventricular or intramuscular injection, or by pulmonary delivery, for example.

The iRNA agent conjugated to a CCR5-binding ligand can be administered ocularly, such as to treat retinal disorder. For example, the pharmaceutical compositions can be applied to the surface of the eye or nearby tissue (e.g., the inside of the eyelid). They can be applied topically (e.g., by spraying, in drops, as an eyewash, or an ointment). Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the iRNA agent can also be applied via an ocular patch.

Administration can be provided by the subject or by another person (e.g., a caregiver). A caregiver can be any entity involved with providing care to the human: for example, a healthcare worker such as a doctor, nurse, or other practitioner; or a spouse, or guardian, such as a parent. The iRNA agent may be administered at the patient's home or in a hospital, hospice, doctor's office, or outpatient clinic. The medication can be provided in measured doses or in a dispenser which delivers a metered dose.

The subject can be monitored for an improvement or stabilization of disease symptoms following administration of the iRNA agent conjugated to a CCR5-binding ligand. Such monitoring can be achieved, for example, by assessing viral load (e.g., in HIV-infected individuals). Statistically significant differences in these measurements and outcomes for treated and untreated subjects are evidence of the efficacy of the treatment.

A pharmaceutical composition containing an iRNA agent conjugated to a CCR5-binding ligand can be administered to any patient diagnosed as having or at risk for developing a viral infection (e.g., an HIV infection). In general, an iRNA agent conjugated to a CCR5-binding ligand can be administered by any suitable method. As used herein, topical delivery can refer to the direct application of an iRNA agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the iRNA agent to the epidermis or dermis of a subject, or to specific strata thereof, or to an underlying tissue.

Compositions for intrathecal or intraventricular (e.g., intracerebroventricular) administration may include sterile aqueous solutions that may also contain buffers, diluents, and other suitable additives. Compositions for intrathecal or intraventricular administration preferably may include a transfection reagent or an additional lipophilic moiety for enhanced uptake into the CCR5-expressing cell.

Formulations for parenteral administration may include sterile aqueous solutions that may also contain buffers, diluents, and other suitable additives. Intraventricular injection may be facilitated by an intraventricular catheter, for example, attached to a reservoir. For intravenous use, the total concentration of solutes should be controlled to render the preparation isotonic.

An iRNA agent conjugated to a CCR5-binding agent for enhanced targeting to CCR5-expressing cells can be administered to a subject by pulmonary delivery. Pulmonary delivery compositions can be delivered through inhalation of a dispersion so that the iRNA within the dispersion can reach the lung where it can be readily absorbed through the alveolar region directly into blood circulation. Pulmonary delivery can be effective both for systemic delivery and for localized delivery to treat diseases of the lungs. In one embodiment, an iRNA agent administered by pulmonary delivery has been modified such that it is capable of traversing the blood brain barrier.

Pulmonary delivery can be achieved by different approaches, including the use of nebulized, aerosolized, micellular, and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element that can include a timer, a dose counter, time measuring device, or a time indicator that, when incorporated into the device, enables dose tracking, compliance monitoring, and/or dose triggering to a patient during administration of the aerosol medicament.

Because iRNA agent-mediated silencing persists for several days after administering the iRNA agent composition, in many instances it is possible to administer the composition with a frequency of less than once per day, or, for some instances, only once for the entire therapeutic regimen. For example, treatment of some cancer cells may be mediated by a single bolus administration, whereas a chronic viral infection may require regular administration (e.g., once per week or once per month).

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can administered to the patient with no significant adverse toxicological effects.

The types of pharmaceutical excipients that are useful as carrier include stabilizers such as HSA; bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An iRNA agent conjugated to a CCR5-binding moiety for enhanced targeting and uptake into CCR5-expressing cells can be administered by oral or nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized, and removed easily.

In one embodiment, unit doses or measured doses of a composition that include iRNA are dispensed by an implanted device. The device can include a sensor that monitors a parameter within a subject. For example, the device can include a pump, such as an osmotic pump and, optionally, associated electronics.

An iRNA agent can be packaged in a viral natural capsid or in a chemically or enzymatically produced artificial capsid or structure derived therefrom.

Dosage. An iRNA agent modified for enhanced targeting and uptake into CCR5-expressing cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an iRNA agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder associated with CCR5 expression (e.g., a viral or bacterial infection, or an autoimmune or inflammatory disease or disorder).

In one embodiment, the unit dose is administered less frequently than once a day (e.g., less than every 2, 4, 8, or 30 days). In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has an HIV infection and the modality is a therapeutic agent other than an iRNA agent (e.g., other than a double-stranded iRNA agent or siRNA agent). The therapeutic modality can be, for example, dideoxynucleosides such as AZT, ddI, ddC, or 2',3'-didehydro-3'-deoxythymidine.

In one embodiment, a subject is administered an initial dose, and one or more maintenance doses of an iRNA agent (e.g., a double-stranded iRNA agent conjugated to a CCR5-binding ligand). The maintenance dose or doses are generally lower than the initial dose (e.g., one-half of the initial dose). A maintenance regimen can include treating the subject with a dose or doses ranging from 0.01 µg to 1.4 mg/kg of body weight per day (e.g., 10, 1, 0.1, 0.01, 0.001, or 0.00001 mg per kg of bodyweight per day). The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day (e.g., no more than once per 24, 36, 48, or more hours) and no more than once every 5 or 8 days. Following treatment, the patient can be monitored for changes in his condition and for alleviation of the symptoms of the disease state. The dosage of the compound may be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device (e.g., a pump or semi-permanent stent for intravenous, intraperitoneal, intracistemal or intracapsular delivery) or a reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

Following successful treatment, it may be desirable to have the patient undergo maintenance therapy to prevent the recurrence of the disease state, wherein the compound featured in the invention is administered in maintenance doses, ranging from 0.01 µg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration (e.g. nasal, buccal, or pulmonary). For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent (e.g., an iRNA agent conjugate to a CCR5-binding ligand) can include a single treatment or a series of treatments. It will also be appreciated that the effective dosage of an iRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies, and repetition rates. Optimum dosages may vary depending on the relative potency of individual compounds, and can generally be estimated based on $EC_{50}$s found to be effective in in vitro and in vivo animal models. In some embodiments, the animal models include transgenic animals that express a human gene (e.g., a gene that produces a target RNA in a cell that also expresses CCR5). The transgenic animal can be deficient for the corresponding endogenous RNA. In another embodiment, the composition for testing includes an iRNA agent that is complementary, at least in an internal region, to a sequence that is conserved between the target RNA in the animal model and the target RNA in a human.

Kits. In certain other aspects, the invention provides kits that include a suitable container containing a pharmaceutical formulation of an iRNA agent (e.g., a double-stranded iRNA agent; a precursor, a larger iRNA agent which can be processed into a iRNA agent, or a DNA that encodes an iRNA agent). In certain embodiments the individual components of the pharmaceutical formulation may be provided in one container. Alternatively, it may be desirable to provide the components of the pharmaceutical formulation separately in two or more containers (e.g., one container for an iRNA agent preparation and at least another for a carrier compound). The kit may be packaged in a number of different configurations such as one or more containers in a single box. The different components can be combined (e.g., according to instructions provided with the kit). The components can be combined according to a method described herein (e.g., to prepare and administer a pharmaceutical composition). The kit can also include a delivery device.

Ligand-Conjugated Monomer Subunits And Monomers For Oligonucleotide Synthesis Definitions The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —N(alkyl)$_2$ radicals, respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals, respectively. The term "siloxy" refers to an $R_3SiO$- radical. The term "mercapto" refers to an SH radical. The term "thioalkoxy" refers to an -S-alkyl radical.

The term "alkylene" (i.e., -R-)refers to a divalent alkyl (e.g., —CH$_2$—, —CH$_2$CH$_2$—, and —CH$_2$CH$_2$CH$_2$—). The term alkenylene refers to a divalent alkenyl (e.g., —CH$_2$CH═CH—, polyalkenyl). The term alkynylene refers to a divalent alkynyl (e.g., propargyl, polyalkynyl). The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group (e.g., a hydroxyl group or an amino group) or a class of molecules (e.g., sugars) having one or more functional groups, in which the reactivity of the functional group is temporarily blocked by the presence of an attached protecting group. Protecting groups useful for the monomers and methods described herein can be found in, for example, Greene, T.

W, *Protective Groups in Organic Synthesis* (John Wiley and Sons: New York), 1981, which is hereby incorporated by reference.

General iRNA Chemistry

An iRNA agent (e.g., a single-stranded conjugated iRNA agent) containing a preferred, but nonlimiting ligand-conjugated monomer subunit is presented as formula (II) below. The carrier (also referred to in some embodiments as a "linker") can be a cyclic or acyclic moiety and includes two "backbone attachment points" (e.g., hydroxyl groups) and a ligand. The ligand can be directly attached (e.g., conjugated) to the carrier or indirectly attached (e.g., conjugated) to the carrier by an intervening tether (e.g., an acyclic chain of one or more atoms; or a nucleobase, a naturally occurring nucleobase optionally having one or more chemical modifications; an unusual base; or a universal base). The carrier therefore also includes a "ligand or tethering attachment point" for the ligand and tether/tethered ligand, respectively.

The ligand-conjugated monomer subunit may be the 5' or 3' terminal subunit of the RNA molecule (i.e., one of the two "W" groups may be a hydroxyl group, and the other "W" group may be a chain of two or more unmodified or modified ribonucleotides). Alternatively, the ligand-conjugated monomer subunit may occupy an internal position, and both "W" groups may be one or more unmodified or modified ribonucleotides. More than one ligand-conjugated monomer subunit may be present in an iRNA agent. Preferred positions for inclusion of a tethered ligand-conjugated monomer subunit are at the 3' terminus, the 5' terminus, or at an internal position.

the hydroxyl proton has been replaced by another substituent. As shown in representative structures B and C below, one hydroxyl group ($OFG^1$) on the carrier is functionalized with a protecting group (PG). The other hydroxyl group ($OFG^2$) can be functionalized with either (1) a liquid- or solid-phase synthesis support reagent (solid circle) directly or indirectly through a linker, L, as in B, or (2) a phosphorus-containing moiety (e.g., a phosphoramidite) as in C. The tethering attachment point may be connected to a hydrogen atom, a suitable protecting group, a tether, or a tethered ligand at the time that the monomer is incorporated into the growing strand (see variable "R" in A below). Thus, the tethered ligand can be, but need not be, attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule interposed between the moiety and the attachment point. Directly tethered means the moiety is bound directly to the attachment point. Indirectly tethered means that there is a tether molecule interposed between the attachment point and the moiety.

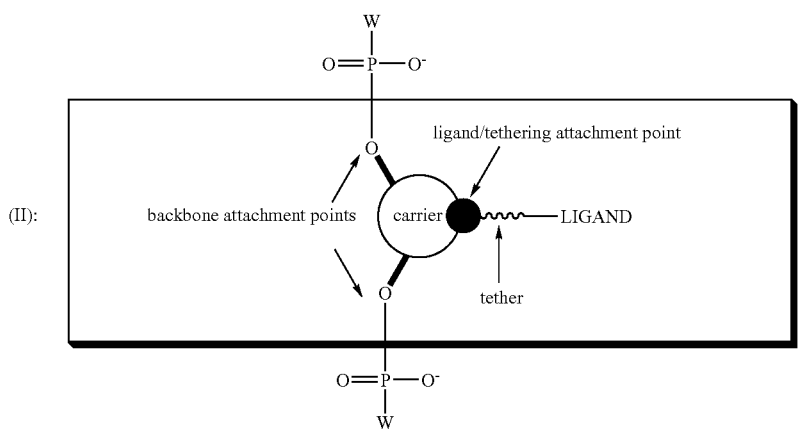

(II):

The modified RNA molecule of formula (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below) into a growing strand, utilizing, but not limited to, phosphoramidite or H-phosphonate coupling strategies.

The monomers (e.g., ligand-conjugated monomers) generally include two differently functionalized hydroxyl groups ($OFG^1$ and $OFG^2$) linked to the carrier molecule (see A below) and a ligand/tethering attachment point. As used herein, the term "functionalized hydroxyl group" means that A:
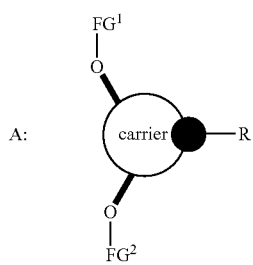

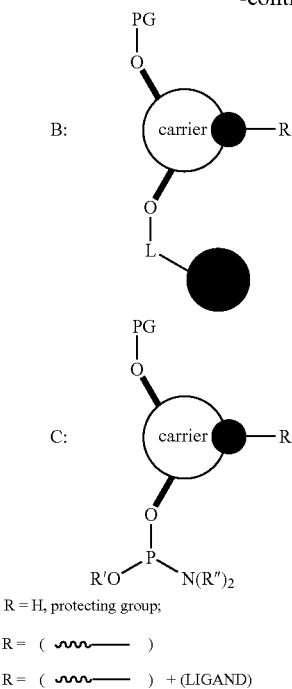

R = H, protecting group;

R = ( ~~~ )

R = ( ~~~ ) + (LIGAND)

The (OFG¹) protecting group may be selected as desired (e.g., from T. W. Greene and P. G. M. Wuts, *Protective Groups in Organic Synthesis,* 2d. Ed., John Wiley and Sons, 1991). The protecting group is preferably stable under amidite synthesis conditions, storage conditions, and oligonucleotide synthesis conditions. Hydroxyl groups, —OH, are nucleophilic groups (i.e., Lewis bases) that react through the oxygen with electrophiles (i.e., Lewis acids). Hydroxyl groups in which the hydrogen has been replaced with a protecting group (e.g., a triarylmethyl group or a trialkylsilyl group) are essentially unreactive as nucleophiles in displacement reactions. Thus, the protected hydroxyl group is useful in preventing undesired side products (e.g., homocoupling of compounds exemplified by structure C) during oligonucleotide synthesis. In some embodiments, a preferred protecting group is the dimethoxytrityl group. In other embodiments, a preferred protecting group is a silicon-based protecting group having the formula below:

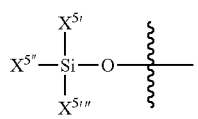

$X^{5'}$, $X^{5''}$, and $X^{5'''}$ can be selected from substituted or unsubstituted alkyl, cycloalkyl, aryl, araklyl, heteroaryl, alkoxy, cycloalkoxy, aralkoxy, aryloxy, heteroaryloxy, or siloxy (i.e., $R_3SiO$—, the three "R" groups can be any combination of the above listed groups). $X^{5'}$, $X^{5''}$, and $X^{5'''}$ may be the same or different; also contemplated is a combination in which two of $X^{5'}$, $X^{5''}$, and $X^{5'''}$ are identical and the third is different. In certain embodiments $X^{5'}$, $X^{5''}$, and $X^{5'''}$ include at least one alkoxy or siloxy group. A preferred combination includes $X^{5'}$ and $X^{5''}$=trimethylsiloxy and $X^{5'''}$=1,3-(triphenylmethoxy)-2-propoxy or cyclododecyloxy.

Other preferred combinations of $X^{5'}$, $X^{5''}$, and $X^{5'''}$ include those that result in OFG¹ groups that meet the deprotection and stability criteria delineated below. The group is preferably stable under amidite synthesis conditions, storage conditions, and oligonucleotide synthesis conditions. Rapid removal (i.e., less than one minute) of the silyl group from a support-bound oligonucleotide is desired because it can reduce synthesis times and thereby reduce exposure time of the growing oligonucleotide chain to the reagents. Oligonucleotide synthesis can be improved if the silyl protecting group is visible during deprotection (e.g., from the addition of a chromophore silyl substituent).

Selection of silyl protecting groups can be complicated by the competing demands of the essential characteristics of stability and facile removal, and the need to balance these competitive goals. Most substituents that increase stability can also increase the reaction time required for removal of the silyl group, potentially increasing the level of difficulty in removal of the group.

The addition of alkoxy and siloxy substituents to OFG¹ silicon-containing protecting groups increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable nucleoside protecting group.

Candidate OFG¹ silicon-containing protecting groups may be tested by exposing a tetrahydrofuran solution of a preferred carrier bearing the candidate OFG¹ group to five molar equivalents of tetrahydrofuran at room temperature. The reaction time may be determined by monitoring the disappearance of the starting material by thin layer chromatography.

When the OFG² in B includes a linker (e.g., a relatively long organic linker) connected to a soluble or insoluble support reagent, solution- or solid-phase synthesis techniques can be employed to build up a chain of natural and/or modified ribonucleotides once OFG¹ is deprotected and free to react as a nucleophile with another nucleoside or monomer containing an electrophilic group (e.g., an amidite group). Alternatively, a natural or modified ribonucleotide or oligoribonucleotide chain can be coupled to monomer C via an amidite group or H-phosphonate group at OFG². Subsequent to this operation, OFG¹ can be deblocked, and the restored nucleophilic hydroxyl group can react with another nucleoside or monomer containing an electrophilic group. R' can be substituted or unsubstituted alkyl or alkenyl. In preferred embodiments, R' is methyl, allyl or 2-cyanoethyl. R" may a $C_1$-$C_{10}$ alkyl group, preferably it is a branched group containing three or more carbons (e.g., isopropyl).

OFG² in B can be hydroxyl functionalized with a linker that in turn contains a liquid- or solid-phase synthesis support reagent at the other linker terminus. The support reagent can be any support medium that can support the monomers described herein. The monomer can be attached to an insoluble support via a linker, L, that allows the monomer (and the growing chain) to be solubilized in the solvent in which the support is placed. The solubilized, yet immobilized, monomer can react with reagents in the surrounding solvent; unreacted reagents and soluble by-products can be readily washed away from the solid support to which the monomer or monomer-derived products is attached. Alternatively, the monomer can be attached to a soluble support moiety (e.g., polyethylene glycol, PEG) and liquid-phase synthesis techniques can be used to build up the chain. Linker and support medium selection is within skill of the art. Generally the linker may be —C(O)(CH$_2$)$_q$C(O)—, or —C(O)(CH$_2$)$_q$S—, in which q can be 0, 1, 2, 3, or 4; preferably, it is oxalyl, succinyl or thioglycolyl. Standard control pore glass solid-phase synthesis supports cannot be used in conjunction with fluoride labile 5' silyl protecting groups because the glass is degraded by fluoride with a significant reduction in the amount of full-length product. Fluoride-stable polystyrene based supports or PEG are preferred.

The ligand/tethering attachment point can be any divalent, trivalent, tetravalent, pentavalent, or hexavalent atom. In some embodiments, ligand/tethering attachment point can be a carbon, oxygen, nitrogen, or sulfur atom. For example, a ligand/tethering attachment point precursor functional group can have a nucleophilic heteroatom (e.g., —SH, —NH$_2$, secondary amino, ONH$_2$, or NH$_2$NH$_2$). As another example, the ligand/tethering attachment point precursor functional group can be an olefin (e.g., —CH=CH$_2$ or a Diels-Alder diene or dienophile) and the precursor functional group can be attached to a ligand, a tether, or tethered ligand using transition metal catalyzed carbon-carbon (for example olefin metathesis) processes or cycloadditions (e.g., Diels-Alder). As a further example, the ligand/tethering attachment point precursor functional group can be an electrophilic moiety (e.g., an aldehyde). When the carrier is a cyclic carrier, the ligand/tethering attachment point can be an endocyclic atom (i.e., a constituent atom in the cyclic moiety, such as a nitrogen atom) or an exocyclic atom (i.e., an atom or group of atoms attached to a constituent atom in the cyclic moiety).

The carrier can be any organic molecule containing attachment points for OFG$^1$, OFG$^2$, and the ligand. In certain embodiments, carrier is a cyclic molecule and may contain heteroatoms (e.g., O, N or S). For example, carrier molecules may include aryl (e.g., benzene or biphenyl), cycloalkyl (e.g., cyclohexane, cis or trans decalin), or heterocyclyl (e.g., piperazine or pyrrolidine). In other embodiments, the carrier can be an acyclic moiety (e.g., based on serinol). Any of the above cyclic systems may include substituents in addition to OFG$^1$, OFG$^2$, and the ligand.

iRNA Agent Structure

The monomers described herein can be used to make oligonucleotides that are useful as iRNA agents (e.g., double-stranded or single-stranded RNA molecules) that mediate RNAi with respect to an endogenous gene of a subject or to a gene of a pathogen. In most cases the iRNA agent will incorporate monomers described herein together with naturally occuring nucleosides or nucleotides or with other modified nucleosides or nucleotides. The modified monomers can be present at any position in the iRNA agent (e.g., at the terminii or in the middle region of an iRNA agent or in a duplex region or in an unpaired region). In a preferred embodiment iRNA agent can have any architecture (e.g., architecture described herein). For example, the iRNA agent can have an overhang structure, a hairpin or other singled-strand structure, or a two-strand structure, as described herein.

The iRNA agent modified for enhanced uptake into CCR5-expressing cells should include a region of sufficient homology to the target gene, and be of sufficient length in terms of nucleotides, such that the iRNA agent, or a fragment thereof, can mediate down regulation of the target gene. It is not necessary that there be perfect complementarity between the iRNA agent and the target, but the correspondence must be sufficient to enable the iRNA agent, or a cleavage product thereof, to direct sequence specific silencing (e.g., by RNAi cleavage of the target RNA, usually an mRNA).

Mismatches to the target RNA sequence, particularly in the antisense strand of the iRNA agent, are tolerated most readily in the terminal regions and if present are preferably in a terminal region or regions (e.g., within 6, 5, 4, or 3 nucleotides of the 5' and/or 3' terminus) most preferably within 6, 5, 4, or 3 nucleotides of the 5' terminus of the sense strand or 3' terminus of the antisense strand. The sense strand need only be sufficiently complementary with the antisense strand to maintain the over all double-stranded character of the molecule.

As discussed elsewhere herein, an iRNA agent will often be modified or include nucleoside surrogates in addition to the SRMS. Single-stranded regions of an iRNA agent will often be modified or include nucleoside surrogates (e.g., the unpaired region or regions of a hairpin structure, a region that links two complementary regions). Modifications to stabilize the 3'- or 5'-termini of an iRNA agent against exonucleases or to favor entry of the iRNA agent into RISC are also favored. Modifications can include C3 (or C6, C7, C12) amino linkers, thiol linkers, carboxyl linkers, non-nucleotidic spacers (e.g., C3, C6, C9, C12, abasic, triethylene glycol, hexaethylene glycol), orspecial biotin or fluorescein reagents that come as phosphoramidites and that have another DMT-protected hydroxyl group, allowing multiple couplings during RNA synthesis.

Although, in mammalian cells, long dsRNAs can induce the frequently deleterious interferon response, short dsRNAs do not trigger the interferon response, at least not to an extent that is deleterious to the cell and host. In particular, the length of the iRNA agent strands can be less than 31, 30, 28, 25, or 23 nt (e.g., sufficiently short to avoid inducing a deleterious interferon response). Thus, the administration of a composition of an iRNA agent (e.g., formulated as described herein) to a mammalian cell can be used to silence expression of a target gene while circumventing the interferon response. Further, use of a discrete species of iRNA agent can be used to selectively target one allele of a target gene (e.g., in a subject heterozygous for the allele).

For ease of exposition the term nucleotide or ribonucleotide is sometimes used herein in reference to one or more monomeric subunits of an iRNA agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

An iRNA agent will preferably have one or more of the following properties:
(1) It will have a 5' modification that includes one or more phosphate groups or one or more analogs of a phosphate group;
(2) it will, despite modifications even to a very large number of bases, specifically base pair and form a duplex structure with a homologous target RNA of sufficient thermodynamic stability to allow modulation of the activity of the targeted RNA;
(3) it will, despite modifications, even to a very large number or all of the nucleosides, still have "RNA-like" properties (i.e., it will possess the overall structural, chemical and physical properties of an RNA molecule) even though it is not exclusively, or even partly, of ribonucleotide-based content. For example, all of the nucleotide sugars can contain 2'O-Me or 2'-fluoro in place of 2'-hydroxyl. This deoxyribonucleotide-containing agent can still be expected to exhibit RNA-like properties. While not wishing to be bound by theory, an electronegative fluorine prefers an axial orientation when attached to the C2' position of ribose. This spatial preference of fluorine can, in turn, force the sugars to adopt a $C_3$-endo pucker. This is the same puckering mode as observed in RNA molecules and gives rise to the characteristic A-family-type helix adopted by double-stranded regions of RNA. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into hydrogen-bonding that is more characteristic of the 2'-OH moiety of a ribonucleotide than the 2'-H moiety of a deoxyribonucleotide. A preferred iRNA agent will exhibit a $C_3$,-endo pucker in all or at least 50, 75, 80, 85, 90, or 95% of its sugars; will exhibit a $C_3$,-endo pucker in a sufficient amount of its sugars that it can give rise to a the A-family-type helix; will have no more than 20, 10, 5, 4, 3, 2, or 1 sugar that does not adopt a $C_3$,-endo pucker structure.

Preferred 2'-modifications with C3'-endo sugar pucker include:

2'—OH, 2'—O-Me, 2'-O-methoxyethyl, 2'-O-amino-propyl, 2'-F, 2'—O—CH$_2$—CO—NHMe, 2'—O—CH$_2$—CH$_2$—O—CH$_2$—CH$_2$—N(Me)$_2$, and LNA (4) regardless of the nature of the modification, and even though the iRNA agent can contain deoxynucleotides or modified deoxynucleotides, it is preferred that DNA molecules, or any molecule in which more than 50, 60, or 70% of the nucleotides in the molecule are deoxyribonucleotides, or modified deoxyribonucleotides that are deoxy at the 2' position or adopt a C2'-endo sugar pucker characteristic of a DNA-like helix, are excluded from the definition of iRNA agent.

Preferred 2'-modifications with a C2'-endo sugar pucker include:

2'—H, 2'-Me, 2'-S-Me, 2'-Ethynyl, 2'-ara-F.

Sugar modifications can also include L-sugars and 2'-5'-linked sugars.

As used herein, "specifically hybridizable" and "complementary" are terms that are used to indicate a sufficient degree of complementarity such that stable and specific binding occurs between an iRNA agent featured in the invention and a target RNA molecule (e.g., an RNA molecule in a CCR5-expressing cell). Specific binding requires a sufficient lack of complementarity to non-target sequences under conditions in which specific binding is desired (i.e., under physiological conditions in the case of in vivo assays or therapeutic treatment, or under conditions in which the assays are performed in the case of in vitro assays). It has been shown that a single mismatch between targeted and non-targeted sequences is sufficient to provide discrimination for siRNA targeting of an mRNA (Brummelkamp et al., *Cancer Cell,* 2002, 2:243).

In one embodiment, an iRNA agent conjugated to a CCR5-binding ligand is "sufficiently complementary" to a target RNA, such that the iRNA agent inhibits production of protein encoded by the target RNA. The target RNA can be, but are not limited to, an mRNA or miRNA endogenous to the subject. In another embodiment, the iRNA agent is "exactly complementary" (excluding the SRMS containing subunit(s)) to a target RNA (e.g., the target RNA and the iRNA agent can anneal to form a hybrid made exclusively of Watson-Crick base pairs in the region of exact complementarity). A "sufficiently complementary" target RNA can include a region (e.g., of at least 7 nucleotides) that is exactly complementary to a target RNA. Moreover, in some embodiments, the iRNA agent specifically discriminates a single-nucleotide difference. In this case, the iRNA agent only down-regulates gene expression if exact complementarity is found in the region of the single-nucleotide difference.

iRNA agents discussed herein include otherwise unmodified RNA as well as RNA that has been modified (e.g., to improve efficacy, and polymers of nucleoside surrogates).

Unmodified RNA refers to a molecule in which the components of the nucleic acid, namely sugars, bases, and phosphate moieties, are the same or essentially the same as those which occur in nature, preferably as occur naturally in the human body. The art has referred to rare or unusual, but naturally occurring, RNAs as modified RNAs, see, e.g., Limbach et al. (*Nucleic Acids Res.,* 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from those that occur in nature, preferably different from those that occur in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone (e.g., non-charged mimics of the ribophosphate backbone). Examples of each of the above are discussed herein.

As nucleic acids are polymers of subunits or monomers, many of the modifications described below occur at a unit that is repeated within a nucleic acid (e.g., a base, phosphate moiety, or a non-linking oxygen of a phosphate moiety). In some cases the modification will occur at all of the subject positions in the nucleic acid, but in most cases it will not. By way of example, a modification may only occur at a 3' or 5' terminal position, in a terminal region (e.g., at a position on a terminal nucleotide, or in the last 2, 3, 4, or 5 nucleotides of a strand). The ligand can be attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. For example, a phosphorothioate modification at a non-linking oxygen may only occur at one or both termini, or may only occur in a terminal region (e.g., at a position on a terminal nucleotide or in the last 2, 3, 4, or 5 nucleotides of the oligonucleotide. The 5' end can be phosphorylated.

Enhanced Nuclease Resistance

An iRNA agent (e.g., an iRNA agent that targets a cell expressing CCR5) can have enhanced resistance to nucleases. One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites for serum or cellular nucleases, as described in co-owned and co-pending applications U.S. 60/574,744 and PCT/US2005/018931.

For increased nuclease resistance and/or binding affinity to the target, an iRNA agent (e.g., the sense and/or antisense strands of the iRNA agent) can include, for example, 2'-modified ribose units and/or phosphorothioate linkages (e.g., the 2' hydroxyl group can be modified or replaced with a number of different "oxy" or "deoxy" substituents).

Examples of "oxy"-2' hydroxyl group modifications include alkoxy or aryloxy (OR, where R can be H, alkyl, cycloalkyl, aryl, aralkyl, heteroaryl, or sugar); polyethylene glycols (PEG, O(CH$_2$CH$_2$O)$_n$CH$_2$CH$_2$OR); "locked" nucleic acids (LNA) in which the 2' hydroxyl is connected by a methylene bridge to the 4' carbon of the same ribose sugar; O-AMINE (whre AMINE can be NH$_2$, alkylamino, dialkylamino, heterocyclyl, arylamino, diaryl amino, heteroaryl amino, diheteroaryl amino, ethylene diamine, or polyamino) and aminoalkoxy $(O(CH_2)_n AMINE$, where AMINE can be $NH_2$, alkylamino, dialkylamino, heterocyclyl, arylamino, diaryl amino, heteroaryl amino, diheteroaryl amino, ethylene diamine, or polyamino). It is noteworthy that oligonucleotides containing only the methoxyethyl group (MOE, $OCH_2CH_2OCH_3$, a PEG derivative) exhibit nuclease stabilities comparable to those modified with the phosphorothioate modification.

"Deoxy" modifications include hydrogen (i.e. deoxyribose sugars, which are of particular relevance to the overhang portions of many iRNA agents), halo (e.g., fluoro), amino (e.g. $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (where AMINE can be $NH_2$, alkylamino, dialkylamino, heterocyclyl, arylamino, diaryl amino, heteroaryl amino, or diheteroaryl amino), —NHC(O)R (where R can be alkyl, cycloalkyl, aryl, aralkyl, heteroaryl, or sugar), cyano, mercapto, alkyl-thio-alkyl, thioalkoxy, or alkyl, cycloalkyl, aryl, alkenyl and alkynyl (optionally substituted with an amino functionality). Preferred substituents are 2'-methoxyethyl, 2'-OCH3, 2'-O-allyl, 2'-C- allyl, and 2'-fluoro.

To maximize nuclease resistance, the 2' modifications can be used in combination with one or more phosphate linker modifications (e.g., phosphorothioate). The so-called "chimeric" oligonucleotides are those that contain two or more different modifications.

In certain embodiments, all the pyrimidines of an iRNA agent carry a 2'-modification, and the iRNA agent therefore has enhanced resistance to endonucleases. Enhanced nuclease resistance can also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, 3, 4 or 5 such dinucleotides. Preferably, the 5'-most pyrimidines in all occurrences of the sequence motifs 5'-UA-3', 5'-CA-3', 5'-UU-3', and 5'-UG-3' are 2'-modified nucleotides. More preferably, all pyrimidines in the sense strand and the 5'-most pyrimidines in all occurrences of the sequence motifs 5'-UA-3' and 5'-CA-3' are 2'-modified nucleotides. Most preferably, all pyrimidines in the sense strand are 2'-modified nucleotides and the 5'-most pyrimidines in all occurrences of the sequence motifs 5'-UA-3', 5'-CA-3', 5'-UU-3', and 5'-UG-3' in the antisense strand are 2'-modified nucleotides. The latter patterns of modifications have been shown by the current inventors to maximize the contribution of the nucleotide modifications to the stabilization of the overall molecule towards nuclease degradation, while minimizing the overall number of modifications required to a desired stability, see co-owned and co-pending PCT/US2005/018931, hereby incorporated herein by reference in its entirety.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group (e.g., a 3' C5-aminoalkyl dT). Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose, etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose, etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include monomers that have been modified so as to inhibit degradation (e.g., by endonucleases or exonucleases found in the body of a subject). These monomers are referred to herein as NRMs, or Nuclease Resistance promoting Monomers or modifications. In many cases these modifications will modulate other properties of the iRNA agent as well, for example. the ability to interact with a protein (e.g., a transport protein, serum albumin, a member of the RISC) or the ability of the first and second sequences to form a duplex with one another or to form a duplex with another sequence (e.g., a target molecule).

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent inactive with respect to its intended activity as a target RNA cleavage-directing agent. Again, while not wishing to be bound by any theory, it is believed that placement of the modifications at or near the 3' and/or 5'-end of antisense strands can result in iRNA agents that meet the preferred nuclease resistance criteria delineated above. Again, still while not wishing to be bound by any theory, it is believed that placement of the modifications at, for example, the middle of a sense strand can result in iRNA agents that are unlikely to cause off-target effects.

Modifications that can be useful for producing iRNA agents that meet the preferred nuclease resistance criteria delineated above can include one or more of the following chemical and/or stereochemical modifications of the sugar, base, and/or phosphate backbone:

(1) chiral ($S_P$) thioates. Thus, preferred NRMs include nucleotide dimers with an enriched or pure form of a particular chiral form of a modified phosphate group containing a heteroatom at the nonbridging position (e.g., Sp or Rp) at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(2) attachment of one or more cationic groups to the sugar, base, and/or the phosphorus atom of a phosphate or modified phosphate backbone moiety. Thus, preferred NRMs include monomers at the terminal position that are derivatized with a cationic group. As the 5'-end of an antisense sequence should have a terminal —OH or phosphate group this NRM is preferably not used at the 5'-end of an antisense sequence. The group should be attached at a position on the base that minimizes interference with hydrogen bond formation and hybridization (e.g., away form the face that interacts with the complementary base on the other strand, for example, at the 5' position of a pyrimidine or a 7-position of a purine). These are discussed in more detail below;

(3) nonphosphate linkages at the termini. Thus, preferred NRMs include non-phosphate linkages (e.g., a linkage of 4 atoms that confers greater resistance to cleavage than does a phosphate bond). Examples include 3'—CH2—$NCH_3$—O—$CH_2$-5' and 3'—$CH_2$—NH—(O=)—$CH_2$-5';

(4) 3'-bridging thiophosphates and 5'-bridging thiophosphates. Preferred NRM's can included these structures;

(5) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates, and boronophosphates); dimers having inverted linkages (e.g., 3'-3' or 5'-5' linkages); monomers having an alpha linkage at the 1' site on the sugar (e.g., the structures described herein having an alpha linkage);

(6) conjugate groups. Thus, preferred NRM's can include a targeting moiety or a conjugated ligand described herein conjugated with the monomer (e.g., through the sugar, base, or backbone);

(7) abasic linkages. Thus, preferred NRM's can include an abasic monomer as described herein (e.g., a nucleobaseless monomer); an aromatic or heterocyclic or polyheterocyclic aromatic monomer as described herein; and (8) 5'-phosphonates and 5'-phosphate prodrugs. Thus, preferred NRM's include monomers, preferably at the 5' terminal position in which one or more atoms of the phosphate group is derivatized with a protecting group that is removed as a result of the action of a component in the subject's body (e.g, a carboxyesterase or an enzyme present in the subject's body). For example, the iRNA agent could be a phosphate prodrug in which a carboxy esterase cleaves the protected molecule resulting in the production of a thioate anion that attacks a carbon adjacent to the oxygen of a phosphate resulting in the production of an unprotected phosphate.

One or more different NRM modifications can be introduced into an iRNA agent or into a sequence of an iRNA agent. An NRM modification can be used more than once in a sequence or in an iRNA agent. As some NRMs interfere with hybridization, the total number incorporated should be such that acceptable levels of iRNA agent duplex formation are maintained.

In some embodiments NRM modifications are introduced into the termini or in the internal region of the sense strand of the iRNA agent that does not hybridize with the desired target sequence or gene in the subject. This can reduce off-target silencing.

Nuclease resistant modifications include some that can be placed only at a terminus and others that can go at any position. It is preferable to use those modifications that inhibit hybridization only in terminal regions, and preferable to not use them at the cleavage site or in the cleavage region of an sequence that targets a subject sequence or gene. These modifications can be used anywhere in a sense strand, provided that sufficient hybridization between the two sequences of the iRNA agent is maintained. In some embodiments it is desirable to put the NRM in the internal region of the sense strand to minimize off-target silencing.

In addition, an iRNA agent described herein can have an overhang that does not form a duplex structure with the other sequence of the iRNA agent and does not hybridize with itself.

In most cases, the nuclease-resistance promoting modifications will be distributed differently depending on whether the sequence will target a sequence in the subject (this strand of the iRNA agent is often referred to as an antisense sequence or the guide sequence) or will not target a sequence in the subject (often referred to as a sense sequence). If a sequence is to target a sequence in the subject, modifications that interfere with or inhibit endonuclease cleavage should not be inserted in the region that guides RISC-mediated cleavage (e.g., the cleavage site or the cleavage region, as described in Elbashir et al., 2001, Genes and Dev. 15: 188, hereby incorporated by reference). Cleavage of the target occurs in the target opposite the middle of a 20 or 21 nt guide RNA, or about 10 or 11 nucleotides upstream of the first nucleotide that is complementary to the guide sequence. As used herein cleavage site refers to the nucleotide on either side of the cleavage site on the target or on the iRNA agent strand that hybridizes to it. Cleavage region means the region that are 1, 2, or 3 nucleotides on both sides of the cleave site.

Such modifications can be introduced into the terminal regions (e.g., at the terminal position or within 2, 3, 4, or 5 positions of the terminus) of a sequence that targets or a sequence that does not target a sequence in the subject.

Ribose Mimics

The monomers and methods described herein can be used to prepare an iRNA agent that incorporates a ribose mimic.

Thus, one aspect featured in the invention features an iRNA agent that includes a secondary hydroxyl group that can increase efficacy and/or confer nuclease resistance to the agent. Nucleases (e.g., cellular or serum nucleases) can hydrolyze nucleic acid phosphodiester bonds, resulting in partial or complete degradation of the nucleic acid. The secondary hydroxy group confers nuclease resistance to an iRNA agent by rendering the iRNA agent less prone to nuclease degradation relative to an iRNA that lacks the modification. While not wishing to be bound by theory, it is believed that the presence of a secondary hydroxyl group on the iRNA agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety that is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the iRNA agent. In preferred embodiments, there are five intervening bonds between the terminal phosphate group phosphorus and the secondary hydroxyl group.

Preferred iRNA agent delivery modules with five intervening bonds between the terminal phosphate group phosphorus and the secondary hydroxyl group have the following structure (see formula Y below):

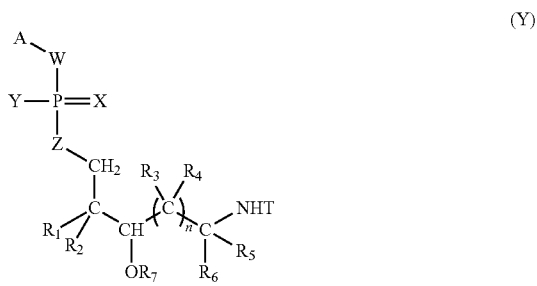

(Y)

Referring to formula Y, A is an iRNA agent, including any iRNA agent described herein. The iRNA agent may be connected directly or indirectly (e.g., through a spacer or linker) to "W" of the phosphate group. These spacers or linkers can include, for example, —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, morpholino, biotin, or fluorescein reagents.

The iRNA agents can have a terminal phosphate group that is unmodified (e.g., W, X, Y, and Z are O) or modified. In a modified phosphate group, W and Z can be independently NH, O, or S; and X and Y can be independently S, Se, $BH_3^-$, $C_1$-$C_6$ alkyl, $C_6$-$C_{10}$ aryl, H, O, O$^-$, alkoxy or amino (including alkylamino, arylamino, etc.). Preferably, W, X and Z are O and Y is S.

$R_1$ and $R_3$ are each, independently, hydrogen or $C_1$-$C_{100}$ alkyl, optionally substituted with hydroxyl, amino, halo, phosphate, or sulfate, and/or may be optionally inserted with N, O, S, alkenyl, or alkynyl.

$R_2$ is hydrogen; $C_1$-$C_{100}$ alkyl, optionally substituted with hydroxyl, amino, halo, phosphate, or sulfate and/or may be optionally inserted with N, O, S, alkenyl, or alkynyl; or, when n is 1, $R_2$ may be taken together with $R^4$ or $R^6$ to form a ring of 5-12 atoms.

$R^4$ is hydrogen; $C_1$-$C_{100}$ alkyl, optionally substituted with hydroxyl, amino, halo, phosphate, or sulfate, and/or may be optionally inserted with N, O, S, alkenyl or alkynyl; or, when n is 1, $R_4$ may be taken together with $R_2$ or $R_5$ to form a ring of 5-12 atoms.

$R_5$ is hydrogen; $C_1$-$C_{100}$ alkyl optionally substituted with hydroxyl, amino, halo, phosphate, or sulfate, and/or may be optionally inserted with N, O, S, alkenyl, or alkynyl; or, when n is 1, $R_5$ may be taken together with $R^4$ to form a ring of 5-12 atoms.

$R^6$ is hydrogen; $C_1$-$C_{100}$ alkyl, optionally substituted with hydroxyl, amino, halo, phosphate, or sulfate, and/or may be optionally inserted with N, O, S, alkenyl, or alkynyl; or, when n is 1, $R_6$ may be taken together with $R_2$ to form a ring of 6-10 atoms;

$R_7$ is hydrogen, $C_1$-$C_{100}$ alkyl, or $C(O)(CH_2)_qC(O)NHR_9$; T is hydrogen or a functional group; n and q are each independently 1-100; $R_8$ is $C_1$-$C_{10}$ alkyl or $C_6$-$C_{10}$ aryl; and $R_9$ is hydrogen, C1-C10 alkyl, C6-C10 aryl, or a solid support agent.

Preferred embodiments may include one of more of the following subsets of iRNA agent delivery modules.

In one subset of RNAi agent delivery modules, A can be connected directly or indirectly through a terminal 3' or 5' ribose sugar carbon of the RNA agent.

In another subset of RNAi agent delivery modules, X, W, and Z are O and Y is S.

In still yet another subset of RNAi agent delivery modules, n is 1, and $R_2$ and $R_6$ are taken together to form a ring containing six atoms and $R^4$ and $R_5$ are taken together to form a ring containing six atoms. Preferably, the ring system is a trans-decalin. For example, the RNAi agent delivery module of this subset can include a compound of Formula (Y-1):

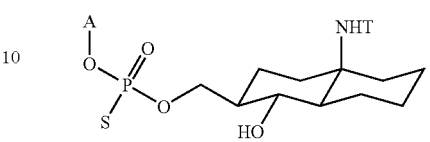

The functional group can be, for example, a targeting group (e.g., a steroid or a carbohydrate), a reporter group (e.g., a fluorophore), or a label (an isotopically-labeled moiety). The targeting group can further include protein binding agents, endothelial cell targeting groups (e.g., RGD peptides and mimetics), cancer cell targeting groups (e.g., folate vitamin B12, biotin), bone cell targeting groups (e.g., bisphosphonates, polyglutamates, polyaspartates), macrophage targeting groups (e.g., multivalent mannose), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof The invention is further illustrated by the following examples, which should not be construed as further limiting.

EXAMPLES

Example 1

Figure 2:
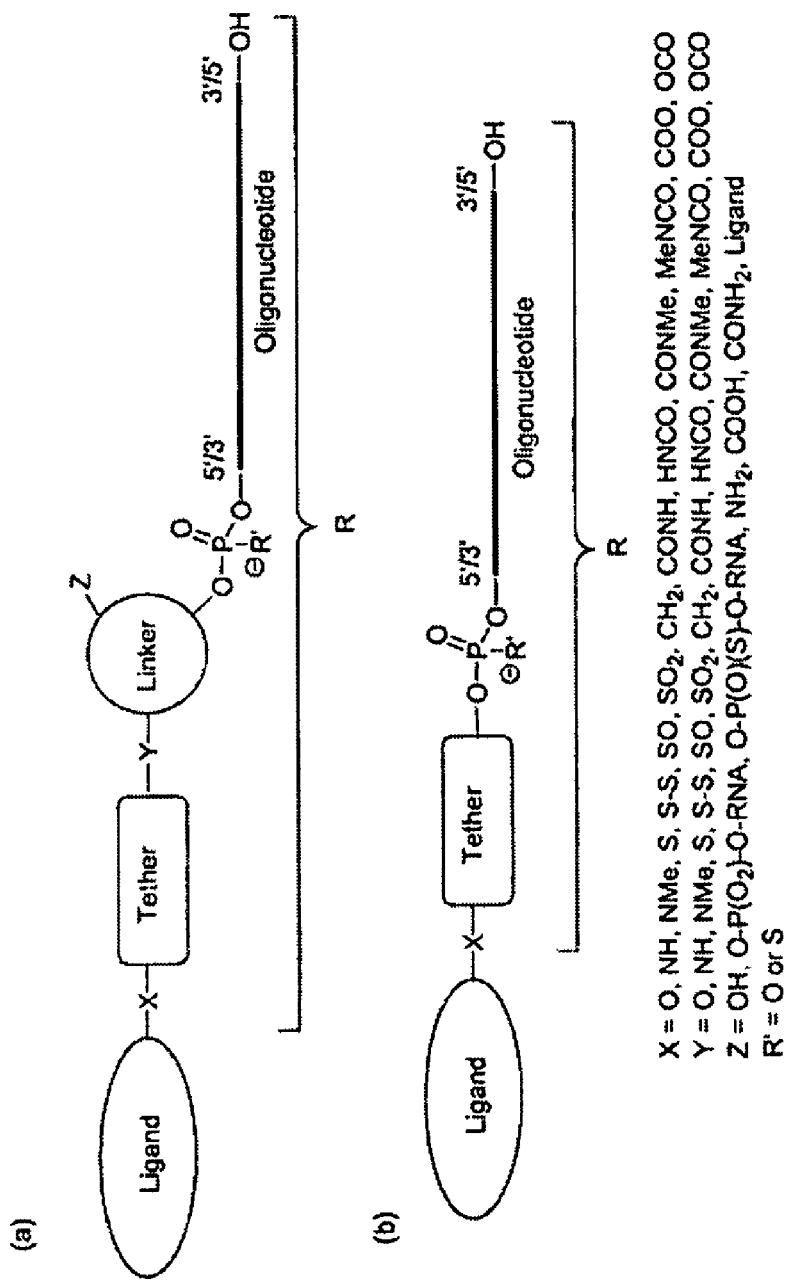
FIG. 2 is a schematic of a ligand-oligonucleotide (single-stranded) conjugate.
Figure 3:
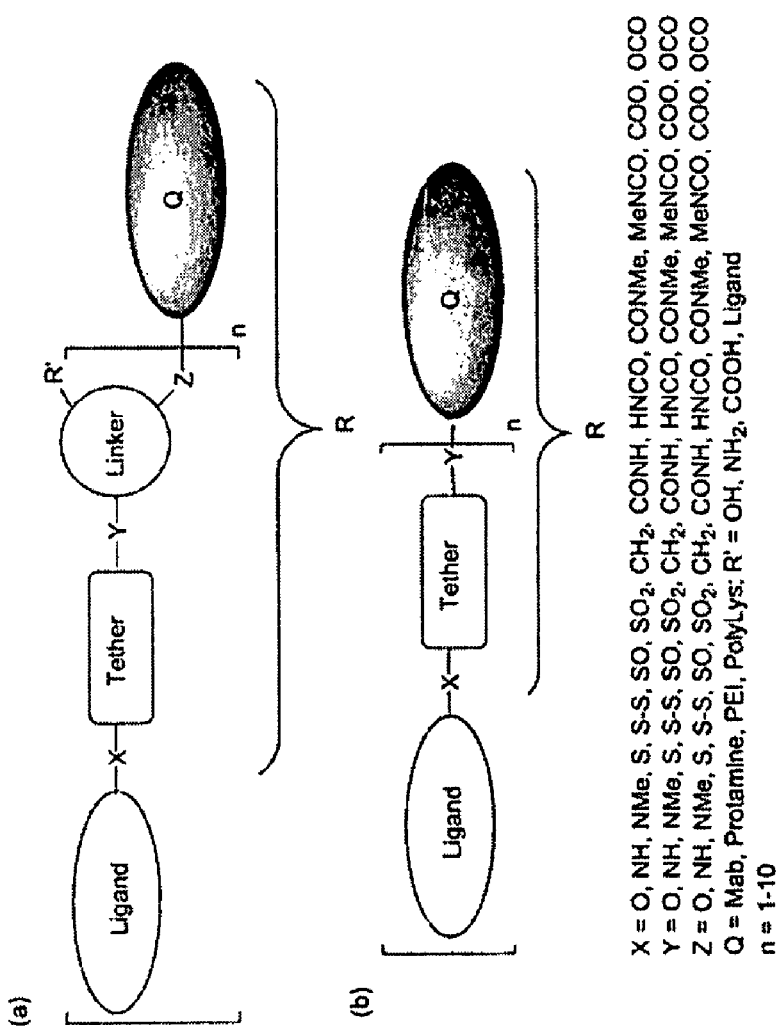
FIG. 3 is a schematic of a ligand-carrier (protein) conjugate. The carrier protein is indicated by the oval labeled Q.
Figure 4:
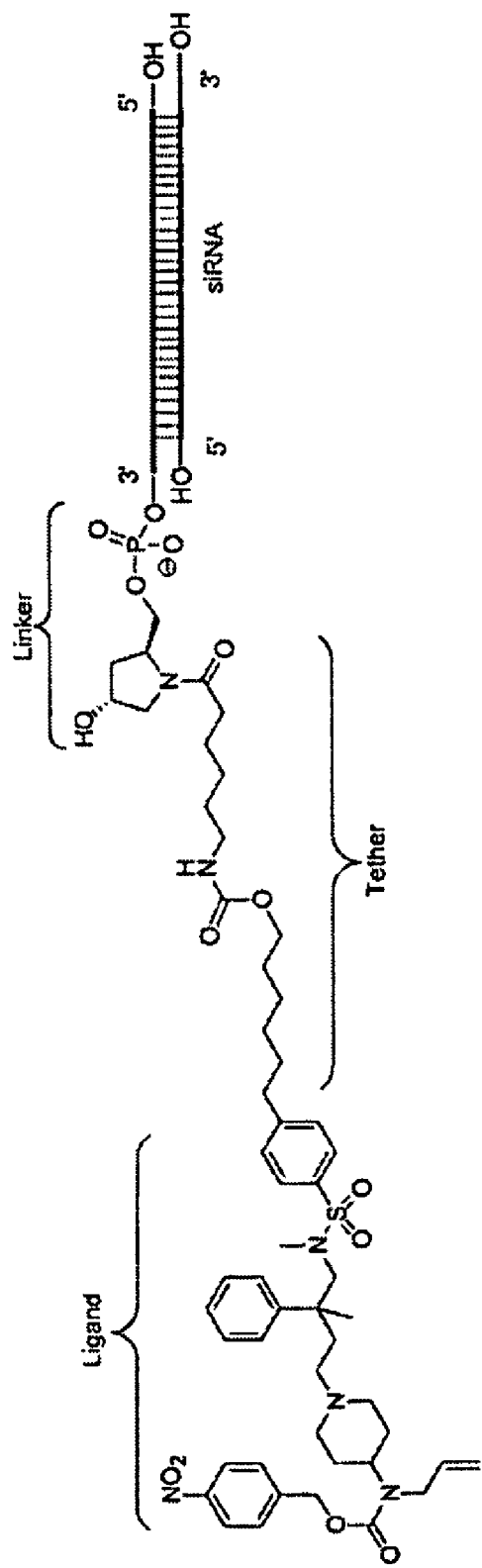
FIG. 4 is a schematic of a CCR5 antagonist-siRNA conjugate. The CCR5 antagonist is compound 21 (Table 1).

Small molecule CCR5 antagonists were conjugated to oligonucleotides for specific single- and/or double-stranded nucleic acid based therapeutic applications. An oligonucleotide for use in the conjugates is a chemically modified or unmodified RNA; or chemically modified chimera of DNA, DNA-RNA, RNA-DNA, DNA-RNA-DNA, or RNA-DNA-RNA. The attached (or conjugated) CCR5 antagonist recognizes the CCR5 receptor on the cell surface and binds to it, and this in turn carries the attached single- or double-stranded oligonucleotide to the cell type that expresses the receptor and helps to internalize the nucleic acid drug molecule. Column II of Table 1 represents oligonucleotide-ligand conjugates derived from a known ligand shown in column I. The conjugate is comprised of three components: viz. a linker, a tether, and the ligand. FIGS. 1, 2, and 3 depict the conjugate design. FIG. 1 is a schematic of an exemplary ligand-siRNA conjugate. The conjugate is composed of a ligand (such as one of those shown in Table 1), a tether, a linker, and the double-stranded siRNA. FIG. 2 is a schematic of an exemplary ligand-oligonucleotide conjugate. The iRNA can be, for example, an miRNA, an anti-miRNA, a chemically modified RNA or DNA; or a DNA or DNA analog, such as for use in an antisense application. FIG. 3 is a schematic of an exemplary ligand-carrier conjugate. The carrier protein is indicated by the oval labeled Q. Examples of carrier proteins include monoclonal antibodies (Mab), protamine, polyethylenimine (PEI), and polyLysine.

Example 2

Method of synthesis of iRNA agents. iRNA agents modified for enhanced targeting to CCR5 cells can be synthesized using phosphoramidite technology on solid phase employing an AKTA 10 synthesizer (Amersham Biosciences, Piscataway, N.J.) at scales ranging from 35 to 60 µmol. Synthesis can be performed on solid supports made of controlled pore glass (CPG, 520 Å, with a loading of 70 µmol/g obtained from Prime Synthesis, Aston, Pa.) or polystyrene (Primer Support™ with a loading of 71 µmol/g obtained from Amersham Biosciences, Piscataway, N.J.). RNA phosphoramidites, 5'-O-dimethoxytrityl-N6-(t-butylphenoxyacetyl)-2'-O-t-butyldimethylsilyl-adenosine-3'-O-(2-cyanoethyl-N,N-diisopropylamino) phosphoramidite, 5'-O-dimethoxytrityl-N4-(t-butylphenoxyacetyl)-2'-O-t-butyldimethylsilyl-cytidine-3'-O-(2-cyanoethyl-N,N-diisopropylamino) phosphoramidite, 5'-O-dimethoxytrityl-N2-(t-butylphenoxyacetyl)-2'-O-t-butyldimethylsilyl-guanosine-3'-O-(2-cyanoethyl-N,N-diisopropylamino) phosphoramidite, and 5'-O-dimethoxytrityl-2'-O-t-butyldimethylsilyl-uridine-3'-O-(2-cyanoethyl-N,N-diisopropylamino) phosphoramidite, can be purchased from Proligo (Boulder, Colo.). 2'-O-Methyl-ribonucleoside phosphoramidites (Proligo) carry the same protecting groups as the RNA phosphoramidites with the exception of 2'-O-methyl-guanosine, which is N2 isobutyryl protected. All amidites can be dissolved in anhydrous acetonitrile (70 mM) and molecular sieves (3 Å) can be added. 5-Ethyl thiotetrazole (ETT, 600 mM in acetonitrile) can be used as the activator solution. Coupling times are about 8 minutes. Oxidation can be carried out either with a mixture of iodine/water/pyridine (50 mM/10%/90% (v/v)) for phosphodiester linkages or a 100 mM solution of 3-ethoxy-1,2,4-dithiazoline-5-one (EDITH) in anhydrous acetonitrile in order to introduce phosphorothioate linkages. Standard capping reagents can be used. The DMT can be left on to facilitate purification.

After solid-phase synthesis, the RNA can be cleaved from the support by passing 14 mL of a 3:1 (v/v) mixture of 40% methylamine in water (Fluka) and methylamine in ethanol (Fluka) through the synthesis column over a 30 min time period. The eluent can be divided into four 15 mL screw cap vials and heated to 65° C. for an additional 30 min. This solution can be subsequently dried down under reduced pressure in a speedvac. The residue in each vial can be dissolved in 250 µL N-methylpyrolidin-2-one (NMP), and 120 µL triethylamine (TEA) and 160 µL TEA·3HF added. This mixture can be brought to 65° C. for 2 h. After cooling to ambient temperature, 1.5 mL NMP and 1 mL of ethoxytrimethylsilane can be added. After 10 min, the oligoribonucleotide can be precipitated by adding 3 mL of ether. The pellets can be collected by centrifugation, the supernatants discarded, and the solids reconstituted in 1 mL buffer 10 mM sodium phosphate.

Synthesis schemes are shown above in Schemes 1a-7.

What is claimed is:

1. A compound having structure:

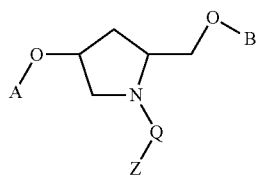

wherein,

A is H, a hydroxyl protecting group, a phosphate group, an activated phosphate group, an activated phosphite group, a phosphoramidite, a solid support, a nucleotide, or an oligonucleotide;

B is H, a hydroxyl protecting group, a phosphate group, an activated phosphate group, an activated phosphate group, a phosphoramidite, a solid support, a nucleotide, or an oligonucleotide;

Z is a CCR5-binding ligand;

Q is —C(O)(CH$_2$)$_n$NHC(O)(CH$_2$)$_m$NH—, —C(O)(CH$_2$)$_n$NHC(O)(CH$_2$)$_m$—, or —C(O)(CH$_2$)$_n$NH—;

n is 1-20; and m is 1-6.

2. The compound of claim 1, wherein A is an activated phosphite group, a phosphoramidite, or a solid support.

3. The compound of claim 1, wherein B is a hydroxyl protecting group.

4. The compound of claim 1, wherein Q is —C(O)(CH$_2$)$_n$NHC(O)(CH$_2$)$_m$NH—.

5. The compound of claim 1, wherein the CCR5-binding ligand is a CCR5 antagonist.

6. The compound of claim 5, wherein the CCR5 antagonist is an antagonist listed in column 1 of Table 1.

7. The compound of claim 6, wherein the CCR5 antagonist has the following structure

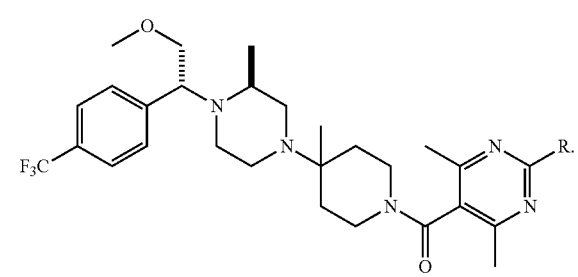

8. The compound of claim 6, wherein the CCR5 antagonist has the following structure

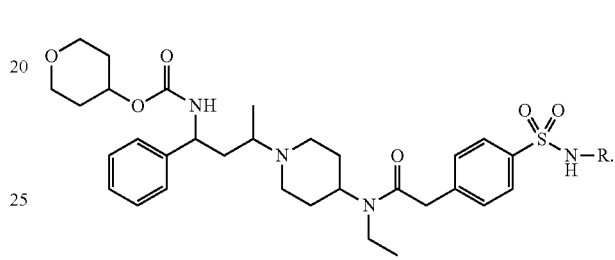

9. The compound of claim 6, wherein the CCR5 antagonist has the following structure

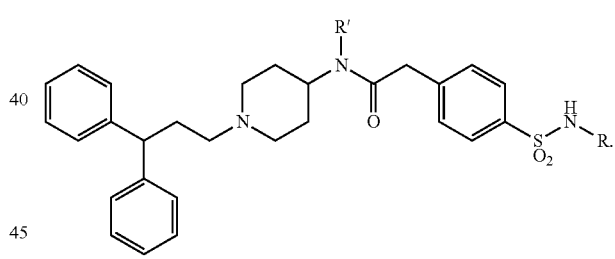

R' = H, Me, Et, Allyl, Cyclopropyl isobutyl, isopropyl

10. The compound of claim 6, wherein the CCR5 antagonist has the following structure

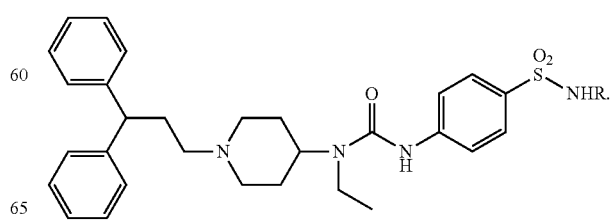

11. The compound of claim 6, wherein the CCR5 antagonist has the following structure

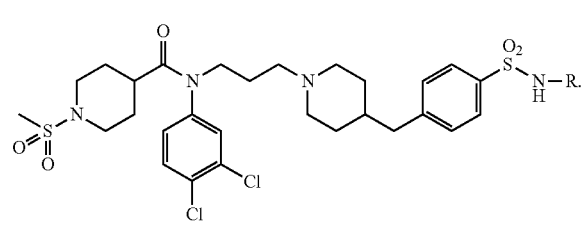

12. The compound of claim 6, wherein the CCR5 antagonist has the following structure

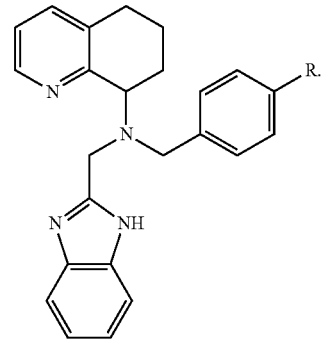

13. The compound of claim 6, wherein the CCR5 antagonist has the following structure

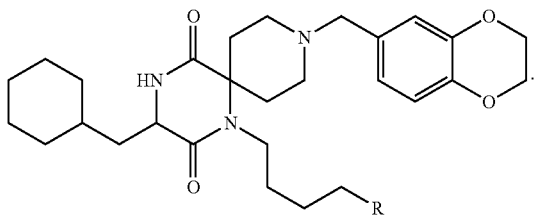

14. The compound of claim 6, wherein the CCR5 antagonist has the following structure

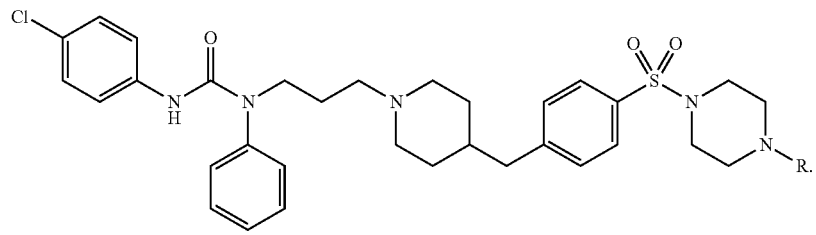

15. The compound of claim 6, wherein the CCR5 antagonist has the following structure

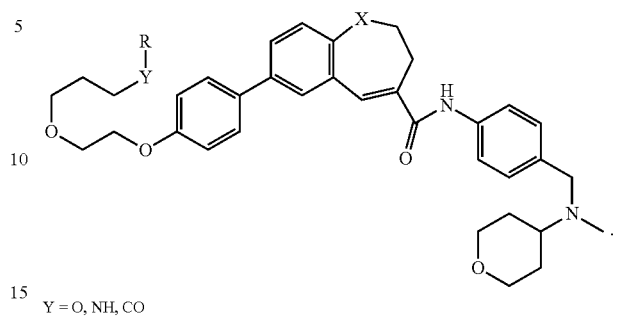

Y = O, NH, CO

16. The compound of claim 6, wherein the CCR5 antagonist has the following structure

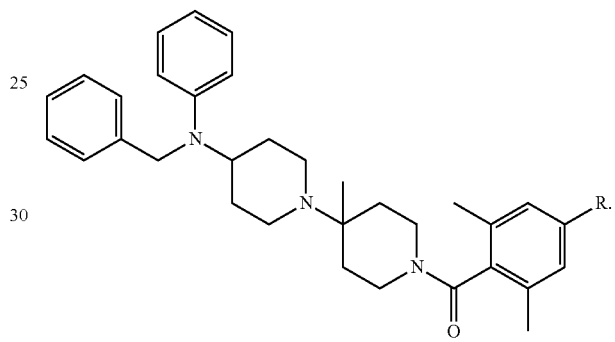

17. The compound of claim 6, wherein the CCR5 antagonist has the following structure

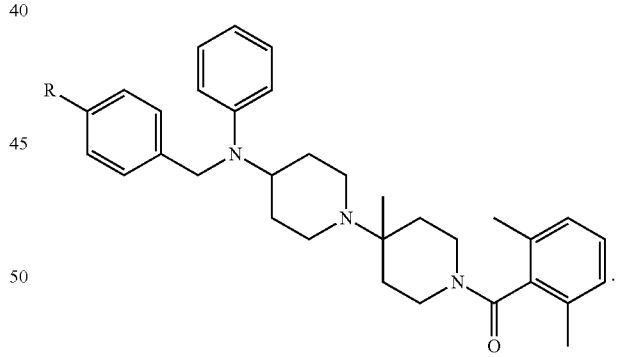

18. The compound of claim 6, wherein the CCR5 antagonist has the following structure

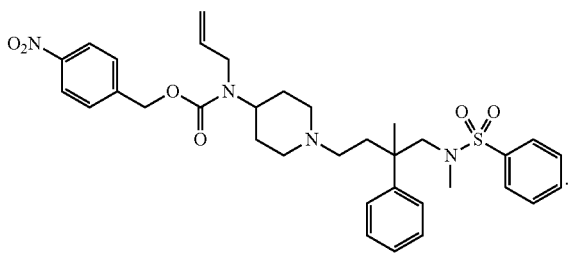

19. The compound of claim 1, wherein A is an oligonucleotide.

20. The compound of claim 19, wherein the oligonucleotide is double stranded.

21. The compound of claim 1, wherein B is an oligonucleotide.

22. The compound of claim 21, wherein the oligonucleotide is double stranded.

23. The compound of claim 1, wherein A is an oligonucleotide and B is an oligonucleotide.

24. The compound of claim 23, wherein oligonucleotide is double stranded.

* * * * *

SEQUENCE LISTING

```
<160> NUMBER OF SEQ ID NOS: 1

<210> SEQ ID NO 1
<211> LENGTH: 3655
<212> TYPE: DNA
<213> ORGANISM: Homo sapiens

<400> SEQUENCE: 1
cttcagatag attatatctg gagtgaagga tcctgccacc tacgtatctg gcatagtatt      60
ctgtgtagtg ggatgagcag agaacaaaaa caaaataatc cagtgagaaa agcccgtaaa     120
taaaccttca gaccagagat ctattctcca gcttatttta agctcaactt aaaaagaaga     180
actgttctct gattcttttc gccttcaata cacttaatga tttaactcca ccctccttca     240
aaagaaacag catttcctac ttttatactg tctatatgat tgatttgcac agctcatctg     300
gccagaagag ctgagacatc cgttcccta caagaaactc tccccgggtg gaacaagatg      360
gattatcaag tgtcaagtcc aatctatgac atcaattatt atacatcgga gccctgccaa      420
aaaatcaatg tgaagcaaat cgcagcccgc ctcctgcctc cgctctactc actggtgttc     480
atctttggtt ttgtgggcaa catgctggtc atcctcatcc tgataaactg caaaaggctg     540
aagagcatga ctgacatcta cctgctcaac ctggccatct ctgacctgtt tttccttctt     600
actgtcccct tctgggctca ctatgctgcc gcccagtggg actttggaaa tacaatgtgt     660
caactcttga caggctcta ttttataggc ttcttctctg gaatcttctt catcatcctc     720
ctgacaatcg ataggtacct ggctgtcgtc catgctgtgt tgctttaaa agccaggacg     780 gtcacctttg gggtggtgac aagtgtgatc acttgggtgg tggctgtgtt tgcgtctctc     840
ccaggaatca tctttaccag atctcaaaaa gaaggtcttc attacacctg cagctctcat     900
```

```
tttccataca gtcagtatca attctggaag aatttccaga cattaaagat agtcatcttg    960
gggctggtcc tgccgctgct tgtcatggtc atctgctact cgggaatcct aaaaactctg   1020
cttcggtgtc gaaatgagaa gaagaggcac agggctgtga ggcttatctt caccatcatg   1080
attgtttatt ttctcttctg gctccctac aacattgtcc ttctcctgaa cccttccag    1140
gaattctttg gcctgaataa ttgcagtagc tctaacaggt tggaccaagc tatgcaggtg   1200
acagagactc ttgggatgac gcactgctgc atcaacccca tcatctatgc ctttgtcggg   1260
gagaagttca gaaactacct cttagtcttc ttccaaaagc acattgccaa acgcttctgc   1320
aaatgctgtt ctattttcca gcaagaggct cccgagcgag caagctcagt ttacacccga   1380
tccactgggg agcaggaaat atctgtgggc ttgtgacacg gactcaagtg ggctggtgac   1440
ccagtcagag ttgtgcacat ggcttagttt catacacag cctgggctgg gggtgggtg    1500
ggagaggtct tttttaaaag gaagttactg ttatagaggg tctaagattc atccatttat   1560
ttggcatctg tttaaagtag attagatctt ttaagcccat caattataga aagccaaatc   1620
aaaatatgtt gatgaaaaat agcaacctttt ttatctcccc ttcacatgca tcaagttatt   1680
gacaaactct cccttcactc cgaaagttcc ttatgtatat ttaaaagaaa gcctcagaga   1740
attgctgatt cttgagttta gtgatctgaa cagaaatacc aaaattattt cagaaatgta   1800
caacttttta cctagtacaa ggcaacatat aggttgtaaa tgtgtttaaa acaggtcttt   1860
gtcttgctat ggggagaaaa gacatgaata tgattagtaa agaaatgaca cttttcatgt   1920
gtgatttccc ctccaaggta tggttaataa gtttcactga cttagaacca ggcgagagac   1980
ttgtggcctg ggagagctgg ggaagcttct taaatgagaa ggaatttgag ttggatcatc   2040
tattgctggc aaagacagaa gcctcactgc aagcactgca tgggcaagct tggctgtaga   2100
aggagacaga gctggttggg aagacatggg gaggaaggac aaggctagat catgaagaac   2160
cttgacggca ttgctccgtc taagtcatga gctgagcagg gagatcctgg ttggtgttgc   2220
agaaggttta ctctgtggcc aaaggagggt caggaaggat gagcatttag ggcaaggaga   2280
ccaccaacag ccctcaggtc agggtgagga tggcctctgc taagctcaag gcgtgaggat   2340
gggaaggagg gaggtattcg taaggatggg aaggaggag tattcgtgc agcatatgag    2400
gatgcagagt cagcagaact ggggtggatt tggtttggaa gtgagggtca gagaggagtc   2460
agagagaatc cctagtcttc aagcagattg gagaaaccct tgaaaagaca tcaagcacag   2520
aaggaggagg aggaggttta ggtcaagaag aagatggatt ggtgtaaaag gatgggtctg   2580
gtttgcagag cttgaacaca gtctcaccca gactccaggc tgtctttcac tgaatgcttc   2640
tgacttcata gatttccttc ccatcccagc tgaaatactg aggggtctcc aggaggagac   2700
tagatttatg aatacacgag gtatgaggtc taggaacata cttcagctca cacatgagat   2760
ctaggtgagg attgattacc tagtagtcat ttcatgggtt gttgggagga ttctatgagg   2820
caaccacagg cagcatttag cacatactac acattcaata agcatcaaac tcttagttac   2880
tcattcaggg atagcactga gcaaagcatt gagcaaaggg gtcccatata ggtgagggaa   2940
gcctgaaaaa ctaagatgct gcctgcccag tgcacacaag tgtaggtatc attttctgca   3000
tttaaccgtc aataggcaaa gggggaagg gacatattca tttggaaata agctgccttg   3060
agccttaaaa cccacaaaag tacaatttac cagcctccgt atttcagact gaatgggggt   3120
gggggggggcg ccttaggtac ttattccaga tgccttctcc agacaaacca gaagcaacag   3180
aaaaaatcgt ctctccctcc ctttgaaatg aatatacccc ttagtgtttg ggtatattca   3240
tttcaagggg agagagagag gttttttttct gttctttctc atatgattgt gcacatactt   3300
```

```
gagactgttt tgaatttggg ggatggctaa aaccatcata gtacaggtaa ggtgagggaa    3360
tagtaagtgg tgagaactac tcagggaatg aaggtgtcag aataataaga ggtgctactg    3420
actttctcag cctctgaata tgaacggtga gcattgtggc tgtcagcagg aagcaacgaa    3480
gggaaatgtc tttcctttg ctcttaagtt gtggagagtg caacagtagc ataggaccct     3540
accctctggg ccaagtcaaa gacattctga catcttagta tttgcatatt cttatgtatg    3600
tgaaagttac aaattgcttg aaagaaaata tgcatctaat aaaaaacacc ttcta         3655
```